(12) United States Patent
Giovanni et al.

(10) Patent No.: US 11,896,466 B2
(45) Date of Patent: Feb. 13, 2024

(54) ABSORBENT ARTICLES HAVING SHAPED, SOFT AND TEXTURED NONWOVEN FABRICS

(71) Applicant: The Procter & Gamble Company, Cincinnati, OH (US)

(72) Inventors: Sara L. Giovanni, Cincinnati, OH (US); Arman Ashraf, Mason, OH (US); Paul T. Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1027 days.

(21) Appl. No.: 16/435,805

(22) Filed: Jun. 10, 2019

(65) Prior Publication Data

US 2019/0374407 A1    Dec. 12, 2019

Related U.S. Application Data

(60) Provisional application No. 62/683,661, filed on Jun. 12, 2018.

(51) Int. Cl.
*A61F 13/511* (2006.01)
*A61F 13/514* (2006.01)
(Continued)

(52) U.S. Cl.
CPC .. *A61F 13/15203* (2013.01); *A61F 13/15642* (2013.01); *A61F 13/15707* (2013.01);
(Continued)

(58) Field of Classification Search
CPC .......... A61F 13/15203; A61F 13/51104; A61F 13/51108; A61F 13/51121; A61F 13/512;
(Continued)

(56) References Cited

U.S. PATENT DOCUMENTS

| | | | |
|---|---|---|---|
| 3,832,281 A | * | 8/1974 | Kawai ................ D21H 13/08 264/197 |
| 4,333,979 A | | 6/1982 | Sciaraffa et al. |

(Continued)

FOREIGN PATENT DOCUMENTS

| | | |
|---|---|---|
| CA | 2880427 A1 | 2/2014 |
| CN | 1286736 A | 3/2001 |

(Continued)

OTHER PUBLICATIONS

International Search Report and Written Opinion, PCT/US2019/036228.

(Continued)

*Primary Examiner* — Catharine L Anderson
*Assistant Examiner* — Lynne Anderson
(74) *Attorney, Agent, or Firm* — Christian M. Best

(57) ABSTRACT

Absorbent articles are provided that comprise shaped, soft and textured nonwoven fabrics. The nonwoven fabrics may be a topsheet and an outer cover nonwoven material of the absorbent article. A portion of a wearer-facing surface of the topsheet may have a TS7 in the range of about 1 dB $V^2$ rms of about 1 to about 4.5 dB $V^2$ rms and a TS750 in the range of about 6 dB $V^2$ rms to about 30 dB $V^2$ rms. A portion of a garment-facing surface of the outer cover nonwoven material may have a TS7 in the range of about 1 dB $V^2$ rms of about 1 to about 4.5 dB $V^2$ rms and a TS750 in the range of about 6 dB $V^2$ rms to about 30 dB $V^2$ rms. The nonwoven fabrics of the present disclosure provide soft materials with texture.

21 Claims, 35 Drawing Sheets

(51) Int. Cl.
*A61F 13/15* (2006.01)
*D04H 3/147* (2012.01)
*A61F 13/51* (2006.01)
*A61F 13/84* (2006.01)

(52) U.S. Cl.
CPC .. *A61F 13/51104* (2013.01); *A61F 13/51108* (2013.01); *A61F 13/51121* (2013.01); *A61F 13/51474* (2013.01); *D04H 3/147* (2013.01); *A61F 13/84* (2013.01); A61F 2013/15357 (2013.01); A61F 2013/51038 (2013.01); A61F 2013/5149 (2013.01); A61F 2013/51452 (2013.01); A61F 2013/8497 (2013.01); D10B 2401/021 (2013.01); D10B 2401/022 (2013.01); D10B 2509/026 (2013.01)

(58) Field of Classification Search
CPC .............. A61F 13/5121; A61F 13/5122; A61F 13/513; A61F 13/51394; A61F 13/51474; A61F 2013/51338; A61F 2013/51344; A61F 2013/5149; A61F 2013/8497
See application file for complete search history.

(56) References Cited

U.S. PATENT DOCUMENTS

| | | | |
|---|---|---|---|
| 4,741,941 | A | 5/1988 | Englebert et al. |
| 4,970,104 | A | 11/1990 | Radwanski |
| 5,158,819 | A | 10/1992 | Goodman, Jr. et al. |
| 5,334,289 | A | 8/1994 | Trokhan et al. |
| 5,399,174 | A | 3/1995 | Yeo et al. |
| 5,514,523 | A | 5/1996 | Trokhan et al. |
| 5,575,874 | A | 11/1996 | Griesbach et al. |
| 5,599,420 | A | 2/1997 | Yeo et al. |
| 5,643,653 | A | 7/1997 | Griesbach, III et al. |
| 5,667,625 | A | 9/1997 | Alikhan |
| 5,725,927 | A | 3/1998 | Zilg et al. |
| 5,858,504 | A | 1/1999 | Steven |
| 5,895,623 | A | 4/1999 | Trokhan et al. |
| 5,916,661 | A | 6/1999 | Benson et al. |
| 5,990,377 | A | 11/1999 | Chen |
| 6,139,941 | A | 10/2000 | Jankevics et al. |
| 6,231,555 | B1 | 5/2001 | Lynard |
| 6,319,455 | B1 | 11/2001 | Kauschke et al. |
| 6,331,268 | B1 | 12/2001 | Kauschke et al. |
| 6,331,345 | B1 | 12/2001 | Kauschke et al. |
| 6,361,638 | B2 | 3/2002 | Takai et al. |
| 6,383,431 | B1 | 5/2002 | Dobrin et al. |
| 6,395,957 | B1 | 5/2002 | Chen et al. |
| 6,409,715 | B1 * | 6/2002 | Tanji ............... A61F 13/513 604/385.19 |
| 6,436,512 | B1 | 8/2002 | Kauschke et al. |
| 6,632,504 | B1 | 10/2003 | Gillespie et al. |
| 6,673,418 | B1 | 1/2004 | DeOlivera et al. |
| 6,713,661 | B1 * | 3/2004 | Arndt ............... A61F 13/15203 604/385.101 |
| 6,818,802 | B2 | 11/2004 | Takai et al. |
| 6,890,622 | B2 | 5/2005 | Adam et al. |
| 6,897,351 | B2 * | 5/2005 | Nakaoka ........... A61F 13/49406 604/385.01 |
| 7,005,558 | B1 | 2/2006 | Johansson et al. |
| 7,507,463 | B2 | 3/2009 | Noda et al. |
| 7,553,535 | B2 | 6/2009 | Noda et al. |
| 7,662,462 | B2 | 2/2010 | Noda et al. |
| 7,897,240 | B2 | 3/2011 | Noda et al. |
| 7,954,213 | B2 | 6/2011 | Mizutani et al. |
| 7,955,549 | B2 | 6/2011 | Noda et al. |
| 8,128,771 | B2 * | 3/2012 | Endo ............... A61F 13/49011 156/496 |
| 8,143,177 | B2 | 3/2012 | Noda et al. |
| 8,183,431 | B2 | 5/2012 | Noda et al. |
| 8,273,941 | B2 | 9/2012 | Uematsu et al. |
| 8,304,600 | B2 | 11/2012 | Noda et al. |
| 8,435,223 | B2 | 5/2013 | Roe |
| 8,574,209 | B2 | 11/2013 | Nishitani et al. |
| 8,585,666 | B2 | 11/2013 | Weisman et al. |
| 8,758,569 | B2 | 6/2014 | Aberg et al. |
| 8,853,108 | B2 | 10/2014 | Ahoniemi et al. |
| 8,865,965 | B2 | 10/2014 | Sato et al. |
| 8,906,275 | B2 | 12/2014 | Davis et al. |
| 9,095,477 | B2 | 8/2015 | Yamaguchi et al. |
| 9,156,229 | B2 | 10/2015 | Yoda et al. |
| 9,205,005 | B2 | 12/2015 | Kikuchi et al. |
| 9,453,303 | B2 | 9/2016 | Aberg et al. |
| 9,732,454 | B2 | 8/2017 | Davis et al. |
| 9,867,740 | B2 | 1/2018 | Zink et al. |
| 9,877,876 | B2 | 1/2018 | Huang et al. |
| 9,903,070 | B2 | 2/2018 | Mourad et al. |
| 10,190,244 | B2 | 1/2019 | Ashraf et al. |
| 10,639,212 | B2 | 5/2020 | Kanya et al. |
| 10,772,768 | B2 | 9/2020 | Ashraf et al. |
| 11,033,439 | B2 | 6/2021 | Een et al. |
| 11,090,197 | B2 | 8/2021 | Ashraf et al. |
| 2001/0029141 | A1 | 10/2001 | Mizutani et al. |
| 2002/0103469 | A1 | 8/2002 | Chen et al. |
| 2002/0153271 | A1 | 10/2002 | McManus et al. |
| 2002/0193032 | A1 | 12/2002 | Newkirk et al. |
| 2003/0093045 | A1 | 5/2003 | Jensen |
| 2003/0118780 | A1 | 6/2003 | Adam et al. |
| 2003/0119404 | A1 | 6/2003 | Belau et al. |
| 2003/0125687 | A1 | 7/2003 | Gubernick et al. |
| 2003/0203162 | A1 | 10/2003 | Christopher et al. |
| 2003/0203691 | A1 | 10/2003 | Fenwick et al. |
| 2003/0211802 | A1 | 11/2003 | Keck et al. |
| 2004/0059309 | A1 | 3/2004 | Nortman |
| 2005/0003152 | A1 | 1/2005 | Thomas et al. |
| 2005/0148969 | A1 | 7/2005 | Damay et al. |
| 2005/0148971 | A1 | 7/2005 | Kuroda et al. |
| 2006/0087053 | A1 | 4/2006 | O'Donnell et al. |
| 2006/0105075 | A1 | 5/2006 | Otsubo |
| 2006/0189954 | A1 | 8/2006 | Kudo et al. |
| 2007/0026753 | A1 | 2/2007 | Neely et al. |
| 2007/0045143 | A1 | 3/2007 | Clough et al. |
| 2007/0045144 | A1 | 3/2007 | Wheeler et al. |
| 2007/0179466 | A1 | 8/2007 | Tremblay et al. |
| 2007/0298214 | A1 | 12/2007 | Noda et al. |
| 2007/0298667 | A1 | 12/2007 | Noda et al. |
| 2008/0149292 | A1 | 6/2008 | Scherb |
| 2009/0240222 | A1 | 9/2009 | Tomoko et al. |
| 2010/0036346 | A1 | 2/2010 | Hammons |
| 2010/0048072 | A1 | 2/2010 | Kauschke |
| 2010/0297378 | A1 | 11/2010 | Mellin et al. |
| 2011/0073513 | A1 | 3/2011 | Weisman et al. |
| 2011/0250378 | A1 | 10/2011 | Eaton et al. |
| 2012/0004633 | A1 | 1/2012 | Marcelo et al. |
| 2012/0177886 | A1 | 7/2012 | Kanya |
| 2012/0196091 | A1 | 8/2012 | Mizutani et al. |
| 2013/0112584 | A1 | 5/2013 | Gaspari et al. |
| 2013/0139960 | A1 | 6/2013 | Maruyama et al. |
| 2013/0171421 | A1 | 7/2013 | Weisman et al. |
| 2013/0197462 | A1 | 8/2013 | Abuto et al. |
| 2013/0320584 | A1 | 12/2013 | Davis et al. |
| 2014/0127459 | A1 | 5/2014 | Xu |
| 2014/0127460 | A1 | 5/2014 | Xu et al. |
| 2014/0234575 | A1 | 8/2014 | Mitsuno et al. |
| 2014/0276517 | A1 | 9/2014 | Chester et al. |
| 2014/0296815 | A1 | 10/2014 | Takken et al. |
| 2014/0305570 | A1 | 10/2014 | Matsunaga et al. |
| 2014/0324009 | A1 | 10/2014 | Lee et al. |
| 2015/0173967 | A1 | 6/2015 | Kreuzer et al. |
| 2015/0182387 | A1 | 7/2015 | Ferrer et al. |
| 2015/0282999 | A1 | 10/2015 | Ariziti et al. |
| 2015/0328056 | A1 | 11/2015 | Een |
| 2016/0067119 | A1 | 3/2016 | Weisman et al. |
| 2016/0074244 | A1 | 3/2016 | Rosati et al. |
| 2016/0074252 | A1 | 3/2016 | Strube et al. |
| 2016/0076180 | A1 | 3/2016 | Strube et al. |
| 2016/0106633 | A1 | 4/2016 | Nagata et al. |
| 2016/0129661 | A1 | 5/2016 | Arora et al. |
| 2016/0136009 | A1 | 5/2016 | Weisman et al. |
| 2016/0167334 | A1 | 6/2016 | Arora et al. |
| 2016/0250353 | A1 | 9/2016 | Zawadzki et al. |
| 2017/0009401 | A1 | 1/2017 | O'brien Stickney et al. |

(56) References Cited

U.S. PATENT DOCUMENTS

| | | |
|---|---|---|
| 2017/0014281 A1 | 1/2017 | Xie |
| 2017/0014291 A1 | 1/2017 | Tao et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0121873 A1 | 5/2017 | Kimura et al. |
| 2017/0191198 A1 | 7/2017 | Ashraf et al. |
| 2017/0258650 A1 | 9/2017 | Rosati et al. |
| 2017/0348163 A1 | 12/2017 | Lakso et al. |
| 2018/0058011 A1 | 3/2018 | Sealey et al. |
| 2018/0168893 A1 | 6/2018 | Ashraf et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2019/0003079 A1 | 1/2019 | Ashraf et al. |
| 2019/0003080 A1 | 1/2019 | Ashraf et al. |
| 2019/0112737 A1 | 4/2019 | Ashraf et al. |
| 2019/0374388 A1 | 12/2019 | Giovanni et al. |
| 2019/0374405 A1 | 12/2019 | Giovanni et al. |
| 2020/0054501 A1 | 2/2020 | Seto et al. |
| 2021/0045941 A1 | 2/2021 | Ashraf et al. |

FOREIGN PATENT DOCUMENTS

| | | |
|---|---|---|
| CN | 1685099 | 10/2005 |
| CN | 103767830 A | 5/2014 |
| CN | 104661627 A | 5/2015 |
| CN | 106163478 A | 11/2016 |
| CN | 107072835 A | 8/2017 |
| EP | 2660377 | 4/2014 |
| EP | 2891480 A1 | 7/2015 |
| JP | H08246321 A | 9/1996 |
| JP | 2005245789 A | 9/2005 |
| JP | 2009-136349 | 6/2009 |
| JP | 2009268559 A | 11/2009 |
| JP | 2011-015707 | 1/2011 |
| JP | 2014-097257 | 5/2014 |
| JP | 2014-188042 | 10/2014 |
| JP | 2016089277 A | 5/2016 |
| JP | 2016101259 A | 6/2016 |
| JP | 2017115262 A | 6/2017 |
| JP | 2017213073 A | 12/2017 |
| JP | 2019010348 A | 1/2019 |
| RU | 2375081 C1 | 12/2009 |
| RU | 2415659 C1 | 4/2011 |
| WO | 9611107 A1 | 4/1996 |
| WO | 9932698 A1 | 7/1999 |
| WO | 2005113126 A1 | 12/2005 |
| WO | WO201286730 | 6/2012 |
| WO | WO 2003-015681 | 2/2013 |
| WO | WO201318846 | 2/2013 |
| WO | WO 2013-084977 | 6/2013 |
| WO | WO201399625 | 7/2013 |
| WO | WO2013145966 | 10/2013 |
| WO | WO 2017-105997 | 6/2017 |
| WO | WO2017110695 | 6/2017 |

OTHER PUBLICATIONS

3D Nonwovens Developments for textured nonwovens; Detlef Frey; http://web.archive.org/web/20170919080326/https://www.reicofil.com/en/pages/3d_nonwovens, Sep. 19, 2017.
All Office Actions U.S. Appl. No. 15/840,455.
All Office Actions U.S. Appl. No. 16/435,796.
All Office Actions U.S. Appl. No. 16/435,811.
All Office Actions; U.S. Appl. No. 17/087,695.
Unpublished U.S. Appl. No. 18/192,765, filed Mar. 30, 2023, to Arman Ashraf et. al.
All Office Actions; U.S. Appl. No. 18/192,765, filed Mar. 30, 2023.
All Office Actions; U.S. Appl. No. 18/318,955, filed May 17, 2023.
Define Textile, "Softening of Textile", URL Link: www.definetextile.com/2013/06/softening-of-textile.html, dated Jun. 20, 2023, 2 pgs.
Textile Glossary definition of "Hand", Celanese Acetate LLC, year 2001, 1 page.
U.S. Unpublished U.S. Appl. No. 18/318,955, filed May 17, 2023, to Arman Ashraf et al.

* cited by examiner

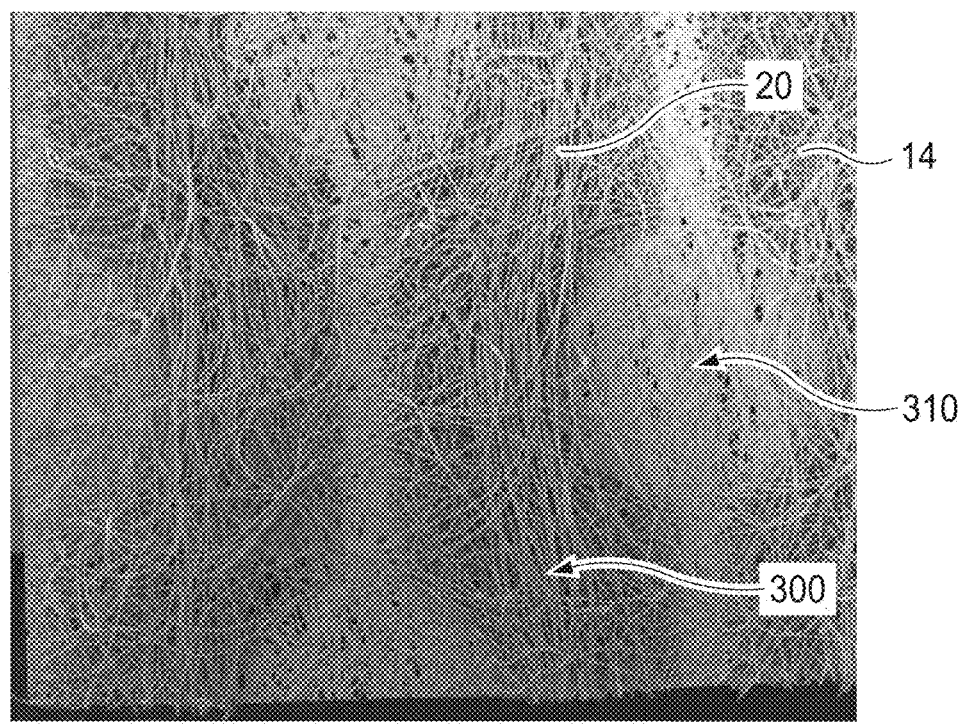
FIG. 32
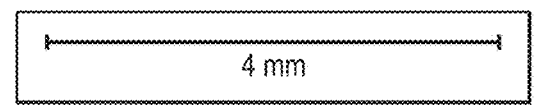
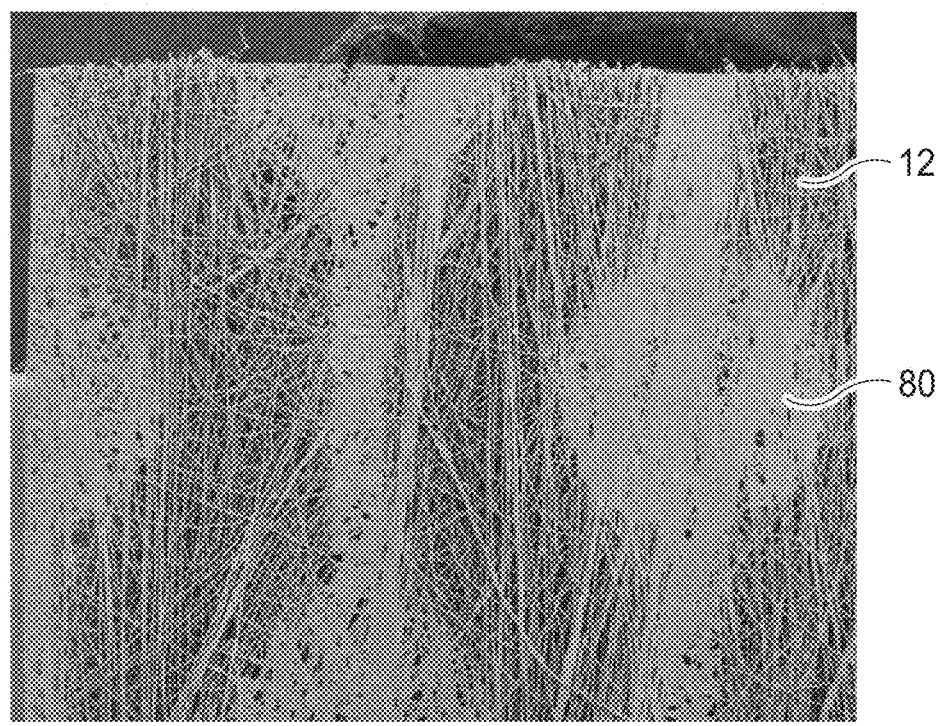
FIG. 33
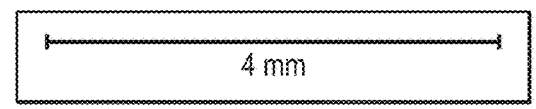

ABSORBENT ARTICLES HAVING SHAPED, SOFT AND TEXTURED NONWOVEN FABRICS

CROSS REFERENCE TO RELATED APPLICATION

This application claims the benefit, under 35 U.S.C. § 119(e), to U.S. Provisional Patent Application No. 62/683,661, filed on Jun. 12, 2018, which is herein incorporated by reference in its entirety.

FIELD

The present disclosure is directed to absorbent articles having shaped, soft and textured nonwoven fabrics.

BACKGROUND

Absorbent articles are used to contain and absorb bodily exudates (i.e., urine, bowel movements, and menses) in infants, children, and adults. Absorbent articles may include, but not be limited to, diapers, pants, adult incontinence products, feminine care products, and absorbent pads. Various components of these absorbent articles comprise nonwoven fabrics. Two example components that comprise nonwoven fabrics are an outer cover nonwoven material and a topsheet. Consumers desire that these two components, which form at least portions of the garment-facing surface and wearer-facing surface, respectively, of an absorbent article, have a certain look and feel, while still providing superior performance. Superior performance for a topsheet may be a soft tactile feel while also having texture for bodily exudate handling, breathability, and skin dryness. Superior performance for an outer cover nonwoven material may be aesthetically pleasing texture communicating softness and gentleness while being tactilely soft to the touch. Texture and softness are important attributes that consumers desire in these two components. Typically, however, the more textured a nonwoven fabric is, the less soft it is and vice versa. As such, nonwoven fabrics should be improved.

SUMMARY

The present disclosure provides absorbent articles comprising shaped, soft, and textured nonwoven fabrics that solve the contradiction between texture and softness. Typically, the more textured a nonwoven fabric is, the less soft it is. Likewise, the softer nonwoven fabrics typically have very little, if any, texture. The present disclosure provides a solution to that problem by providing absorbent articles comprising nonwoven fabrics with high softness and high texture. The present disclosure further provides a solution that solves the contradiction between high softness and high texture while simultaneously providing some improvements in fluid handling, including rapid strikethrough of bodily exudates and enhanced skin and topsheet dryness. Typically, the nonwoven fabrics of the present disclosure may form at least a portion of a wearer-facing surface (e.g., topsheet) and at least a portion of a garment-facing surface (e.g., outer cover nonwoven material). Softness, texture (i.e., smoothness), and/or stiffness may be measured by an Emtec Tissue Softness Analyzer, according to the Emtec Test herein. Tactile softness is measured as TS7. Texture/Smoothness is measured as TS750. Stiffness is measured as D.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 32 is a photograph of a portion of an example nonwoven fabric of the present disclosure.

FIG. 33 is a photograph of a portion of an example nonwoven fabric of the present disclosure.

DETAILED DESCRIPTION

Various non-limiting forms of the present disclosure will now be described to provide an overall understanding of the principles of the structure, function, manufacture, and use of the absorbent articles having shaped, soft and textured nonwoven fabrics disclosed herein. One or more examples of these non-limiting forms are illustrated in the accompanying drawings. Those of ordinary skill in the art will understand that the absorbent articles having shaped, soft and textured nonwoven fabrics described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

The present disclosure provides shaped, soft and textured nonwoven fabrics directly formed on a shaped forming belt with continuous spunbond filaments in a single forming process. The nonwoven fabric of the present disclosure may assume a shape which corresponds to the shape of the forming belt. The nonwoven fabrics of the present disclosure resolve the contradiction between softness and texture and provide high texture while still providing high softness.

Figure 1:
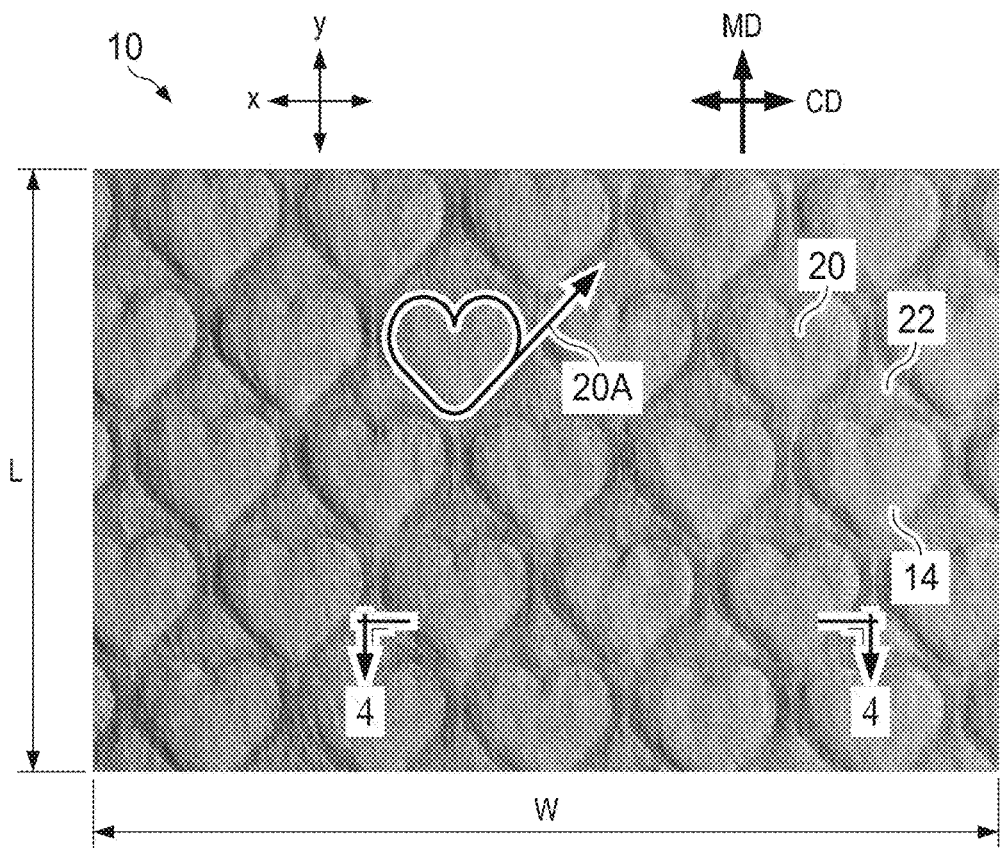
FIG. 1 is a photograph of an example nonwoven fabric of the present disclosure.
Figure 2:
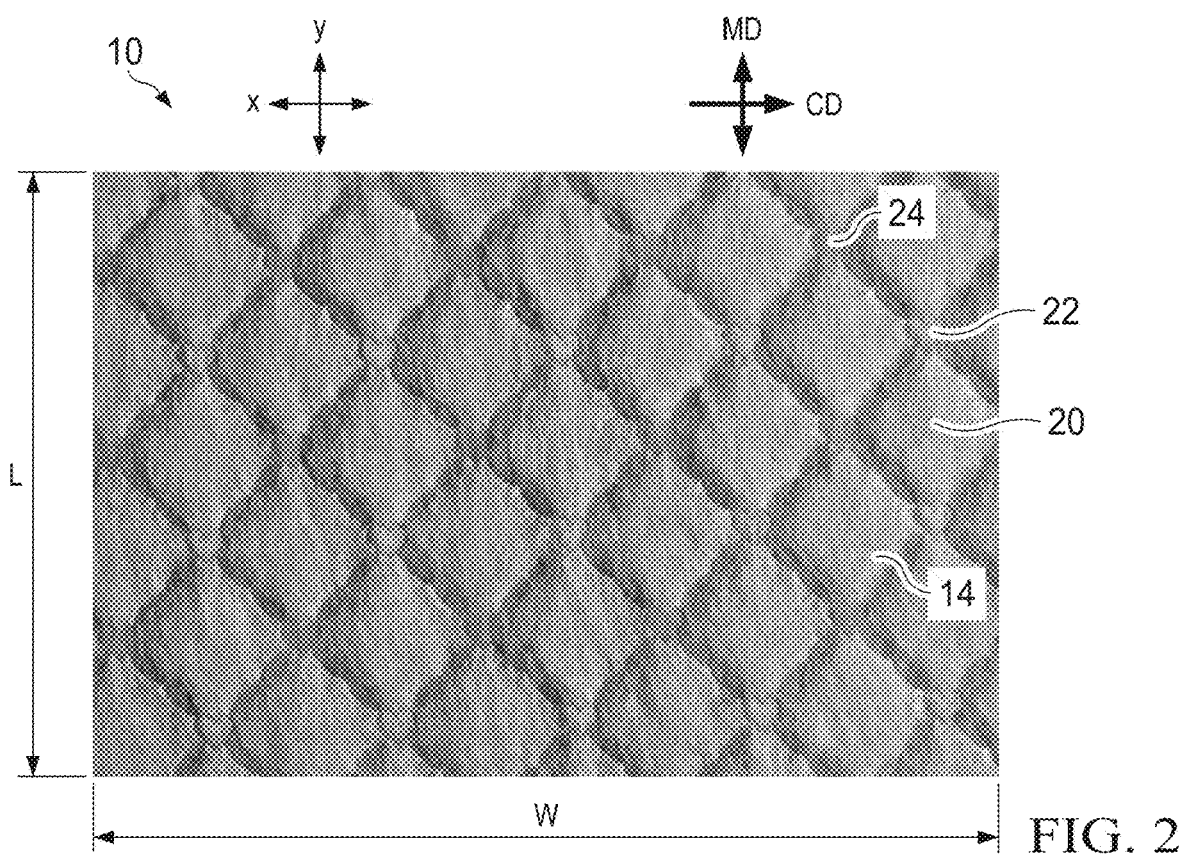
FIG. 2 is a photograph of an example nonwoven fabric of the present disclosure.
Figure 3:
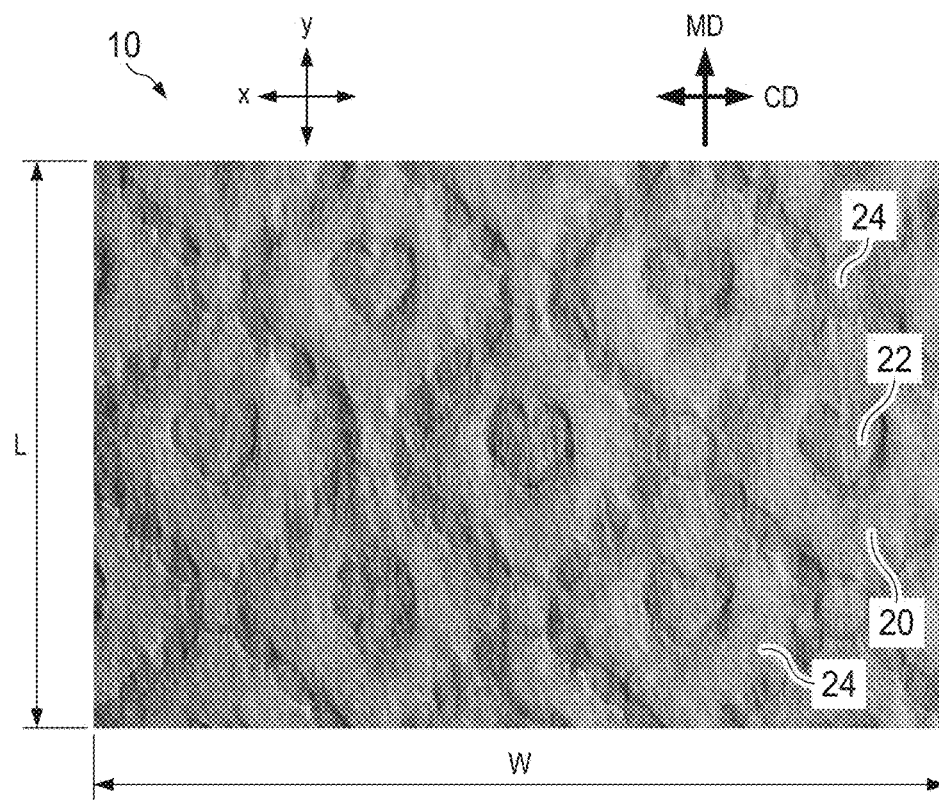
FIG. 3 is a photograph of an example nonwoven fabric of the present disclosure.

Photographs of representative examples of shaped nonwoven fabrics 10 are shown in FIGS. 1-3. The shaped nonwoven fabrics may be used as topsheets and/or outer cover nonwoven materials, for example. The shaped nonwoven fabrics may also be used as other nonwoven components of absorbent articles or in other consumer products, such as cleaning and dusting products and medical gowns, for example.

Figure 4:
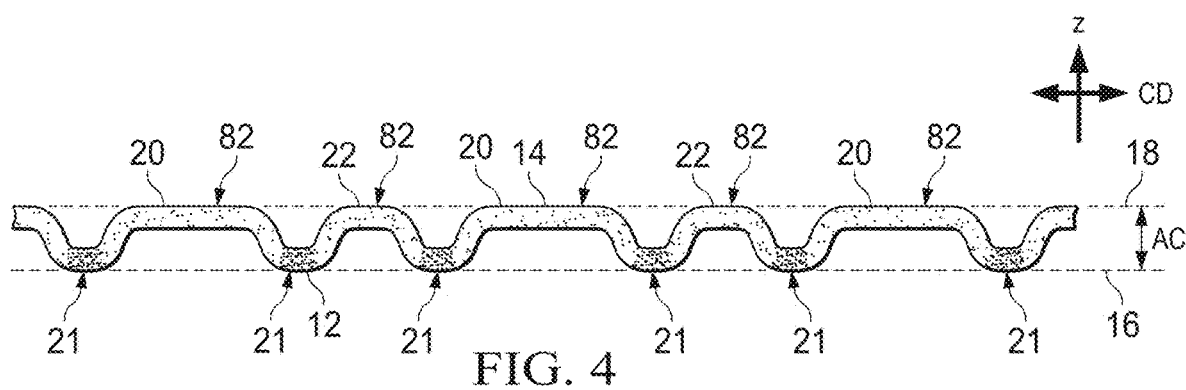
FIG. 4 is a cross-sectional illustration of a portion of the nonwoven fabric of the present disclosure, taken about line 4-4 of FIG. 1.

The shaped nonwoven fabric 10 may be a spunbond nonwoven substrate having a first surface 12 and a second surface 14. In FIGS. 1-3, second surface 14 is facing the viewer and is opposite the first surface 12, which is unseen in FIGS. 1-3 but is depicted in FIG. 4. The term "surface" is used broadly to refer to the two sides of a web for descriptive purposes, and is not intended to infer any necessary flatness or smoothness. Although the shaped nonwoven fabric 10 is soft and flexible, it will be described in a flattened condition the context of one or more X-Y planes parallel to the flattened condition, and which correspond in web-making technology to the plane of the cross-machine direction, CD, and machine direction, MD, respectively, as shown in FIGS. 1-3. The length, L, in the MD and the width, W, in the CD determine the overall area A for the nonwoven fabric 10. As shown in FIG. 4, which is a cross section of a portion of the nonwoven fabric 10 shown in FIG. 1, for descriptive purposes the three-dimensional features of the shaped nonwoven fabric are described as extending outwardly in a Z-direction from an X-Y plane of the first surface 16 (see, FIG. 4). A maximum dimension of three-dimensional features in the Z-direction may define the maximum distance between the plane of the first surface 16 and an X-Y plane of the second surface 18, which distance may be measured as the average caliper AC of the nonwoven fabric 10. The average caliper may be determined via optical, non-contact means, or it may be determined by instruments involving spaced apart flat plates that measure the caliper of the nonwoven placed between them under a predetermined pressure. It is not necessary that all the three-dimensional features have the same Z-direction maximum dimension, but a plurality of three-dimensional features may have substantially the same Z-direction maximum dimension determined by the fiber laydown process and the properties of the forming belt, discussed below.

The nonwoven fabrics shown in FIGS. 1-4 (as well as other nonwoven fabrics disclosed herein) may be fluid permeable. The entire nonwoven fabric may be considered fluid permeable. Regions or zones (described below) may be fluid permeable. By fluid permeable, as used herein, with respect to the nonwoven fabric is meant that the nonwoven fabric has at least one zone which permits liquid to pass through under in-use conditions of a consumer product. For example, if used as a topsheet on a disposable diaper, the nonwoven fabric may have at least one zone having a level of fluid permeability permitting urine to pass through to an underlying absorbent core. By fluid permeable as used herein with respect to a region is meant that the region exhibits a porous structure that permits liquid to pass through.

As shown in FIGS. 1-4, the nonwoven fabric 10 may have a regular, repeating pattern of a plurality of discrete, recognizably different three-dimensional features, including a first three-dimensional feature 20 and a second three-dimensional feature 22, and a third three-dimensional feature 24, as shown in FIGS. 2 and 3. For example, in FIG. 1, heart-shaped first three-dimensional feature 20 is recognizably different from the smaller, generally triangular-shaped second three-dimensional feature 22. The recognizable differences may be visual, such as recognizably different sizes and/or shapes.

The three-dimensional features of the nonwoven fabric 10 may be formed by depositing, such as by carding, air laying, spinning from solution, or melt spinning, fibers directly onto a forming belt having a pattern of corresponding three-dimensional features. In one sense, the nonwoven fabric 10 is molded onto a forming belt that determines the shapes of the three-dimensional features of the fabric 10. However, importantly, as described herein, the apparatus and method of the present disclosure produce the nonwoven fabric 10 such that in addition to taking the shape of the forming belt, because of the attributes of the forming belt and the apparatus for forming the fabric, it is imparted with beneficial properties for use in absorbent articles, garments, medical products, and cleaning products. Specifically, because of the nature of the forming belt and other apparatus elements, as described below, the three-dimensional features of the nonwoven fabric 10 have intensive properties that may differ between first and second regions within a microzone (described more fully below), or from feature to feature in ways that provide for beneficial properties of the nonwoven fabric 10 when used in personal care articles, garments, medical products, and cleaning products. For example, a first three-dimensional feature 20 may have a basis weight or density that is different from the basis weight or density of a second three-dimensional feature 22, and both may have a basis weight or density that is different from that of a third three-dimensional feature 24, providing for beneficial aesthetic and functional properties related to fluid acquisition, distribution and/or absorption in diapers or sanitary napkins.

The intensive property differential between the various three-dimensional features of nonwoven fabric 10 is believed to be due to the fiber distribution and compaction resulting from the apparatus and method described herein. The fiber distribution occurs during the fiber laydown process, as opposed to, for example, a post making process such as embossing processes. Because the fibers are free to move during a process such as a melt spinning process, with the movement determined by the nature of the features and air permeability of the forming belt and other processing parameters, the fibers are believed to be more stable and permanently formed in nonwoven fabric 10.

As can be seen in FIGS. 1-3 and as understood from the description herein, the distinct three-dimensional features may be bounded by visually discernible (with respect to the interior of a three-dimensional feature) regions that may be in the form of a closed figure (such as the heart shape in FIGS. 1 and 3, and the diamond shape of FIGS. 2 and 3). The closed figure may be a curvilinear closed figure, such as the heart shape in FIGS. 1 and 3. The outlining visually discernible regions may be the regions of the nonwoven fabric 10 that are most closely adjacent in the Z-direction to first surface 12, such as regions 21 as shown in FIG. 4, and with may lie at least partially in or on first plane 16 when in a flattened condition. For example, as shown in FIG. 1, first three-dimensional feature 20 is heart shaped, and as indicated as one example first three-dimensional feature 20A is defined by a curvilinear closed heart-shaped element. A curvilinear element can be understood as a linear element having at any point along its length a tangential vector V, with the closed shape being such that the tangential vector V has both MD and CD components that change values over greater than 50% of the length of the linear element of the closed figure. Of course, the figure need not be entirely 100% closed, but the linear element may have breaks that do not take away from the overall impression of a closed figure. As discussed below in the context of the forming belt, the outlining visually discernible curvilinear closed heart-shaped element is formed by a corresponding closed heart-shaped raised element on the forming belt to make the closed figure of a heart on fabric 10. In a repeating pattern, the individual shapes (in the case of first three-dimensional feature in FIG. 1, a heart shape) may result in aesthetically pleasing, soft, pillowy features across the overall area OA of the second surface 14 of fabric 10. When the nonwoven fabric 10 is meant to be used as a topsheet for a diaper or sanitary napkin, the second surface 14 of nonwoven fabric 10 may be wearer-facing to deliver superior aesthetic and performance benefits related to softness, compression resistance, and fluid absorption.

The present disclosure may utilize the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Melt spinning may occur at from about 150° C. to about 280° or at from about 190° to about 230°. Fiber spinning speeds may be greater than 100 meters/minute, and may be from about 1,000 to about 10,000 meters/minute, and may be from about 2,000 to about 7,000 meters/minute, and may be from about 2,500 to about 5,000 meters/minute. Spinning speeds may affect the brittleness of the spun fiber, and, in general, the higher the spinning speed, the less brittle the fiber. Continuous fibers may be produced through spunbond methods or meltblowing processes.

A nonwoven fabric 10 of the present disclosure may comprise continuous multicomponent polymeric filaments comprising a primary polymeric component and a secondary polymeric component. The filaments may be continuous bicomponent filaments comprising a primary polymeric component A and a secondary polymeric component B. The bicomponent filaments have a cross-section, a length, and a peripheral surface. The components A and B may be arranged in substantially distinct zones across the cross-section of the bicomponent filaments and may extend continuously along the length of the bicomponent filaments. The secondary component B constitutes at least a portion of the peripheral surface of the bicomponent filaments continuously along the length of the bicomponent filaments. The polymeric components A and B may be melt spun into multicomponent fibers on conventional melt spinning equipment. The equipment will be chosen based on the desired configuration of the multicomponent. Commercially available melt spinning equipment is available from Hills, Inc. located in Melbourne, Florida. The temperature for spinning range from about 180° C. to about 230° C. The bicomponent spunbond filaments may have an average diameter from about 6 to about 40 microns or from about 12 to about 40 microns.

Figure 5A:
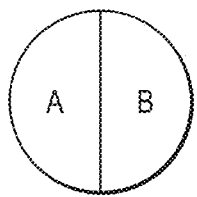
FIG. 5A is a schematic drawing illustrating a cross-section of a filament made with a primary component A and a secondary component B in a side-by-side arrangement.
Figure 5B:
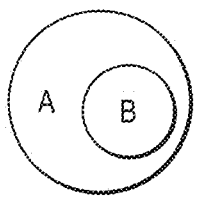
FIG. 5B is a schematic drawing illustrating a cross-section of a filament made with a primary component A and a secondary component B in an eccentric sheath/core arrangement.
Figure 5C:
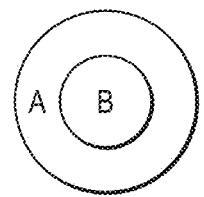
FIG. 5C is a schematic drawing illustrating a cross-section of a filament made with a primary component A and a secondary component B in a concentric sheath/core arrangement.
Figure 6:
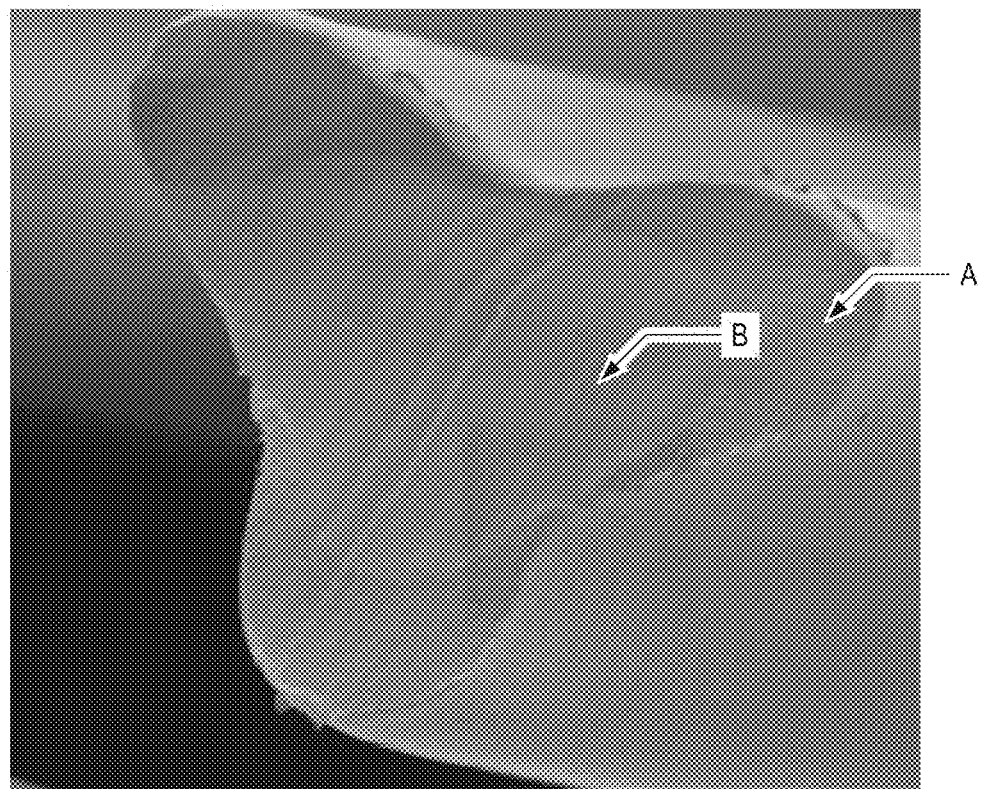
FIG. 6 is a perspective view photograph of a tri-lobal, bicomponent fiber.

The components A and B may be arranged in either a side-by-side arrangement as shown in FIG. 5A or an eccentric sheath/core arrangement as shown in FIG. 5B to obtain filaments which exhibit a natural helical crimp. Alternatively, the components A and B may be arranged in a concentric sheath core arrangement as shown in FIG. 5C. Additionally, the component A and B may be arranged in multi-lobal sheath core arrangement as shown in FIG. 6. Other multicomponent fibers may be produced by using the compositions and methods of the present disclosure. The bicomponent and multicomponent fibers may be segmented pie, ribbon, islands-in-the-sea configuration, or any combination thereof. The sheath may be continuous or non-continuous around the core. The fibers of the present disclosure may have different geometries that comprise round, elliptical, star shaped, rectangular, and other various eccentricities.

Methods for extruding multicomponent polymeric filaments into such arrangements are generally known to those of ordinary skill in the art.

A wide variety of polymers are suitable to practice the present disclosure comprising polyolefins (such as polyethylene, polypropylene and polybutylene), polyesters, polyamides, polyurethanes, elastomeric materials and the like. Examples of polymer materials that may be spun into filaments may comprise natural polymers.

Primary component A and secondary component B may be selected so that the resulting bicomponent filament is providing improved nonwoven bonding and substrate softness.

Primary polymer component A may have melting temperature which is lower than the melting temperature of secondary polymer component B.

Primary polymer component A may comprise polyethylene or random copolymer of propylene and ethylene. Secondary polymer component B may comprise polypropylene or random copolymer of propylene and ethylene. Polyethylenes comprise linear low density polyethylene and high density polyethylene. In addition, secondary polymer component B may comprise additives for enhancing the natural helical crimp of the filaments, lowering the bonding temperature of the filaments, and enhancing the abrasion resistance, strength and softness of the resulting fabric.

Inorganic fillers, such as the oxides of magnesium, aluminum, silicon, and titanium, for example, may be added as inexpensive fillers or processing aides.

The filaments of the present invention may also comprise a slip additive in an amount sufficient to impart the desired haptics to the fiber. As used herein "slip additive" or "slip agent" means an external lubricant. The slip agent when melt-blended with the resin gradually exudes or migrates to the surface during cooling or after fabrication, hence forming a uniform, invisibly thin coating thereby yielding permanent lubricating effects. The slip agent may be a fast bloom slip agent.

During the making or in a post-treatment or even in both, the nonwoven fabrics of the present disclosure may be treated with surfactants or other agents to either hydrophilize the web or make it hydrophobic. For example, a nonwoven fabric used for a topsheet may be treated with a hydrophilizing material or surfactant so as to make it permeable to body exudates such as urine. For other absorbent articles, the topsheet may remain at its naturally hydrophobic state or made even more hydrophobic through the addition of a hydrophobizing material or surfactant.

Suitable materials for preparing the multicomponent filaments of the fabric of the present disclosure may comprise PP3155 polypropylene obtained from Exxon Mobil Corporation and PP3854 polypropylene obtained from Exxon Mobil Corporation.

When polypropylene is component A and the second polypropylene composition is component B, the side-by-side bicomponent filaments may comprise from about 5% to about 95% by weight polypropylene and from about 95% to about 5% of another polypropylene composition. The filaments may comprise from about 30% to about 70% by weight polyethylene and from about 70% to about 30% by weight of each component.

Figure 7:
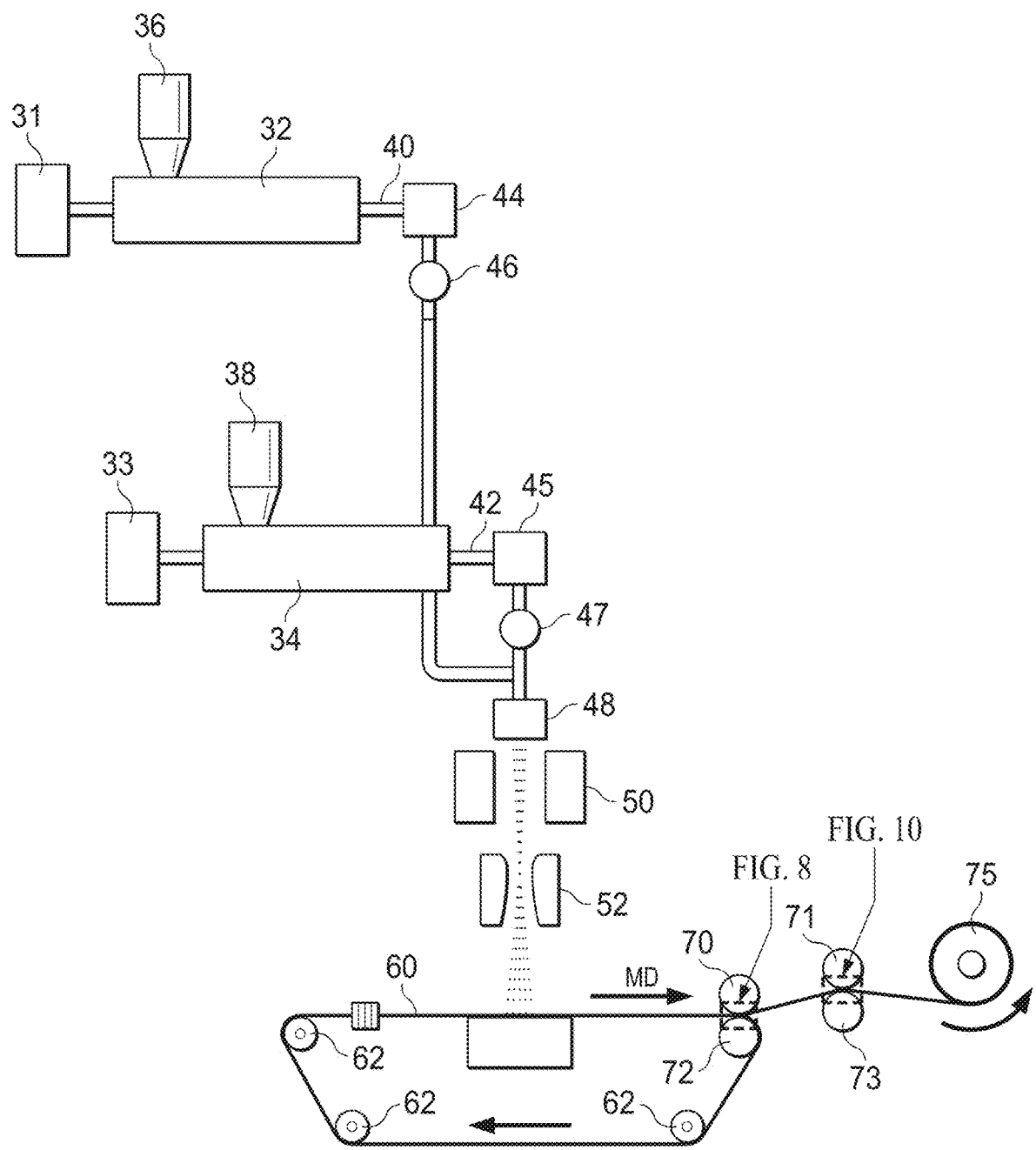
FIG. 7 is a schematic representation of an example apparatus for making a nonwoven fabric of the present disclosure.

Turning to FIG. 7, a representative process line 30 for preparing fabrics 10 of the present disclosure is disclosed. The process line 30 is arranged to produce a fabric of bicomponent continuous filaments, but it should be understood that the present disclosure comprehends nonwoven fabrics made with monocomponent or multicomponent filaments having more than two components. Bicomponent filaments may be trilobal.

The process line 30 includes a pair of extruders 32 and 34 driven by extruder drives 31 and 33, respectively, for separately extruding the primary polymer component A and the secondary polymer component B. Polymer component A is fed into the respective extruder 32 from a first hopper 36 and polymer component B is fed into the respective extruder 34 from a second hopper 38. Polymer components A and B may be fed from the extruders 32 and 34 through respective polymer conduits 40 and 42 to filters 44 and 45 and melt pumps 46 and 47, which pump the polymer into a spin pack 48. Spinnerets for extruding bicomponent filaments are generally known to those of ordinary skill in the art and thus are not described here in detail.

Generally described, the spin pack 48 comprises a housing which comprises a plurality of plates stacked one on top of the other with a pattern of openings arranged to create flow paths for directing polymer components A and B separately through the spinneret. The spin pack 48 has openings arranged in one or more rows. The spinneret openings form a downwardly extending curtain of filaments when the polymers are extruded through the spinneret. For the purposes of the present disclosure, spinnerets may be arranged to form sheath/core or side-by-side bicomponent filaments illustrated in FIGS. 5A, 5B, and 5C, as well as non-round fibers, such as tri-lobal fibers as shown in FIG. 6. Moreover, the fibers may be monocomponent comprising one polymeric component such as polypropylene.

The process line 30 also comprises a quench blower 50 positioned adjacent the curtain of filaments extending from the spinneret. Air from the quench air blower 50 quenches the filaments extending from the spinneret. The quench air may be directed from one side of the filament curtain or both sides of the filament curtain.

An attenuator 52 is positioned below the spinneret and receives the quenched filaments. Fiber draw units or aspirators for use as attenuators in melt spinning polymers are generally known. Suitable fiber draw units for use in the process of the present disclosure comprise a linear fiber attenuator of the type shown in U.S. Pat. No. 3,802,817 and eductive guns of the type shown in U.S. Pat. Nos. 3,692,618 and 3,423,266.

Generally described, the attenuator 52 comprises an elongate vertical passage through which the filaments are drawn by aspirating air entering from the sides of the passage and flowing downwardly through the passage. A shaped, endless, at least partially foraminous, forming belt 60 is positioned below the attenuator 52 and receives the continuous filaments from the outlet opening of the attenuator 52. The forming belt 60 is a belt and travels around guide rollers 62. A vacuum 64 positioned below the forming belt 60 where the filaments are deposited draws the filaments against the forming surface. Although the forming belt 60 is shown as a belt in FIG. 8, it should be understood that the forming belt may also be in other forms such as a drum. Details of particular shaped forming belts are explained below.

In operation of the process line 30, the hoppers 36 and 38 are filled with the respective polymer components A and B. Polymer components A and B are melted and extruded by the respective extruders 32 and 34 through polymer conduits 40 and 42 and the spin pack 48. Although the temperatures of the molten polymers vary depending on the polymers used, when polyethylenes are used as primary component A and secondary component B respectively, the temperatures of the polymers may range from about 190° C. to about 240° C.

As the extruded filaments extend below the spinneret, a stream of air from the quench blower 50 at least partially quenches the filaments, and, for certain filaments, to induce crystallization of molten filaments. The quench air may flow in a direction substantially perpendicular to the length of the filaments at a temperature of about 0° C. to about 35° C. and a velocity from about 100 to about 400 feet per minute. The filaments may be quenched sufficiently before being collected on the forming belt 60 so that the filaments may be arranged by the forced air passing through the filaments and forming surface. Quenching the filaments reduces the tackiness of the filaments so that the filaments do not adhere to one another too tightly before being bonded and may be moved or arranged on the forming belt during collection of the filaments on the forming belt and formation of the web.

After quenching, the filaments are drawn into the vertical passage of the attenuator 52 by a flow of the fiber draw unit. The attenuator is may be positioned 30 to 60 inches below the bottom of the spinneret.

The filaments may be deposited through the outlet opening of the attenuator 52 onto the shaped, traveling forming belt 60. As the filaments are contacting the forming surface of the forming belt 60, the vacuum 64 draws the air and filaments against the forming belt 60 to form a nonwoven web of continuous filaments which assumes a shape corresponding to the shape of the forming surface. As discussed above, because the filaments are quenched, the filaments are not too tacky and the vacuum may move or arrange the filaments on the forming belt 60 as the filaments are being collected on the forming belt 60 and formed into the fabric 10.

The process line 30 comprises one or more bonding devices such as the cylinder-shaped compaction rolls 70 and 72, which form a nip through which the fabric may be compacted (e.g., calendared) and which may be heated to bond fibers as well. One or both of compaction rolls 70, 72 may be heated to provide enhanced properties and benefits to the nonwoven fabric 10 by bonding portions of the nonwoven fabric. For example, it is believed that heating sufficient to provide thermal bonding improves the fabric's 10 tensile properties. The compaction rolls may be pair of smooth surface stainless steel rolls with independent heating controllers. The compaction rolls may be heated by electric elements or hot oil circulation.

The gap between the compaction rolls may be hydraulically controlled to impose desired pressure on the fabric as it passes through the compaction rolls on the forming belt. As an example, with a forming belt caliper of 1.4 mm, and a spunbond nonwoven fabric having a basis weight of 25 gsm, the nip gap between the compaction rolls 70 and 72 may be about 1.4 mm.

Figure 8:
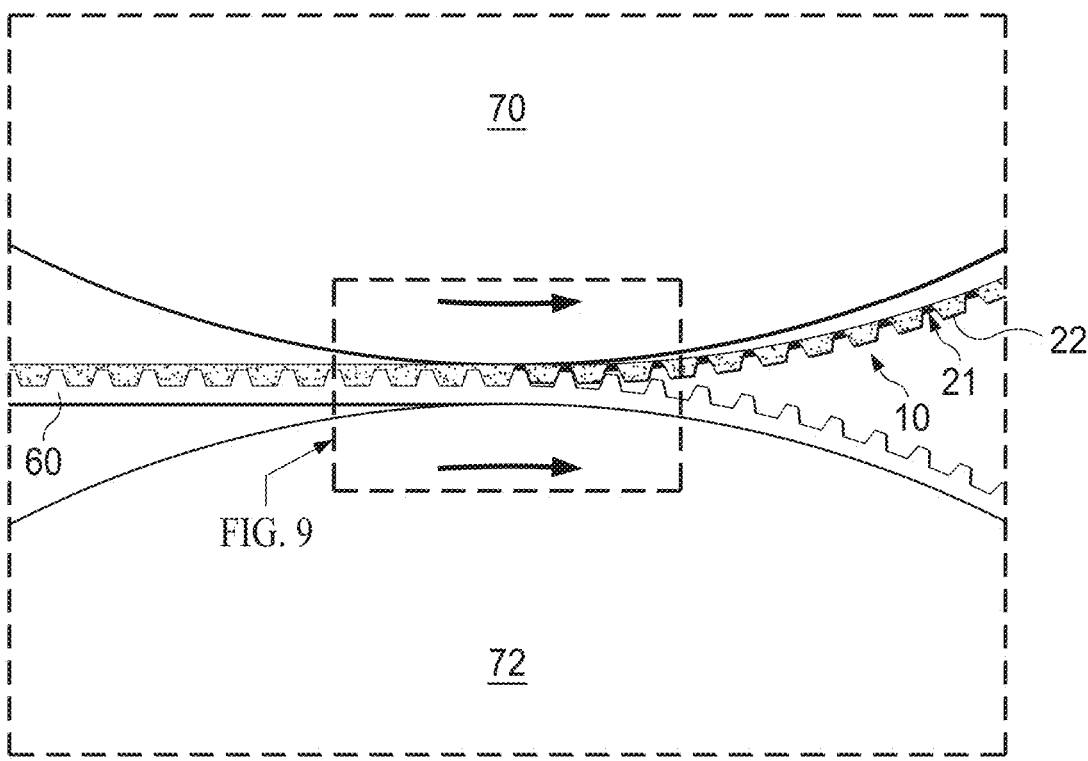
FIG. 8 is a detail of a portion of the apparatus of FIG. 7 for bonding a portion of a fabric of the present disclosure.
Figure 9:
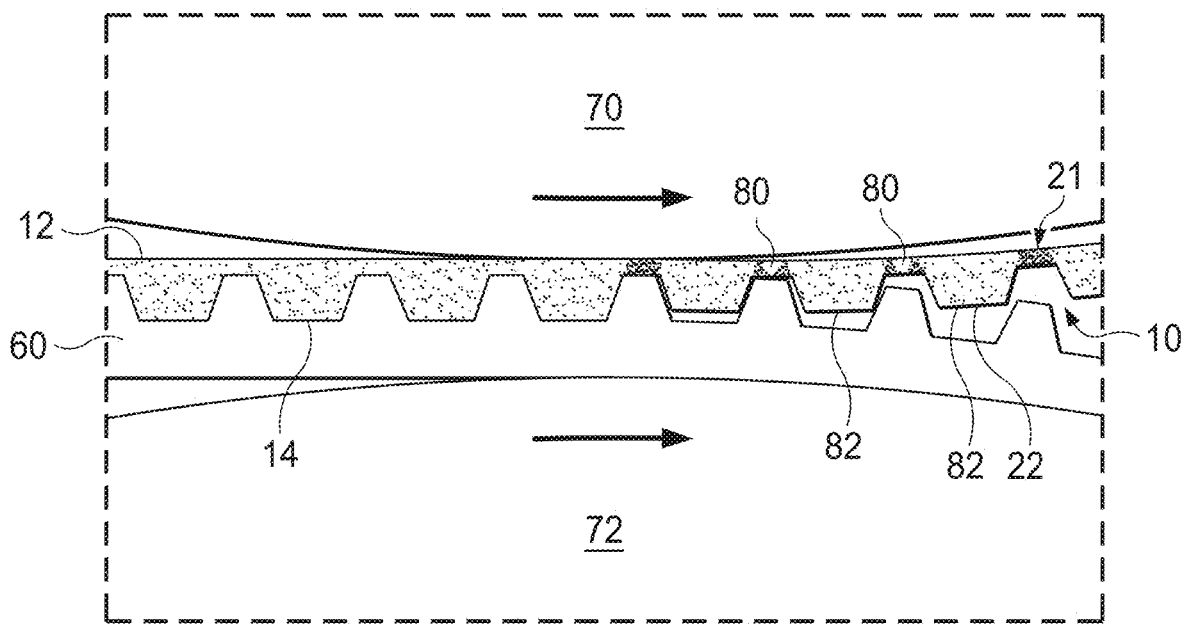
FIG. 9 is a further detail of a portion of the apparatus for bonding a portion of a fabric of the present disclosure, taken from detail FIG. 9 in FIG. 8.
Figure 11:
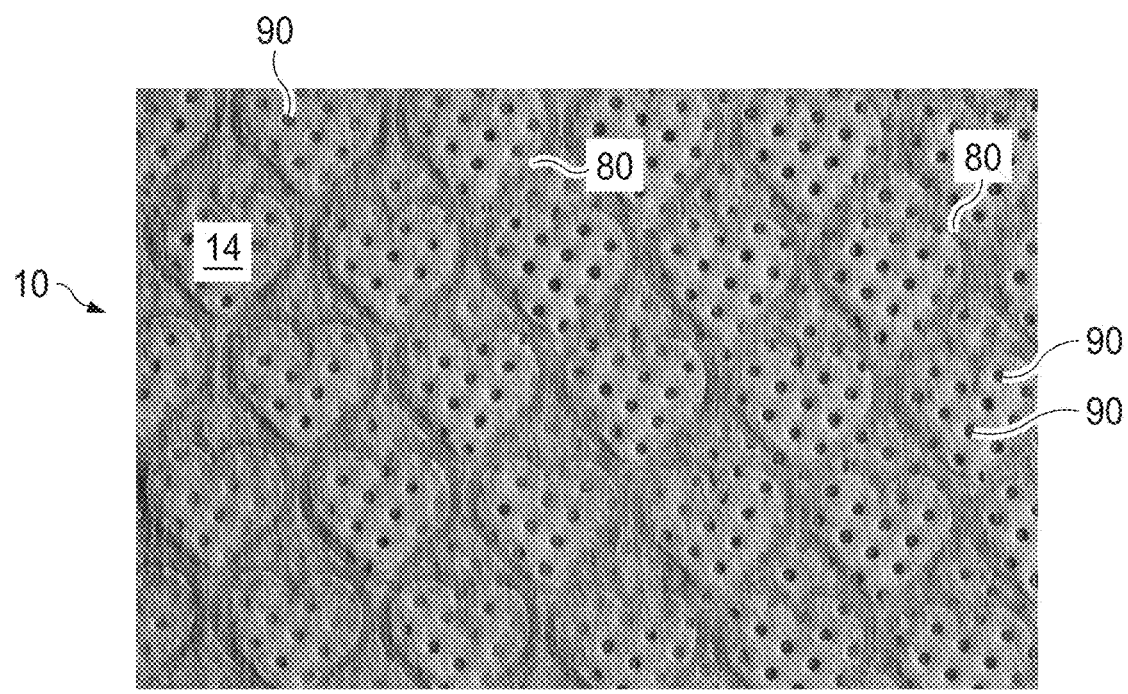
FIG. 11 is a photograph of an example nonwoven fabric of the present disclosure.

An upper compaction roll 70 may be heated sufficiently to melt bond fibers on the first surface 12 of the nonwoven fabric 10, to impart strength to the nonwoven fabric so that it may be removed from forming belt 60 without losing integrity. As shown in FIGS. 8 and 9, for example, as rolls 70 and 72 rotate in the direction indicated by the arrows, belt 60 with the spunbond fabric laid down on it enter the nip formed by rolls 70 and 72. Heated roll 70 may heat the portions of nonwoven fabric 10 that are pressed against it by the raised resin elements of belt 60, i.e., in regions 21, to create bonded fibers 80 on at least first surface 12 of fabric 10. As can be understood by the description herein, the bonded regions so formed may take the pattern of the raised elements of forming belt 60. For example, the bonded areas so formed may be a substantially continuous network or a substantially semi-continuous network on first surface 12 of regions 21 that make the same pattern as the hearts of FIG. 1 and FIG. 11. By adjusting temperature and dwell time, the bonding may be limited primarily to fibers closest to first surface 12, or thermal bonding may be achieved to second surface 14 as shown in FIG. 11 (which also shows point bonds 90, discussed more fully below), and FIGS. 34-38. Bonding may also be a discontinuous network, for example, as point bonds 90, discussed below.

The raised elements of the forming belt 60 may be selected to establish various network characteristics of the forming belt and the bonded regions of the nonwoven substrate 11 or nonwoven fabric 10. The network corresponds to the resin making up the raised elements of the forming belt 60 and may comprise substantially continuous, substantially semi-continuous, discontinuous, or combinations thereof options. These networks may be descriptive of the raised elements of the forming belt 60 as it pertains to their appearance or make-up in the X-Y planes of the forming belt 60 or the three dimensional features comprising the nonwoven substrate 11 or nonwoven fabric 10 of the present disclosure.

"Substantially continuous" network refers to an area within which one may connect any two points by an uninterrupted line running entirely within that area throughout the line's length. That is, the substantially continuous network has a substantial "continuity" in all directions parallel to the first plane and is terminated only at edges of that region. The term "substantially," in conjunction with continuous, is intended to indicate that while an absolute continuity may be achieved, minor deviations from the absolute continuity may be tolerable as long as those deviations do not appreciably affect the performance of the fibrous structure (or a molding member) as designed and intended.

"Substantially semi-continuous" network refers an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous structure.

"Discontinuous" network refer to discrete, and separated from one another areas that are discontinuous in all directions parallel to the first plane.

Figure 10:
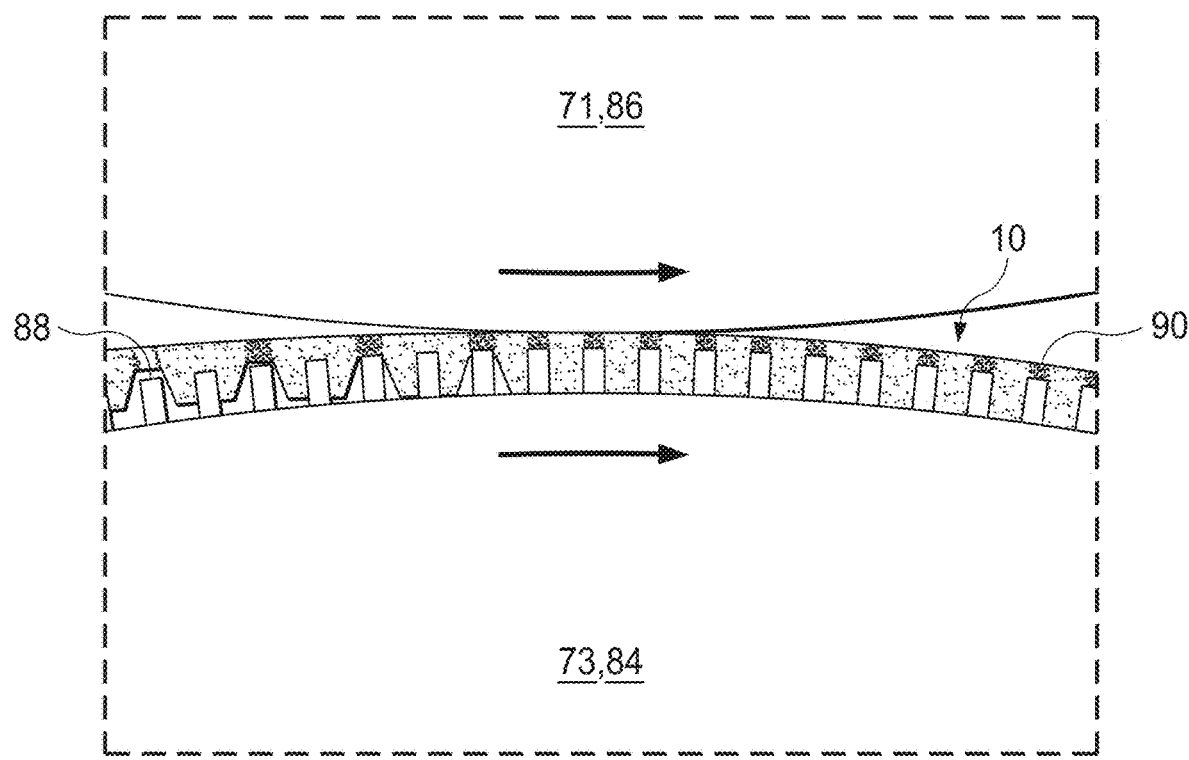
FIG. 10 is a detail of a portion of the apparatus for optional additional bonding of a portion of a nonwoven fabric of the present disclosure.

After compaction, the nonwoven fabric 10 may leave the forming belt 60 and be calendared through a nip formed by calendar rolls 71, 73, after which the fabric 10 may be wound onto a reel 75. As shown in the schematic cross section of FIG. 10, the calendar rolls 71, 73 may be stainless steel rolls having an engraved pattern roll 84 and a smooth roll 86. The engraved roll may have raised portions 88 that may provide for additional compaction and bonding to the fabric 10. Raised portions 88 may be a regular pattern of relatively small spaced apart "pins" that form a pattern of relatively small point bonds 90 in the nip of calendar rolls 71 and 73. The percent of point bonds in the nonwoven fabric 10 may be from about 3% to about 30% or from about 7% to about 20%. The engraved pattern may be a plurality of closely spaced, regular, generally cylindrically-shaped, generally flat-topped pin shapes, with pin heights being in a range of about 0.5 mm to about 5 mm or from about 1 mm to about 3 mm. Pin bonding calendar rolls may form closely spaced, regular point bonds 90 in nonwoven fabric 10, as shown in FIG. 11. Further bonding may be by hot-air through bonding, for example.

"Point bonding", as used herein, is a method of thermally bonding a nonwoven fabric, web, or substrate. This method comprises passing a web through a nip between two rolls comprising a heated male patterned or engraved metal roll and a smooth or patterned metal roll. The male patterned roll may have a plurality of raised, generally cylindrical-shaped pins that produce circular point bonds. The smooth roll may or may not be heated, depending on the application. In a nonwoven production line, the nonwoven fabric, which could be a non-bonded fiber web, is fed into the calendar nip and the fiber temperature is raised to the point for fibers to thermally fuse with each other at the tips of engraved points and against the smooth roll. The heating time is typically in the order of milliseconds. The fabric properties are dependent on process settings such as roll temperatures, web line speeds, and nip pressures, all of which may be determined by the skilled person for the desired level of point bonding. Other types of point bonding known generally as hot calendar bonding may use different geometries for the bonds (other than circular shaped), such as oval, lines, circles, for example. In an example, the point bonding produces a pattern of point bonds being 0.5 mm diameter circles with 10% overall bonding area. Other bonding shapes may have raised pins having a longest dimension across the bonding surface of a pin of from about 0.1 mm to 2.0 mm and the overall bonding area ranges from about 5% to about 30%.

As shown in FIG. 11, a heated compaction roll 70 may form a bond pattern, which may be a substantially continuous network bond pattern 80 (e.g., interconnected heart shaped bonds) on the first surface 12 of the nonwoven fabric 10 (not shown in FIG. 11, as it faces away from the viewer), and the engraved calendar roll 73 may form relatively small point bonds 90 on second surface 14 of the fabric 10. The point bonds 90 may secure loose fibers that would otherwise be prone to fuzzing or pilling during use of the fabric 10. The advantage of the resulting structure of the nonwoven fabric 10 is most evident when used as a topsheet in an absorbent article, such as a diaper or a sanitary napkin, for example. In use, in an absorbent article, the first surface 12 of the nonwoven fabric 10 may be relatively flat (relative to second surface 14) and have a relatively large amount of bonding due to the heated compaction roll forming bonds 80 at the areas of the fabric pressed by the raised elements of the forming belt 60. This bonding gives the nonwoven fabric 10 structural integrity, but may be relatively stiff or rough to the skin of a user. Therefore, the first surface 12 of the nonwoven fabric 10 may be oriented in a diaper or sanitary napkin to face the interior of the article, i.e., away from the body of the wearer or garment-facing. Likewise, the second surface 14 may be wearer-facing in use, and in contact with the body. The relatively small point bonds 90 may be less likely to be perceived visually or tacitly by the user, and the relatively soft three-dimensional features may remain visually free of fuzzing and pilling while feeling soft to the body in use. Further bonding may be used instead of, or in addition to, the above mentioned bonding.

Forming belt 60 may be made according to the methods and processes described in U.S. Pat. No. 6,610,173, issued to Lindsay et al. on Aug. 26, 2003, or U.S. Pat. No. 5,514,523 issued to Trokhan et al. on May 7, 1996, or U.S. Pat. No. 6,398,910 issued to Burazin et al. on Jun. 4, 2002, or US Pub. No. 2013/0199741, published in the name of Stage et al. on Aug. 8, 2013, each with the improved features and patterns disclosed herein for making spunbond nonwoven webs. The Lindsay, Trokhan, Burazin and Stage disclosures describe belts that are representative of papermaking belts made with cured resin on a woven reinforcing member, which belts, with improvements, may be utilized in the present disclosure as described herein.

Figure 12:
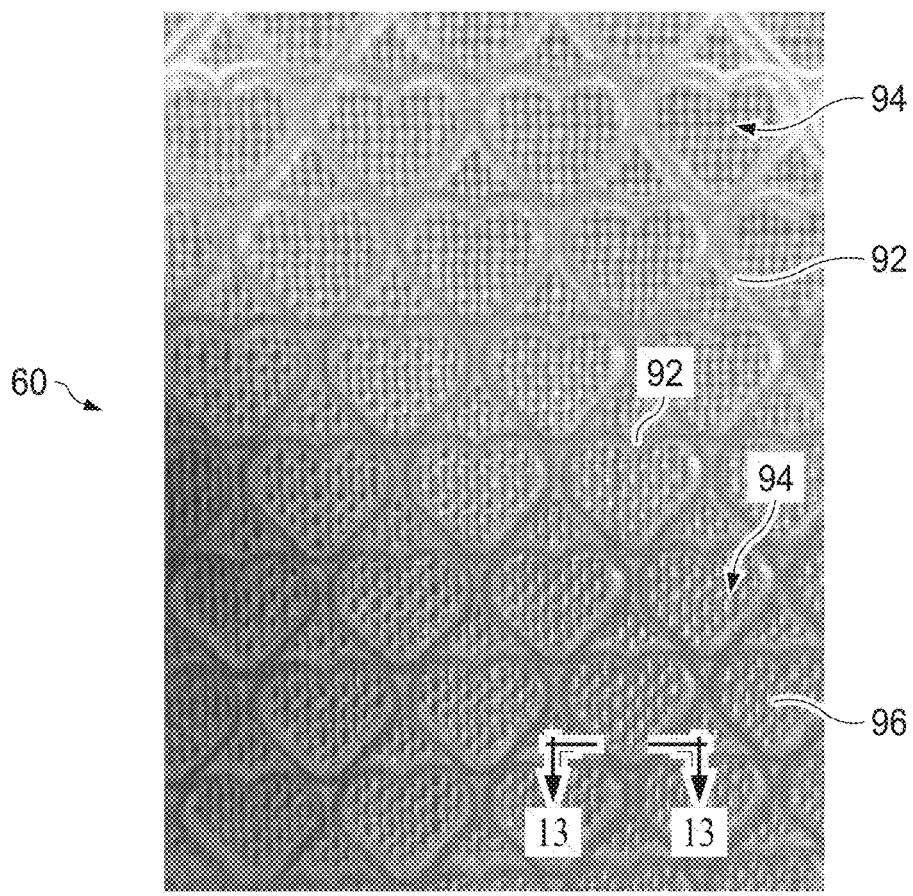
FIG. 12 is a photograph of a portion of a forming belt useful for forming a nonwoven fabric of the present disclosure.

An example of a forming belt 60 of the type useful in the present disclosure and which may be made according to the disclosure of U.S. Pat. No. 5,514,523, is shown in FIG. 12. As taught therein, a reinforcing member 94 (such as a woven belt of filaments 96) is thoroughly coated with a liquid photosensitive polymeric resin to a preselected thickness. A film or negative mask incorporating the desired raised element pattern repeating elements (e.g., FIG. 14) is juxtaposed on the liquid photosensitive resin. The resin is then exposed to light of an appropriate wave length through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 92 shown in FIG. 12. Other patterns may also be formed.

Figure 13:
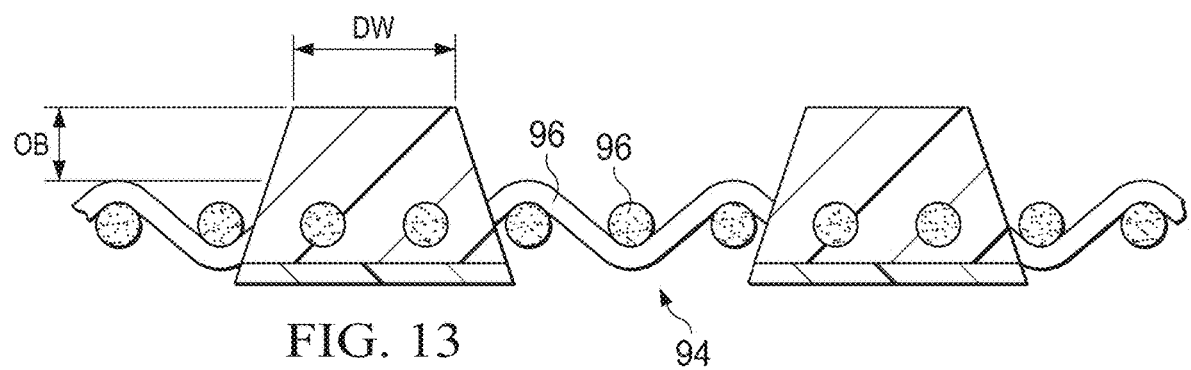
FIG. 13 is a cross-sectional depiction of a portion of the forming belt of FIG. 12.
Figure 14:
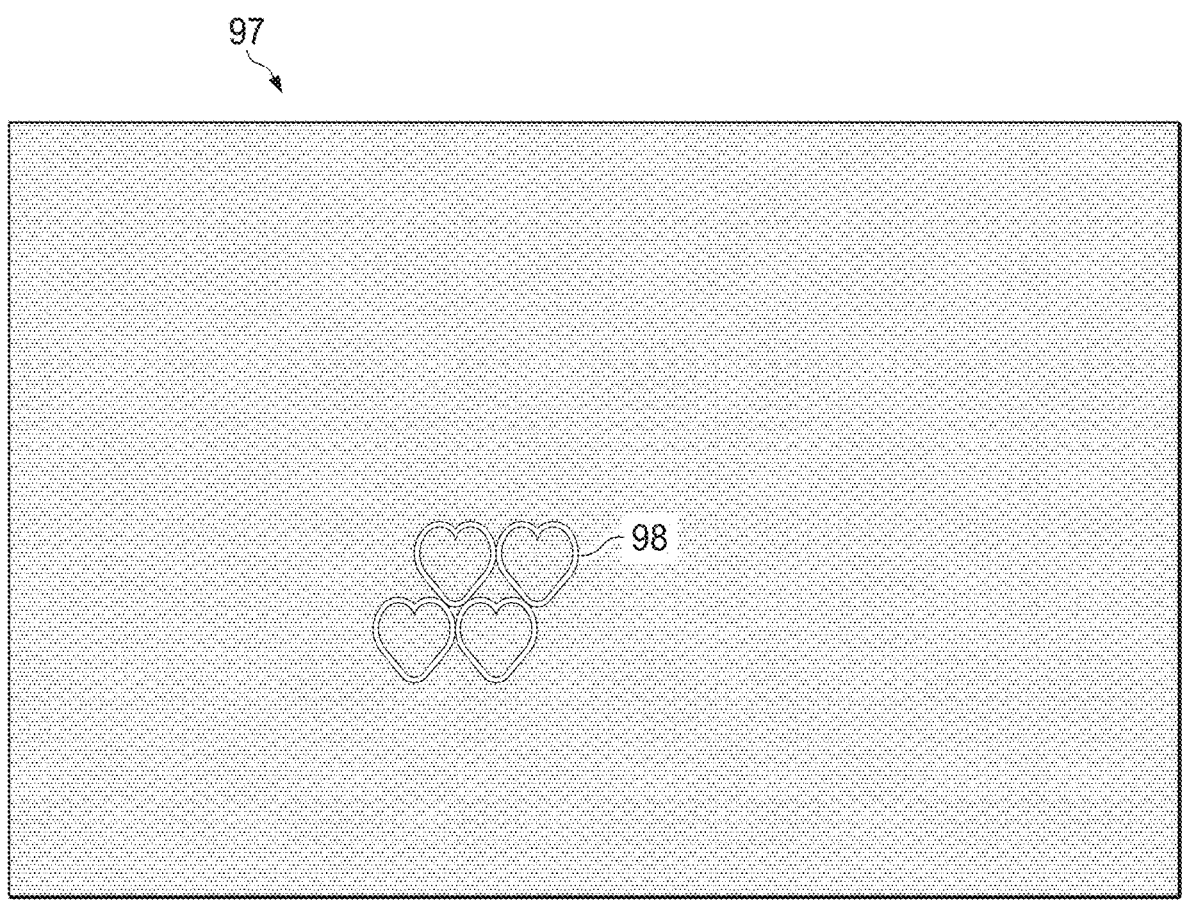
FIG. 14 is an image of a portion of a mask utilized to at least in part create the forming belt of FIG. 12.

FIG. 12 shows a portion of a forming belt 60 useful for making the nonwoven fabric 10 shown in FIG. 1. As shown, the forming belt 60 may comprise cured resin elements 92 on a woven reinforcing member 94. The reinforcing member 94 may be made of woven filaments 96 as is generally known in the art of papermaking belts, including resin coated papermaking belts. The cured resin elements may have the general structure depicted in FIG. 12, and are made by the use of a mask 97 having the dimensions indicated in FIG. 14. As shown in schematic cross-section in FIG. 13, cured resin elements 92 flow around and are cured to "lock on" to the reinforcing member 94 and may have a width at a distal end DW of about 0.020 inch to about 0.060 inch, or from about 0.025 inch to about 0.030 inch, and a total height above the reinforcing member 94, referred to as over burden, OB, of about 0.030 inch to about 0.120 inch or about 0.50 inch to about 0.80 inch, or about 0.060 inch. FIG. 14 represents a portion of a mask 97 showing the design and representative dimensions for one repeat unit of the repeating hearts design in the nonwoven fabric 10 shown in FIG. 1. The white portion 98 is transparent to UV light, and in the process of making the belt, as described in U.S. Pat. No. 5,514,523, permits UV light to cure an underlying layer of resin which is cured to form the raised elements 92 on the reinforcing member 94. After the uncured resin is washed away, the forming belt 60 having a cured resin design as shown in FIG. 12 is produced by seaming the ends of a length of the belt, the length of which may be determined by the design of the apparatus, as depicted in FIG. 7.

Figure 15:
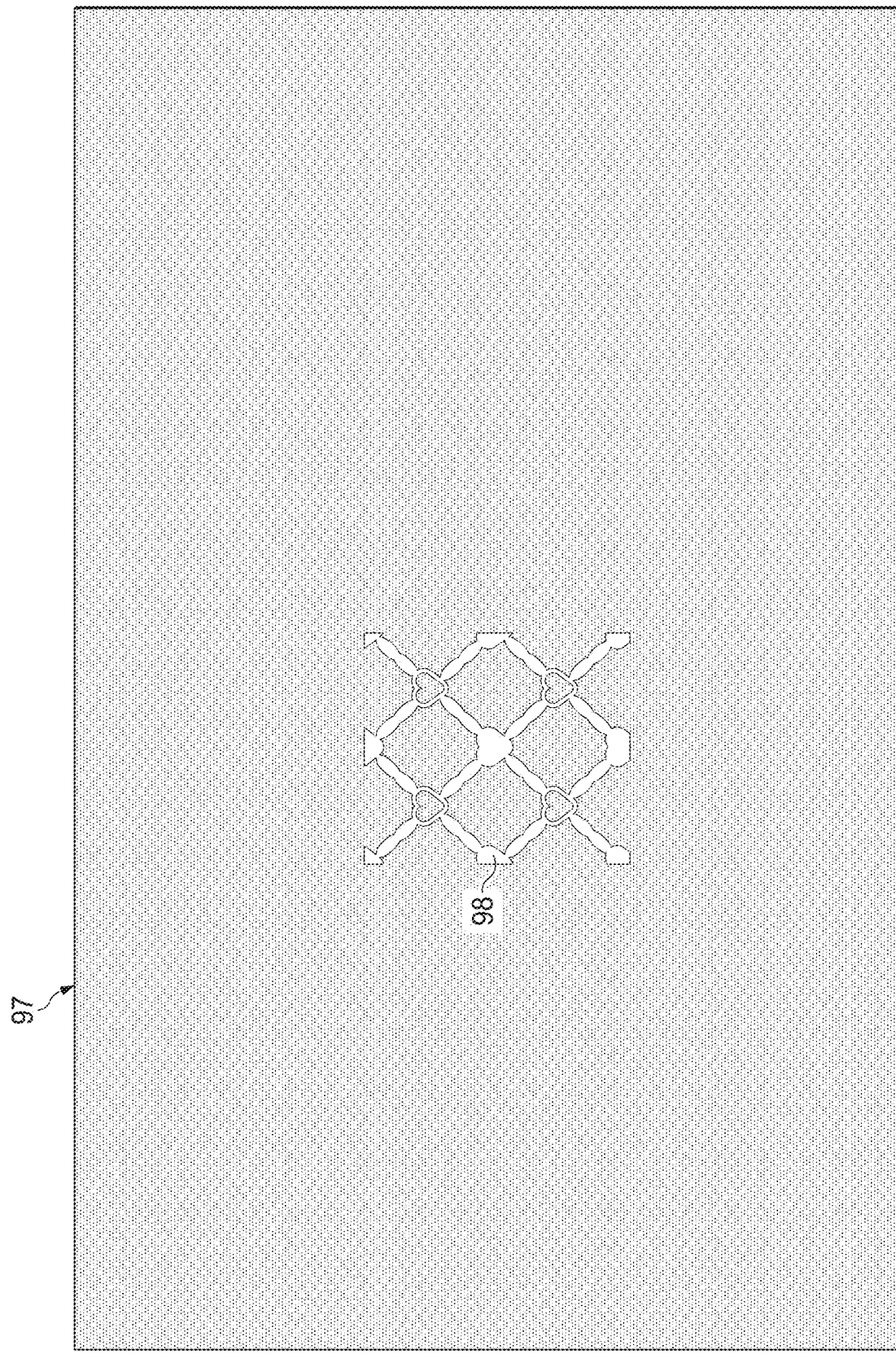
FIG. 15 is an image of a portion of a mask utilized to at least in part create the forming belt of FIG. 16.
Figure 16:
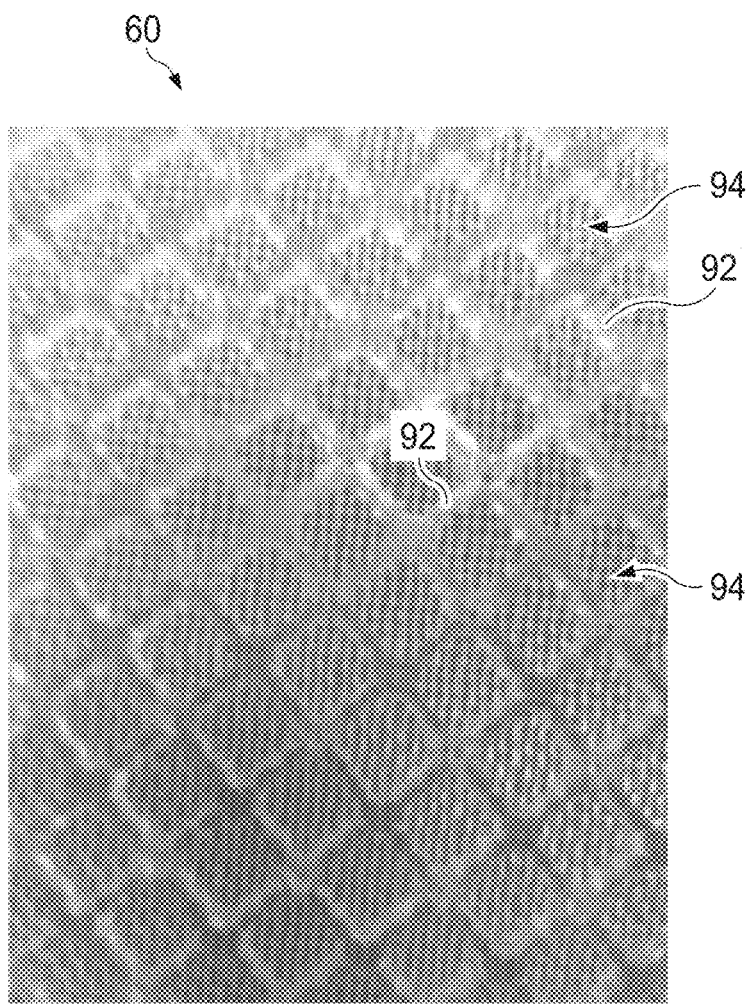
FIG. 16 is a photograph of a portion of a forming belt useful for forming a nonwoven fabric of the present disclosure.

In like manner, FIG. 15 represents a portion of a mask 97 showing the design for one repeat unit of the repeating design in the nonwoven fabric 10 shown in FIG. 2. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 16 is produced by seaming the ends of a length of the belt, the length of which may be determined by the design of the apparatus, as depicted in FIG. 7.

Figure 17:
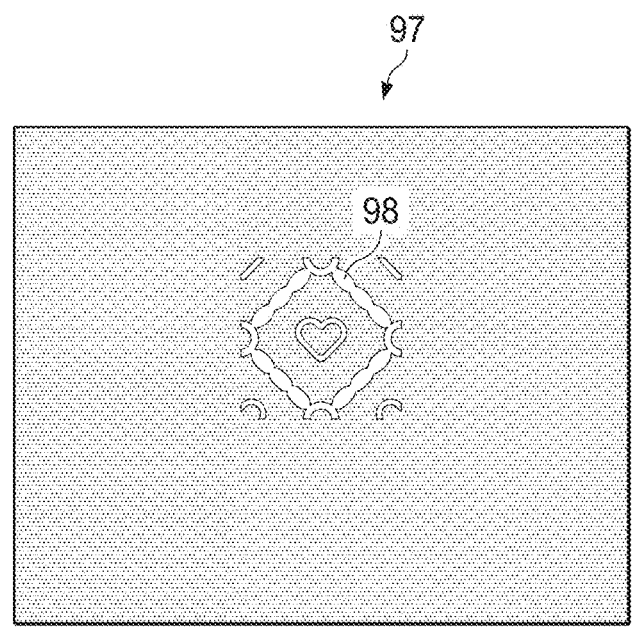
FIG. 17 is an image of a portion of a mask utilized to at least in part create the forming belt of FIG. 18.
Figure 18:
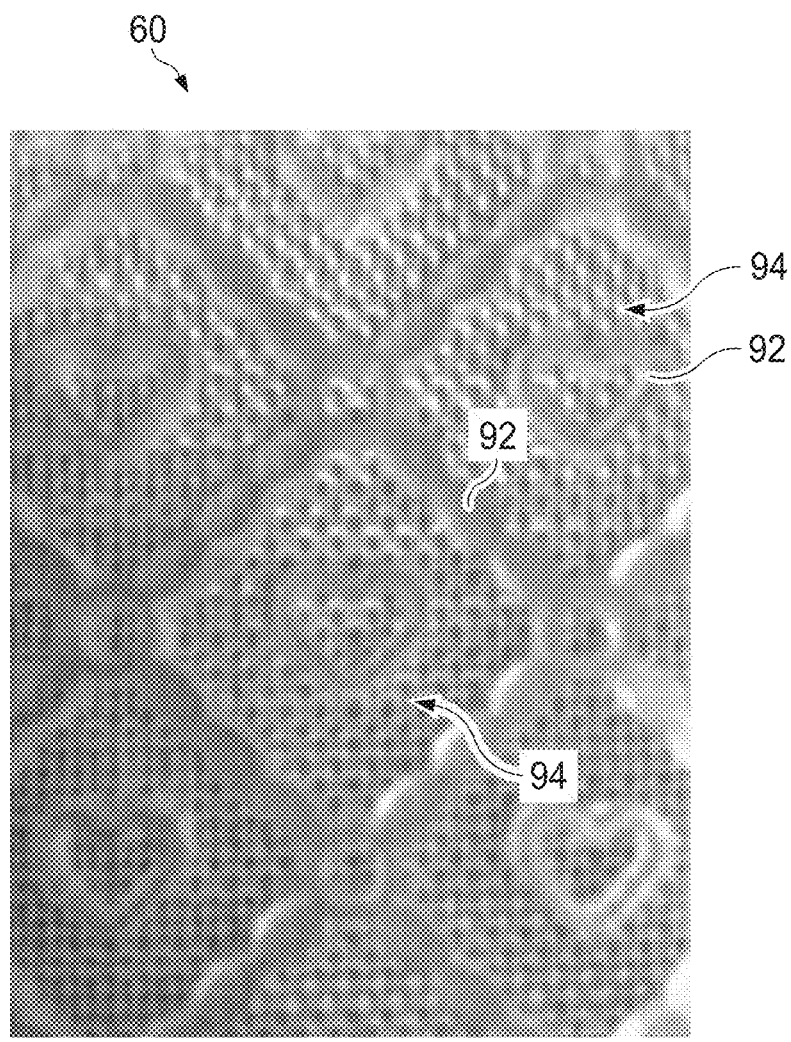
FIG. 18 is a photograph of a portion of a forming belt useful for forming a nonwoven fabric of the present disclosure.

Further, as an example, FIG. 17 represents a portion of a mask showing the design for one repeat unit of the repeating design in the nonwoven fabric 10 shown in FIG. 18. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 18 is produced by seaming the ends of a length of fabric 10.

Figure 19:
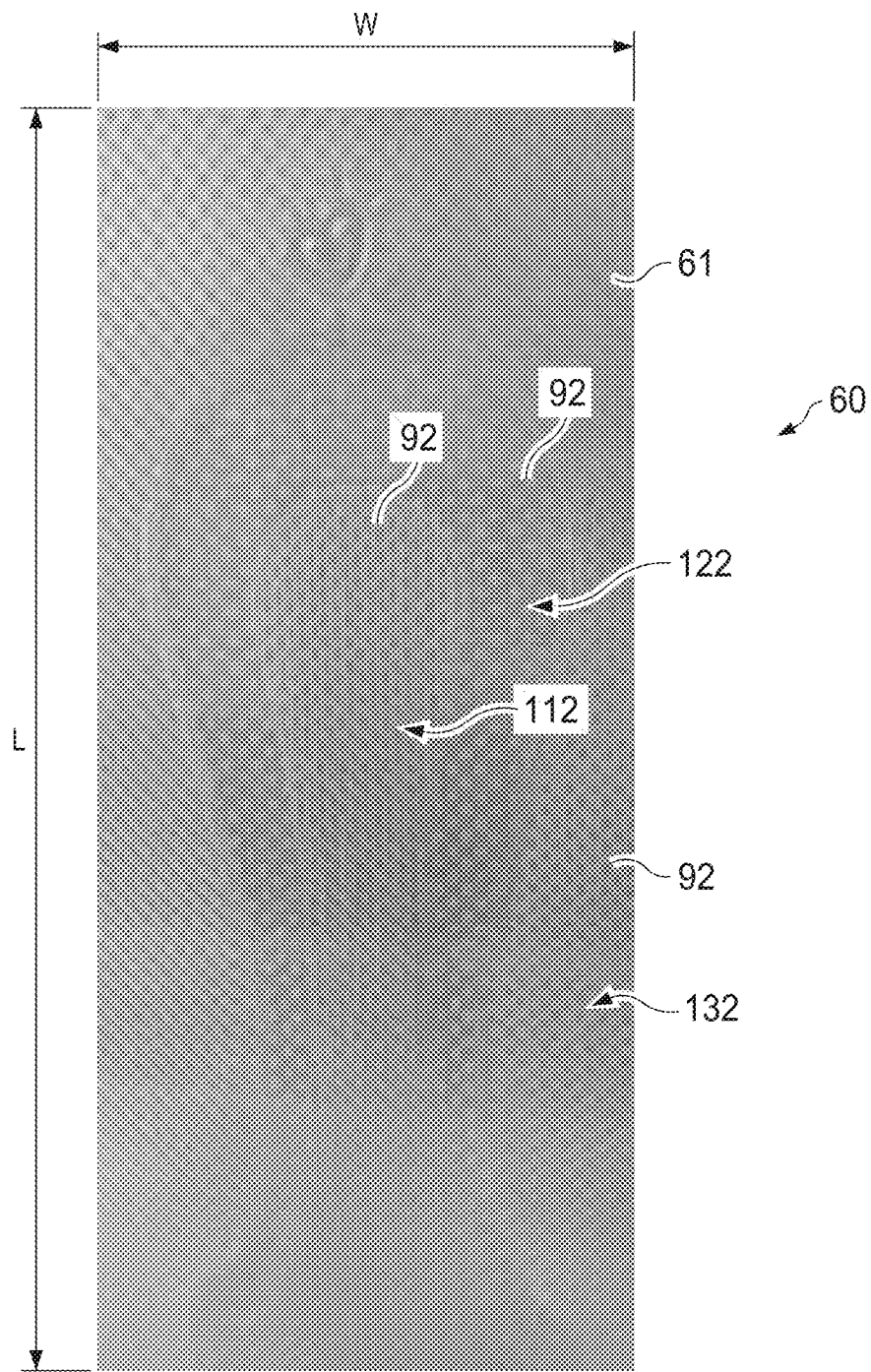
FIG. 19 is a photograph of a portion of a forming belt useful for forming a nonwoven fabric of the present disclosure.
Figure 20:
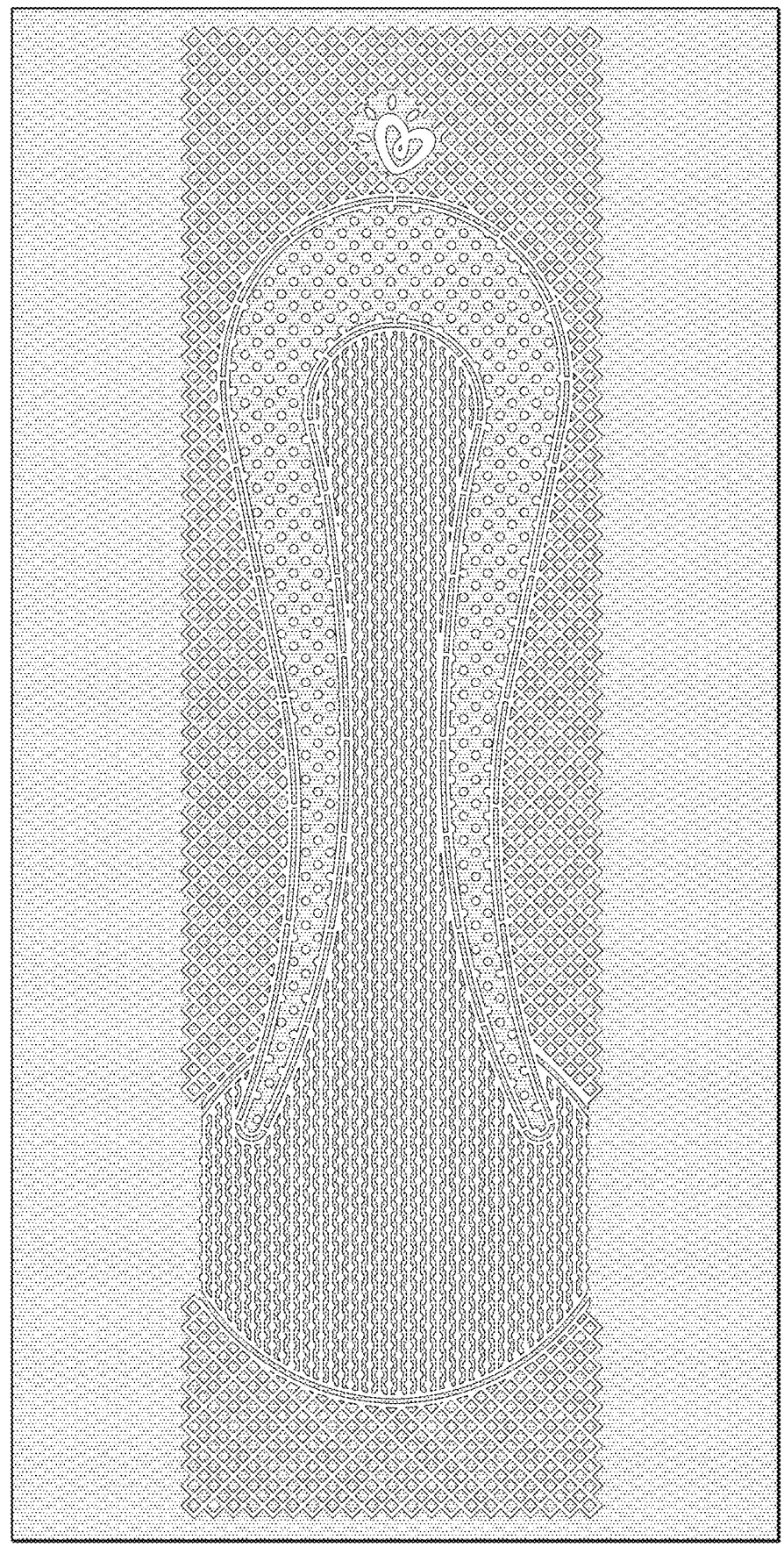
FIG. 20 an image of a mask utilized to at least in part create the forming belt of FIG. 19.

Another example of a portion of a forming belt 60 of the type useful in the present disclosure is shown in FIG. 19. The portion of the forming belt 60 shown in FIG. 19 is a discrete belt pattern 61 that may have a length L and width W corresponding to the length L and width W of the overall area OA of a nonwoven fabric 10. That is, the forming belt 60 may have discrete belt patterns 61 (as discussed more fully with reference to FIG. 22 below), each having a discrete belt pattern overall area DPOA that corresponds to the overall area OA of the nonwoven fabric 10. FIG. 20 represents a portion of a mask showing the design for one repeat unit of the repeating design in the nonwoven fabric 10 shown in FIG. 21. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 19 is produced by seaming the ends of a length of the belt.

The portion of the forming belt shown in FIG. 19 illustrates another benefit of the present disclosure. The portion of a forming belt 60 shown in FIG. 19 may make a fabric 10 shown in FIG. 21. The nonwoven fabric 10 shown in FIG. 21 may have width W and length L dimensions and an overall area OA making it suitable for use as a topsheet in a disposable diaper, for example. The nonwoven fabric 10 made on a forming belt 60 as shown in FIG. 19 differs from that shown in FIGS. 1-3 in that the pattern of three-dimensional features formed by the discrete resin elements 92 on forming belt 60 are not in a regular, repeating pattern across the entire overall area. Rather, the pattern of three-dimensional raised elements in the discrete belt pattern overall area DPOA may be described as an irregular pattern encompassing distinct portions referred to as zones. The distinction between zones may be visual, i.e., a visually discernible difference, or in the nonwoven fabric 10 the distinction may produce a difference in average intensive properties such as basis weight or density, or combinations of visual and intensive properties. A visually discernible difference exists if an observer in ordinary indoor lighting conditions (20/20 vision, lighting sufficient to read by, for example) may visually discern a pattern difference between the zones, such as the first zone 112 and the second zone 122.

Figure 21:
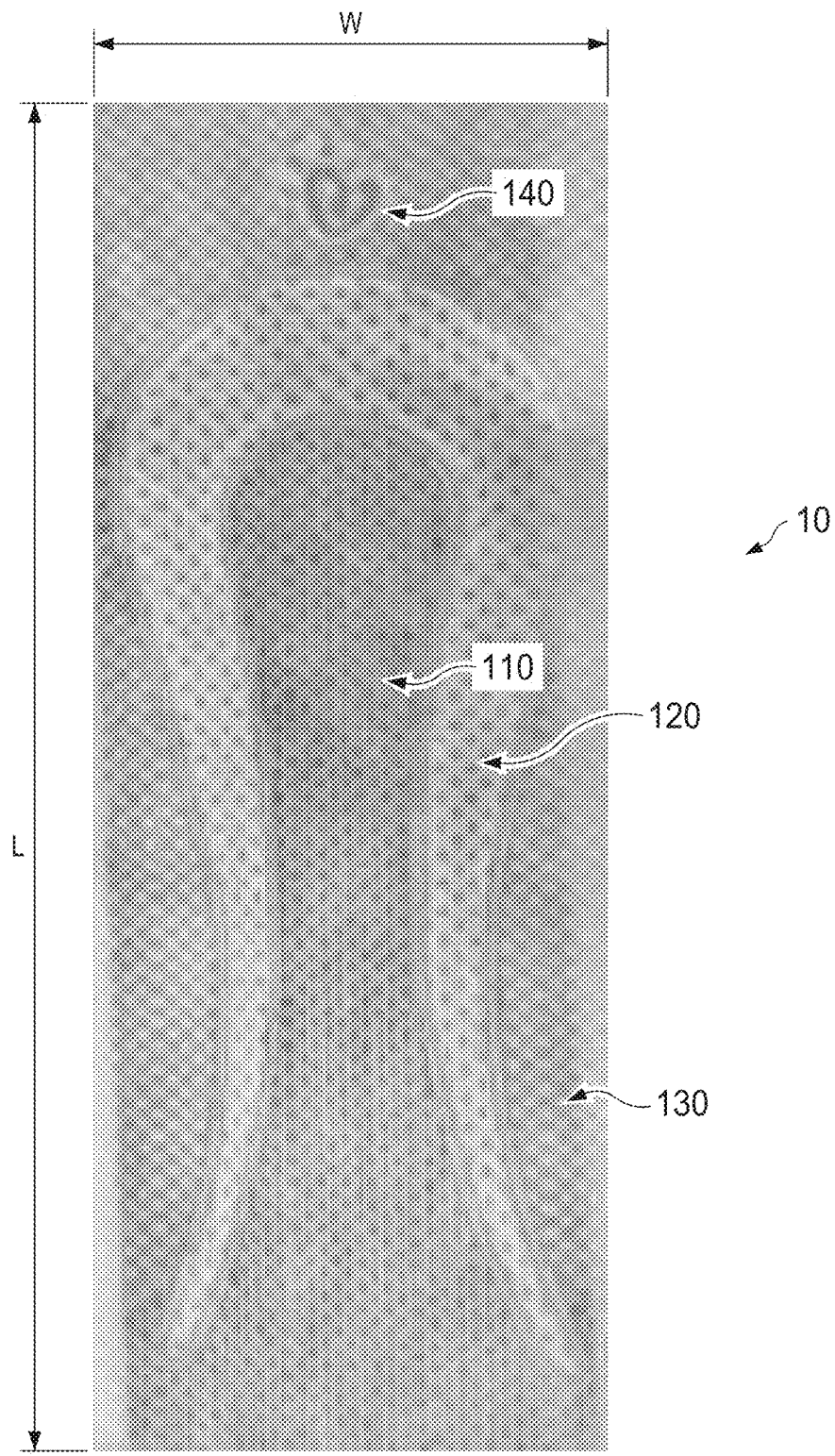
FIG. 21 is a photograph of a nonwoven fabric of the present disclosure made on the forming belt of FIG. 19.

The nonwoven fabric 10 may also have visually discernible zones corresponding to the zones of the forming belt. As shown in FIG. 21, for example, fabric 10 may have at least two, three, or four visually discernible zones. A first zone 110, having first pattern of three-dimensional features and first average intensive properties, may have a first area generally centrally located within the overall area OA. A second zone 120, having second pattern of three-dimensional features and second average intensive properties, may have a second area distributed generally about and completely surrounding, the first zone 110 within the overall area OA. A third zone 130, having third pattern of three-dimensional features and third average intensive properties, may have a third area distributed generally about and completely surrounding, the second zone 120 within the overall area OA. A fourth zone 140, having fourth three-dimensional features and fourth average intensive properties, may have a fourth area positioned within the overall area OA in any location, such as at a front area of a topsheet, such as the heart design shown in FIG. 21. In general, there may be n zones, with n being a positive integer. Each of the n zones may have an nth pattern of three-dimensional features and an nth area and nth average intensive properties.

The visually discernible zones as shown in FIG. 21 may comprise visually discernible three-dimensional features. These distinct three-dimensional features may be bounded by relatively higher density (with respect to the interior of a three-dimensional feature) regions that may be in the form of a closed figure, such as the heart shape in FIGS. 1 and 3, and the diamond shape of FIGS. 2 and 3. In general, as discussed more fully below, including in the context of micro zones, the three-dimensional features may be defined by a first region and a second region, wherein the first region and second region are visually distinct and there is a common intensive property associated with each of the first and second regions and there is a difference in the first region's and second region's common intensive property value. The three-dimensional features may be defined by a first region and a second region, with the first region being at a higher elevation (dimension measured in the Z-direction) than the second region with respect to the plane of the first surface. The three-dimensional features may be defined by a first region and a second region, with the first region being at a higher basis than the second region.

As can be understood, rather than having a constant repeating pattern that is uniform across the entire forming belt, the forming belt 60 of the present disclosure allows the production of a nonwoven material that may have repeats of irregular discrete belt patterns 61, each discrete belt pattern 61 being like the discrete belt pattern shown in FIG. 19. The discrete belt patterns 61 each may be used to form one nonwoven fabric 10 having an overall area OA suitable for use in a disposable absorbent article, such as diaper or sanitary napkin, for example. The nonwoven fabrics 10 may be produced sequentially, i.e., in line, and, optionally sequentially in parallel lanes, each lane being a sequential line of nonwoven fabrics 10. The sequential line of nonwoven fabrics 10 may be produced in a machine direction along an axis parallel to the machine direction. The nonwoven material may then be slit or otherwise cut to size to produce nonwoven fabrics 10 utilized as a topsheets in disposable absorbent articles.

The pattern within each discrete belt pattern overall area DPOA may be the same or different. That is, the sequentially spaced discrete belt patterns may be substantially identical, or they may differ in visual appearance and/or in the intensive properties produced in nonwoven substrates produced thereon. For example, as shown schematically in FIG. 22, the pattern of three-dimensional raised elements in first forming zone 112 of discrete belt pattern 61A may be different from the pattern of three-dimensional raised elements in first forming zone 112 of discrete belt pattern 61B. The forming belt 60 thus offers flexibility in producing nonwoven webs 10 suitable for use in consumer goods, including disposable absorbent articles.

Figure 22:
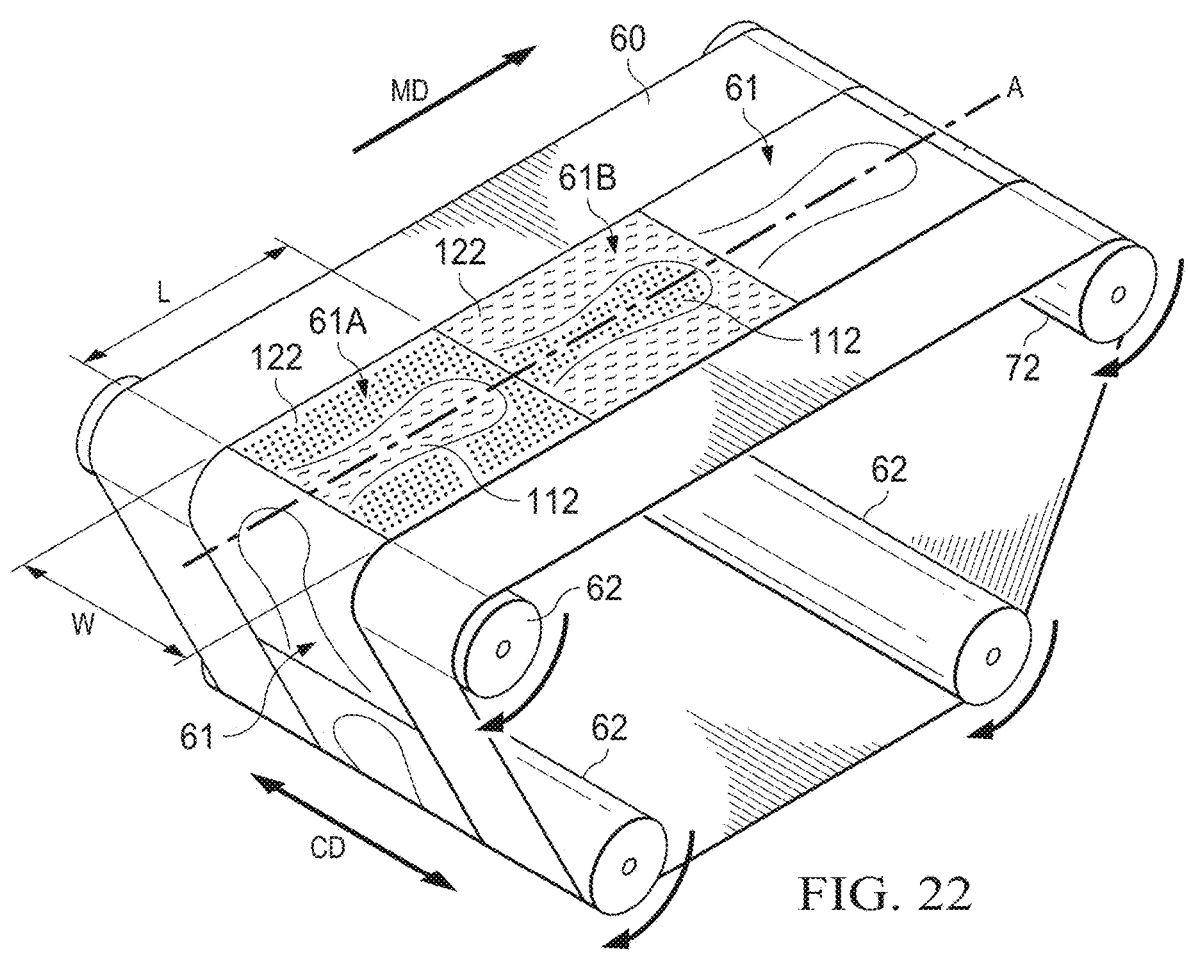
FIG. 22 is a perspective schematic view of a forming belt of the present disclosure.

Referring to FIG. 22, a forming belt having an axis A parallel to a longitudinal direction which is a machine direction is shown. The forming belt 60 may have a plurality of discrete belt patterns 61 ordered in at least one sequential relationship with respect to the longitudinal direction. Each discrete belt pattern 61 may have a discrete belt pattern overall area DPOA defined, in a rectangular-shaped pattern, by a length L and width W, as indicated with respect to discrete belt pattern 61A. Each discrete belt pattern within its overall area DPOA may have a first forming zone 112 having a first pattern of three-dimensional raised elements extending outwardly from the plane of the of the first surface and a second forming zone 122 having second three-dimensional raised elements extending outwardly from the plane of the of the first surface. The first forming zone may have a first air permeability value and the second forming zone may have a second air permeability value, and the first air permeability value may be different from the second air permeability value. The pattern within each sequentially ordered discrete belt pattern overall area DPOA may be the same or different.

By way of example, and referring to the discrete belt pattern 61 of forming belt 60 shown in FIG. 19, and the nonwoven fabric 10 shown in FIG. 21, the following properties were determined. A first zone 110 of the nonwoven fabric 10 may have an average basis weight of about 5 gsm to about 30 gsm; the second zone 120 may have an average basis weight of about 50 gsm to about 70 gsm; and the third zone 130 may have an average basis weight of about 25 gsm to about 60 gsm. The difference in basis weight from one zone to another may be attributed to a difference in air permeability of the forming belt 60. Referring to the nonwoven fabric 10 of FIG. 20, in which the basis weights for the zones 110, 120, and 130, are 15 gsm, 53 gsm and 25 gsm, respectively, the air permeability of the respective zones 112, 122, and 132 of the forming belt 60 are 379 cfm, 805 cfm, and 625 cfm, respectively. Thus, by varying air permeability in zones in forming belt 10, the intensive properties of average basis weight and average density in zones may be facilitated across the overall area of fabric 10.

Figure 23:
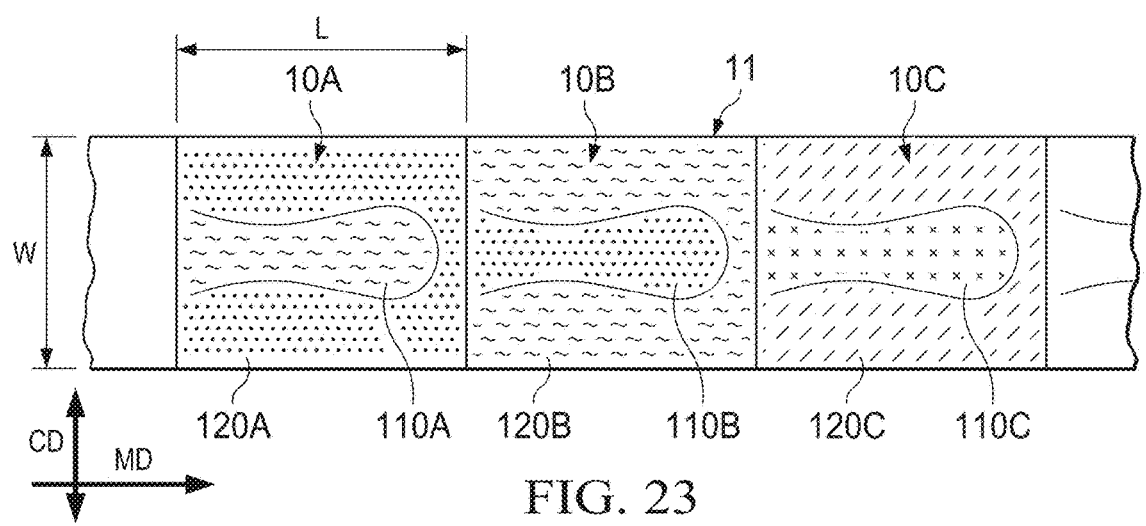
FIG. 23 is a plan view of a nonwoven substrate including nonwoven fabrics of the present disclosure.

As can be understood from the description of the forming belt 60 described in FIG. 22, and with reference to FIG. 23, the nonwoven substrate 11 made on belt 60 may be described as a nonwoven substrate 11 having a plurality of portions described herein as fabrics 10 ordered in at least one sequential relationship with respect to the longitudinal direction, i.e., the machine direction when made on forming belt 60. FIG. 23 is a schematic representation of a spunbond nonwoven substrate 11 showing the sequentially ordered fabrics 10, each fabric 10 having a different pattern within the various zones. Each fabric 10 may have an overall area OA defined, in a rectangular-shaped pattern, by a length L and width W. Each sequentially disposed fabric 10 may have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA may be present. As shown in FIG. 23, the first pattern 110A of fabric 10A may be different from the first pattern 110B of the fabric 10B, and may be different from the first pattern 110C of the fabric 10C. The same may be true for the second zones 120A, 120B, and 120C.

In general, the sequentially ordered nonwoven fabrics 10 of the nonwoven material 11 made on forming belt 60 may vary in their respective overall areas, intensive properties, and visual appearances. A common intensive property is an intensive property possessed by more than one zone (with respect to zonal patterns, such as that shown in FIG. 21) or region (for three-dimensional features such as the regular repeating patterns, such as that shown in FIG. 1). Such intensive properties of the nonwoven fabrics 10 may be average values, and may include, without limitation, density, volumetric density, basis weight, thickness, and opacity. For example, if a density is a common intensive property of two differential zones or regions, a value of the density in one zone or region may differ from a value of the density in the other zone or region. Zones (such as, for example, a first zone and a second zone) may be identifiable areas distinguishable from one another visually and by distinct intensive properties averaged within the zone.

Once produced, the individual nonwoven fabrics 10 may be cut to size and utilized for their intended purposes, such as for topsheets in disposable absorbent articles. One fabric 10 is cut to the appropriate overall area and adhered into a diaper, for example, by methods generally known in the art. Fabrics 10 may be cut prior to being assembled into a diaper or during the diaper making process the nonwoven substrate 11 may be brought together with other diaper components in web form, and cut to size after assembly.

Figure 24:
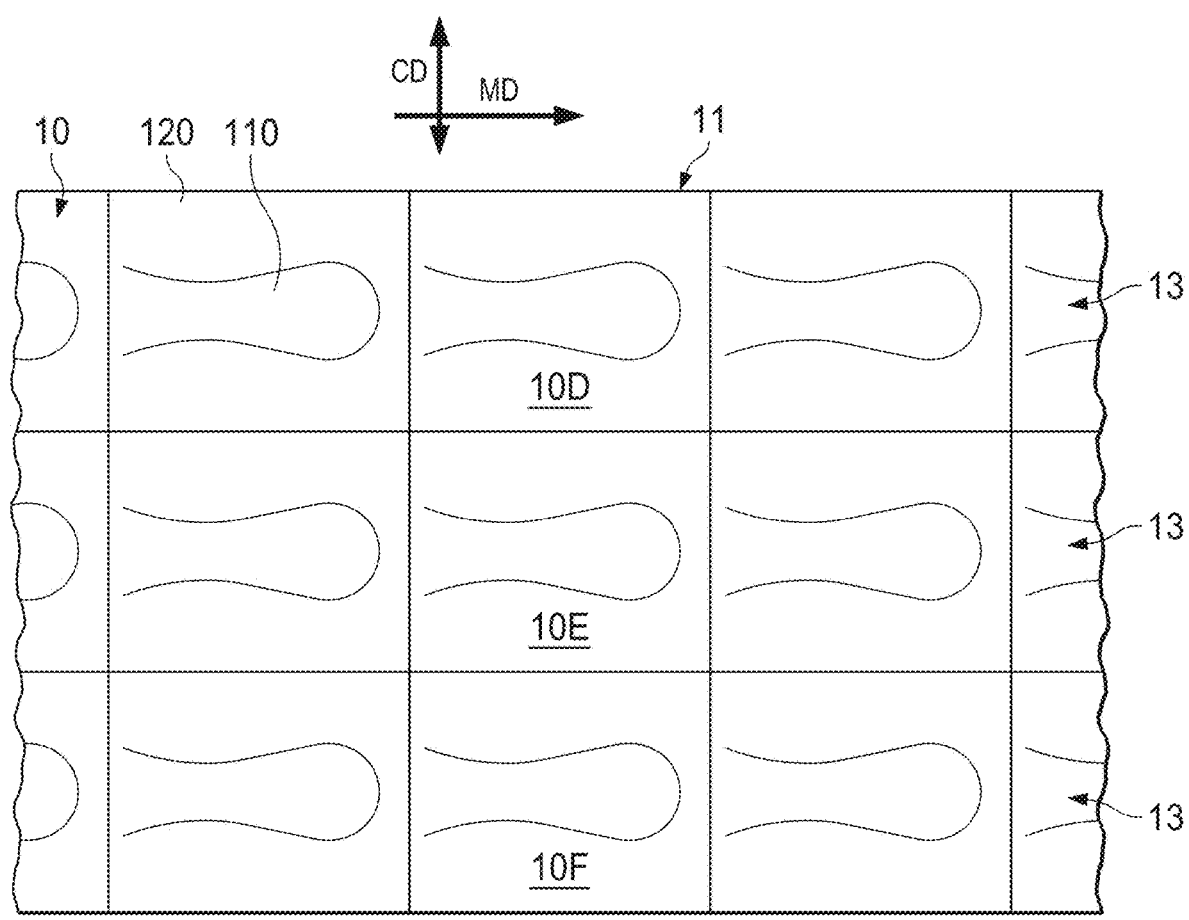
FIG. 24 is a plan view of a nonwoven substrate including nonwoven fabrics of the present disclosure.

As can be understood with reference to FIG. 24, the nonwoven substrate 11 made on belt 60 may be described as a nonwoven fabric 11 having a plurality of portions described herein as fabrics 10 ordered in at least one sequential relationship with respect to the longitudinal direction, i.e., the machine direction when made on forming belt 60, in at least one side-by-side relationship, i.e., in the cross machine direction when made on forming belt 60. FIG. 24 is a schematic representation of a spunbond nonwoven substrate 11 showing the sequentially ordered fabrics 10 in adjacent machine direction lanes 13, adjacent lanes having the side-by each fabrics 10, called out in FIG. 24 as 10D, 10E, and 10F. Each fabric 10 may have an overall area OA defined, in a rectangular-shaped pattern, by a length L and width W. Each sequentially disposed fabric 10 may have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA may be present. Each fabric 10 in side-by-side lanes may be substantially identical, or they can be different with respect to size, visual appearance, and/or intensive properties. Once produced, the nonwoven substrate 11 may be reeled for slitting into lanes for processing into consumer products, or slit and then reeled.

Another aspect of the present disclosure relates to spunbond commercial lines where multiple beams are utilized for improved laydown opacity and uniformity of the fabric. In some cases, there the apparatus may include triple spunbond beams (known in the art as "SSS") and may be combined with meltblown (M), for example, in an apparatus known as an "SSMMS" spunbond line.

By calendaring the nonwoven fabric 10 to have point bonds 90, fuzzing may be reduced. Fuzzing refers to the tendency of fibers to become loose and removed from the fabric 10. Loosening and removal may be because of frictional engagement with manufacturing equipment during production of disposable absorbent articles, or another surface, such as the skin of a person interacting with the fabric 10. In some uses, such as for topsheets in disposable absorbent articles, fuzzing is a negative consumer phenomena. But bonding fibers in place may also be a consumer negative as it may produce roughness on the surface of an otherwise soft nonwoven substrate. We have found expectedly the nonwoven substrates and nonwoven fabrics of the present disclosure may endure an increase in bonding (and a consequent decrease in fuzzing) with minimal loss in softness. Bonding may be accomplished by relatively closely spaced point bonds 90, with the spacing being determined by the desired level of fuzzing reduction. Bonding may also be achieved by known methods for chemically or thermally bonding nonwoven fibers, such as thermal bonding, ultrasonic bonding, pressure bonding, latex adhesive bonding, and combinations of such methods.

Further characterization of the present disclosure may be realized by focusing on the three-dimensional features within a visually discernible zone. Each zone, such as zones 110, 120, and 130, discussed above, may be described further with respect to microzones. A microzone is a portion of the nonwoven fabric 10 within a zone, that has at least two visually discernible regions and there is a common intensive property difference between these two regions. A microzone may comprise a portion of the nonwoven fabric 10 which crosses two or more zone boundaries that has at least two visually discernible regions and there is a common intensive property difference between these two regions The benefit of considering microzones in the present disclosure is to illustrate that in addition to differences in average intensive properties with a zone, such as zones the 110, 120, and 130, as discussed above, the present disclosure also provides for fabrics having differences in actual and/or average intensive properties between regions defined by the three-dimensional features within a zone, with the three-dimensional features precisely placed according to the design of the forming belt used to produce the fabrics. The difference between intensive properties between regions of the three-dimensional features provides for additional visual as well as functional benefits. The sharp visual contrast between regions may provide for extremely fine visually distinctive designs within a zone and between zones. Likewise, the precise placement of regions afforded by the precisely manufactured forming belt may provide for excellent and tailored softness, strength, and fluid handling properties of the zones. Thus, the present disclosure provides for the unexpected combination of differences in average intensive properties between zones and simultaneously differences in intensive properties of the regions making up a microzone.

Figure 25:
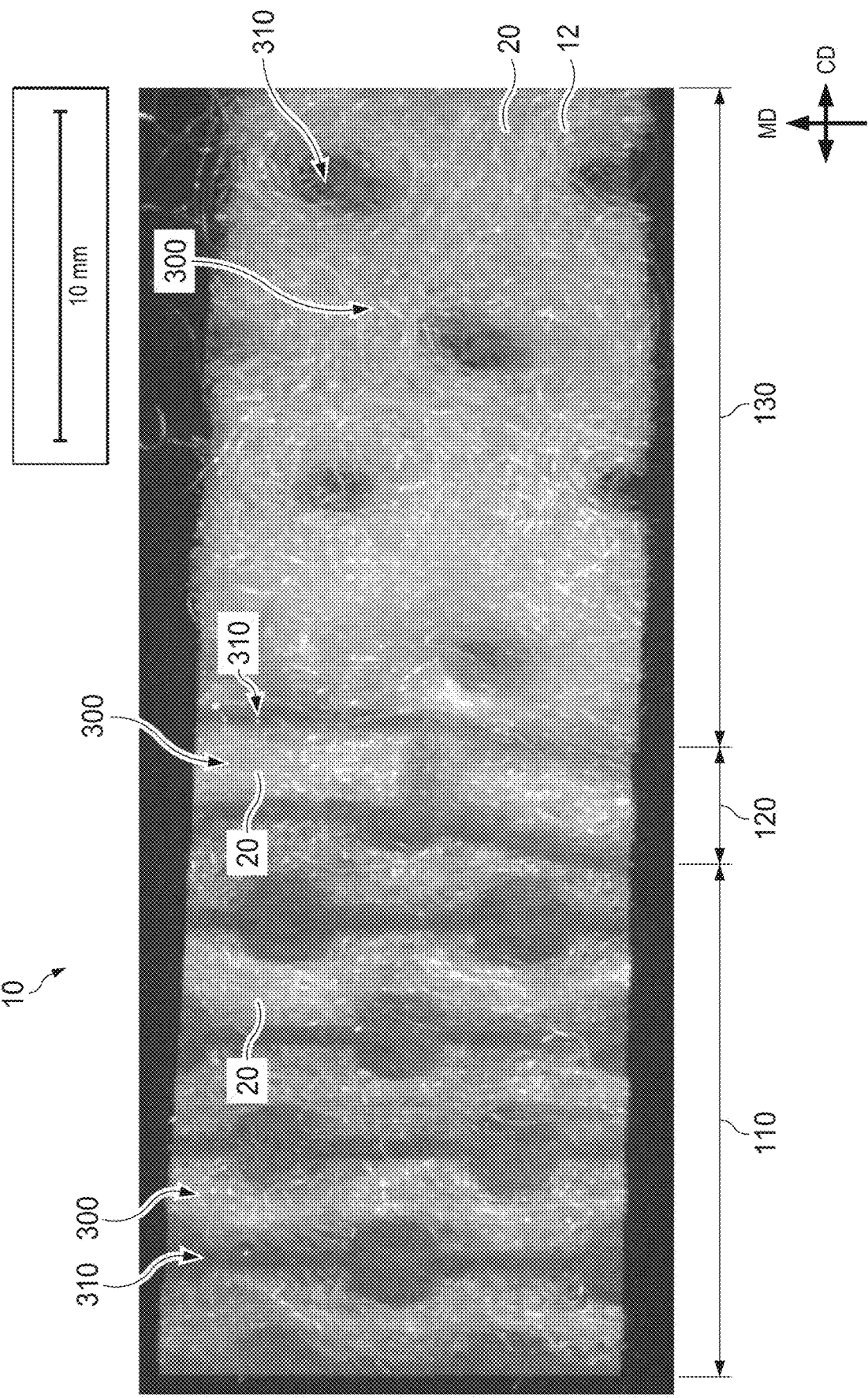
FIG. 25 is a photograph of an example nonwoven fabric of the present disclosure.
Figure 26:
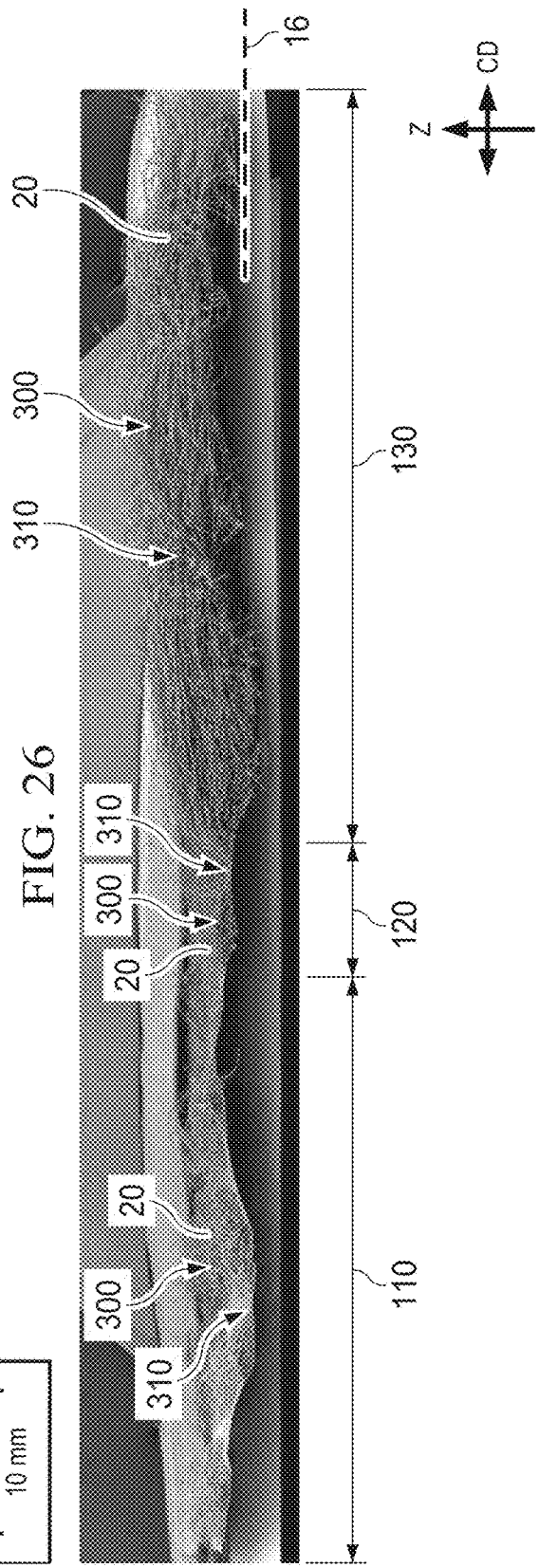
FIG. 26 is a photograph of cross section of the example nonwoven fabric of FIG. 25.

Regions defined by three-dimensional features may be understood with reference to FIG. 25 and FIG. 26. FIG. 25 shows a light microscope image of a portion of a fabric 10 according to the present disclosure, and FIG. 26 is a scanning electron micrograph (SEM) of a cross-section of the portion of the fabric shown in FIG. 25. Thus, FIGS. 25 and 26 show a portion of a nonwoven fabric 10 magnified for more precise description of the otherwise visually discernible features of the fabric. The portion of the nonwoven fabric 10 shown in FIG. 25 is approximately 36 mm in the CD and exhibits portions of at least three visually distinct zones as discussed below.

In FIGS. 25 and 26 which show a portion of one pattern of a nonwoven fabric 10, a first zone 110 (on the left side of FIG. 25) is characterized by generally MD-oriented rows of variable width first regions 300 separated by MD-oriented rows of variable width second regions 310. The first region is also the three-dimensional feature 20 that defines the first and second regions 300, 310. A three-dimensional feature is a portion of the nonwoven fabric 10 that was formed between or around a raised element of the forming belt, which in this description is the first region 300, such that the resulting structure has a relatively greater dimension in the Z-direction. The adjacent second region 310 generally has a common intensive property with the first region 300 and may have a relatively lower thickness value, i.e., lesser dimension in the Z-direction. The relative dimensions in the Z direction with respect to a plane of the first surface 16 as described above, may be seen in FIG. 26. Absolute dimensions are not critical; but the dimensional differences may be visually discernible on the nonwoven fabric 10 without magnification.

The present disclosure permits beneficial characteristics best expressed with respect to the regions defined by three-dimensional features in microzones. For example, as shown in FIG. 25, in zone 110 for each three dimensional features 20 there is a visible distinction between a first region 300 and a second region 310. As stated above, the visible distinction may exist in the nonwoven fabric 10 without magnification, the magnified views used herein are for purposes of clear disclosure. Any area that extends across the boundary between enough of first region 300 and second region 310 such that a difference in their respective intensive properties may be ascertained within the area may be a microzone. Additionally, light microscopy or microCT imagery of a structure may also be used to establish the location of regions and the area of a microzone.

The portion of nonwoven fabric 10 shown in FIG. 25 further illustrates another beneficial characteristic of the fabric 10, in that the differences in intensive properties between adjacent regions may be differences across zones. Thus, a microzone that spans an area encompassing second region 310 of zone 120 and first region 300 of zone 130 may be identified. Referring to the nonwoven fabric 10 shown in FIGS. 25 and 26, the difference in intensive properties exhibited by regions in microzones that a zone boundary may be significantly different in magnitude than the differences between intensive properties exhibited by regions within a zone.

Regardless of which zone, or which zonal boundary a particular microzone encompasses, the three-dimensional features may be characterized by the differences between intensive properties of the regions defined by them. In general, the nonwoven of the present disclosure may be a spunbond nonwoven fabric having a first surface defining a plane of the first surface. The fabric may have a plurality of three-dimensional features, each three dimensional feature defining a first region and a second region, the regions having a common intensive property that has a different value between them. The first region may be distinguished as being at a higher elevation than the second region with respect to the plane of the first surface, hence exhibiting a difference in each region's common intensive property of thickness. The two regions may also be distinguished as having different densities, basis weights, and volumetric densities. That is, the two regions may be distinguished within a micro zone of the spunbond nonwoven fabric as being different with respect to common intensive properties, including properties such as thickness, density, basis weight, and volumetric density. One or both regions of a microzone may be fluid permeable. The higher density region of a microzone may be fluid permeable.

Within zone 110 of the portion of fabric shown in FIG. 25, for example, there may be three-dimensional features 20 defining at least two regions, a first region 300 and a second region 310. The difference in thickness, basis weight, and volumetric density between the first and second regions for zone 110 shown in FIG. 25 may be 274 microns, 1 gsm, and 0.437 g/cc, respectively, for example.

Likewise, within zone 130 of the portion of fabric shown in FIG. 25, for example, there may be three-dimensional features 20 defining at least two regions, a first region 300 and a second region 310. The difference in thickness, basis weight, and volumetric density between the first and second regions for zone 130 shown in FIG. 25 may be 2083 microns, 116 gsm, and 0.462 g/cc, respectively, for example.

Additionally, within zone 120 of the portion of fabric shown in FIG. 25, for example, there may be three-dimensional features 20 defining at least two regions, a first region 300 and a second region 310. The difference in thickness, basis weight, volumetric density between the first and second regions for the portion of fabric shown in FIG. 25 may be 204 microns, 20 gsm, 0.53 g/cc, respectively, for example. The zone 120 forms what appears in an unmagnified view of nonwoven fabric 10 to be a stitched boundary between zones 110 and 130.

Further, a zone that encompasses the boundary between zones 120 and 130 of the portion of fabric shown in FIG. 25, for example, there are at least two regions, a first region 300 in zone 130 and a second region 310 in zone 120. The difference in thickness, basis weight, and volumetric density between the first and second regions for the portion of fabric shown in FIG. 38 may be 2027 microns, 58 gsm, and 0.525 g/cc, respectively, for example.

Figure 29:
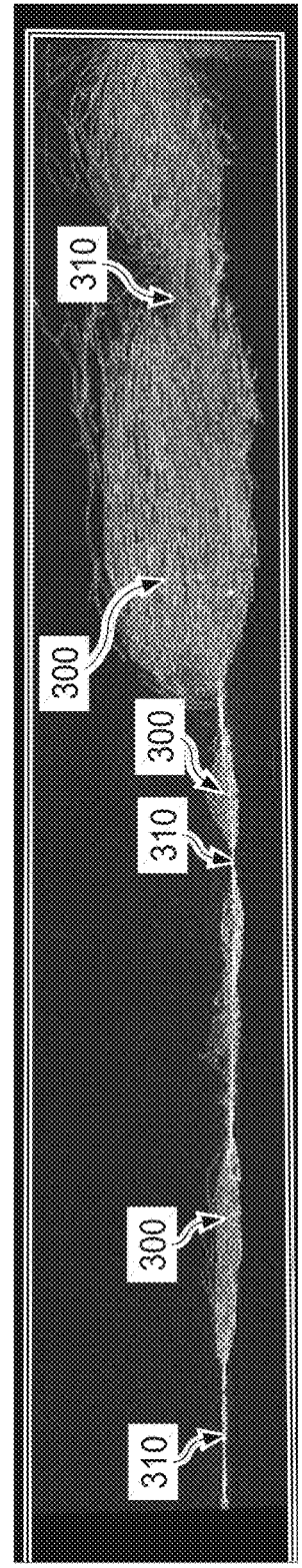
FIG. 29 is a Micro CT image of a cross section of the example nonwoven fabric of FIGS. 27 and 28.
Figure 27:
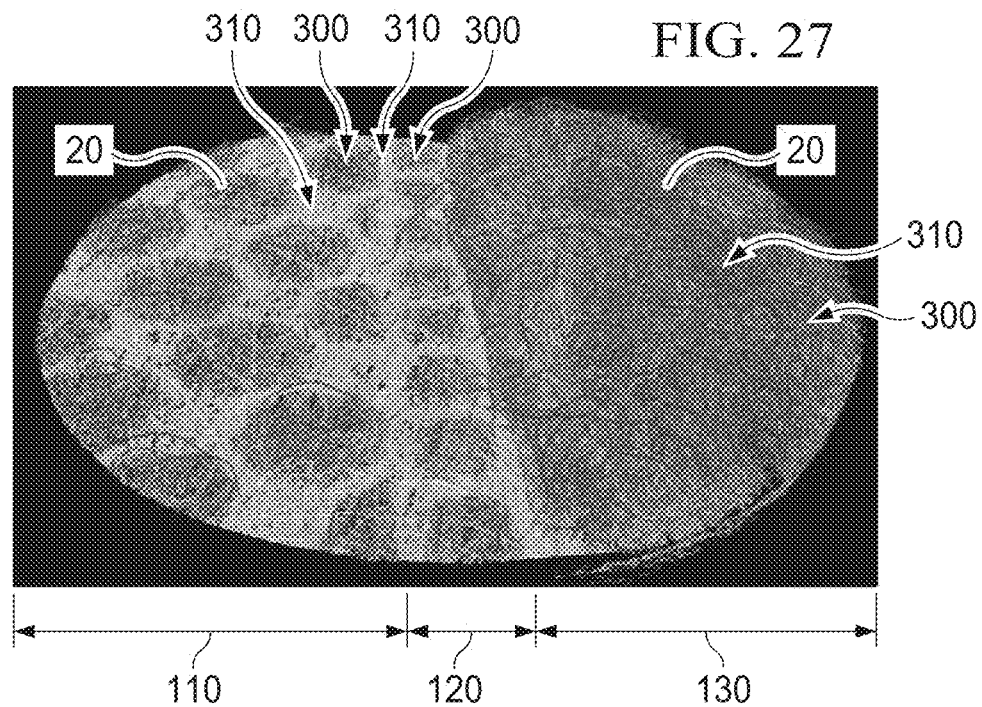
FIG. 27 is a Micro CT perspective view image of an example nonwoven fabric of the present disclosure.
Figure 28:
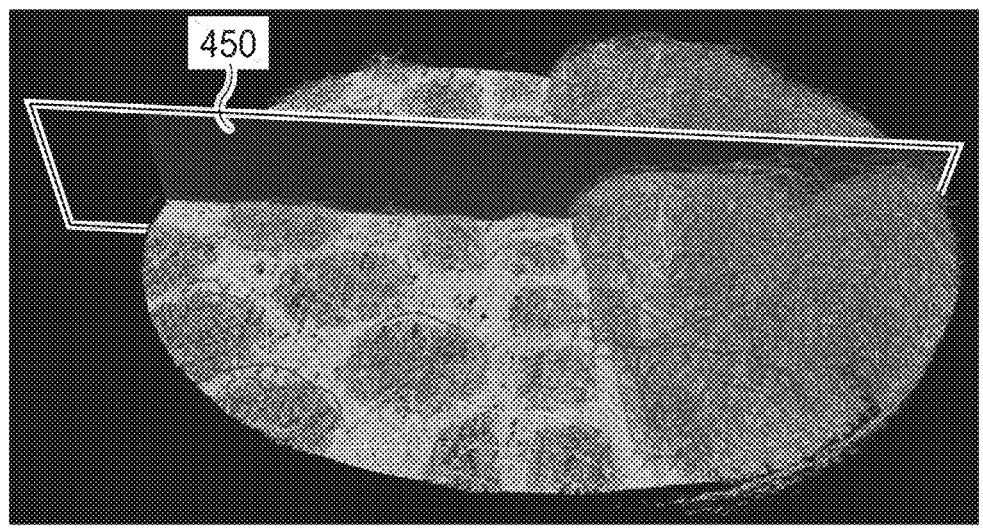
FIG. 28 is a Micro CT perspective view image of an example nonwoven fabric of the present disclosure.

Microzones are discussed in more detail with reference to FIGS. 27-29 and the data depicted in FIG. 31. FIGS. 27-29 are Micro-CT scans of a portion of a nonwoven fabric 10 similar in pattern to that of the nonwoven fabric 10 shown in FIG. 25. The Micro-CT scan permits description of the same features as shown in FIG. 25 in a slightly different manner and in a way that permits very precise measurement of intensive properties.

As shown in FIG. 27, zones 110, 120, and 130 are clearly visible, with their respective three-dimensional features 20. As depicted in FIGS. 27 and 28, the three-dimensional features are the dark-colored portions, with the dark color also representing the first region 300 of a three-dimensional feature 20, and the adjacent light-colored portions being the second region 310 for the three-dimensional feature 20.

The Micro-CT scan permits the image to be "cut" and cross-sectioned, as shown by the cut plane 450 in FIG. 28. A cut plane may be placed anywhere on the image; for the purposes of the present disclosure, the cut plane 450 cuts a cross section substantially parallel to the Z axis so as to produce the cross-sectional image in FIG. 29.

The Micro-CT technology permits intensive properties to be precisely and directly measured. Thickness measurements may be made directly from imaged cross sections based on the scale magnification, such as the cross section shown in FIG. 29. Further, the color differential between first regions and second regions is representative and proportional to differences in basis weight, volumetric density, and other intensive properties, which may likewise be directly measured. Micro-CT methodology is explained below in the Test Methods section.

Figure 30:
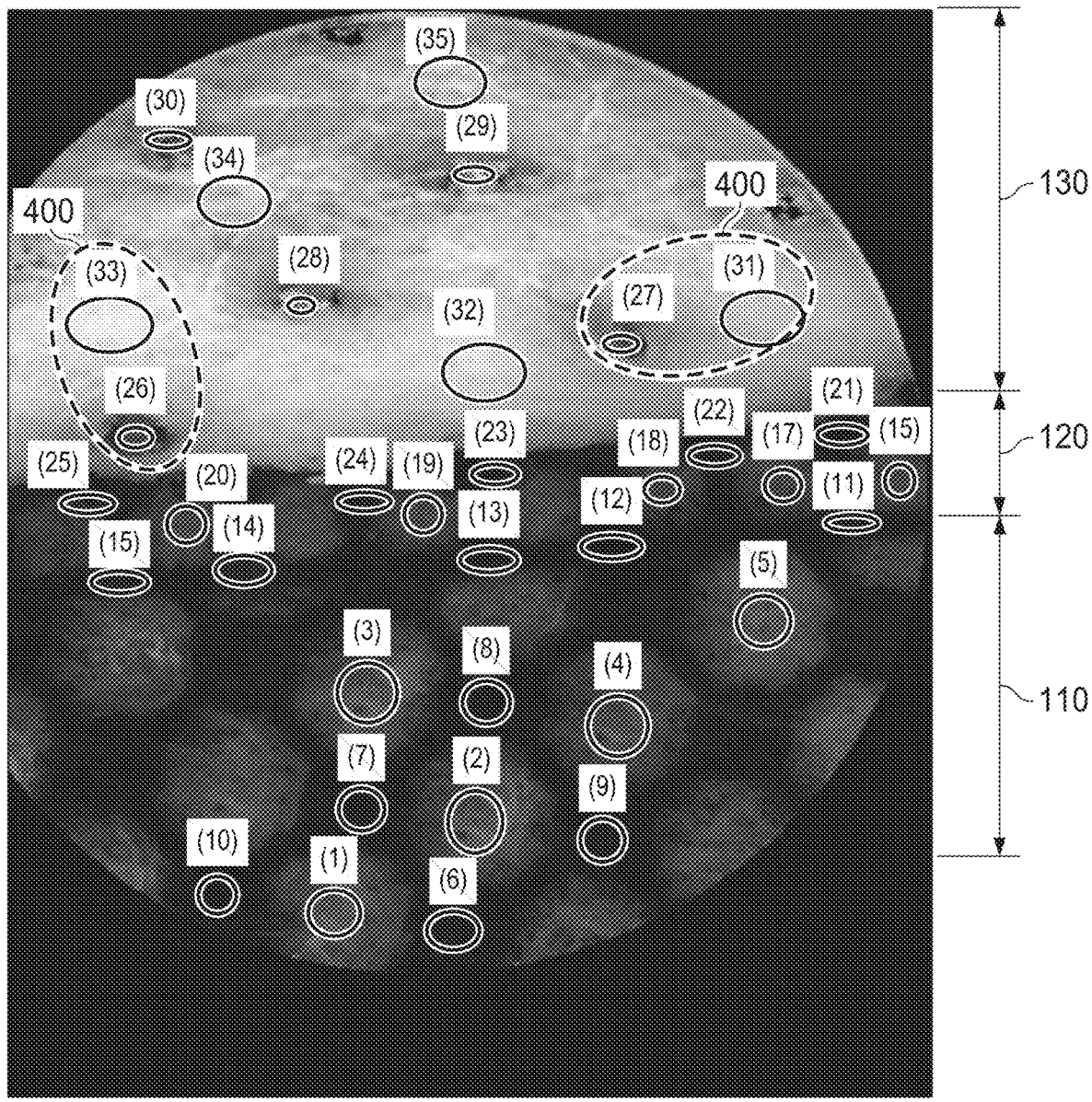
FIG. 30 is a Micro CT plan view image of the example nonwoven fabric of FIGS. 27 and 28.

FIG. 30 is a Micro-CT scan image of the portion of nonwoven fabric 10 shown in FIGS. 27 and 28. Utilizing, for specific first and second regions shown as numbered portions of the nonwoven fabric 10 may be analyzed. In FIG. 30, specific regions were manually selected and analyzed to measure thickness, basis weight, and volumetric density, and the data is produced in FIG. 31.

Figure 31:
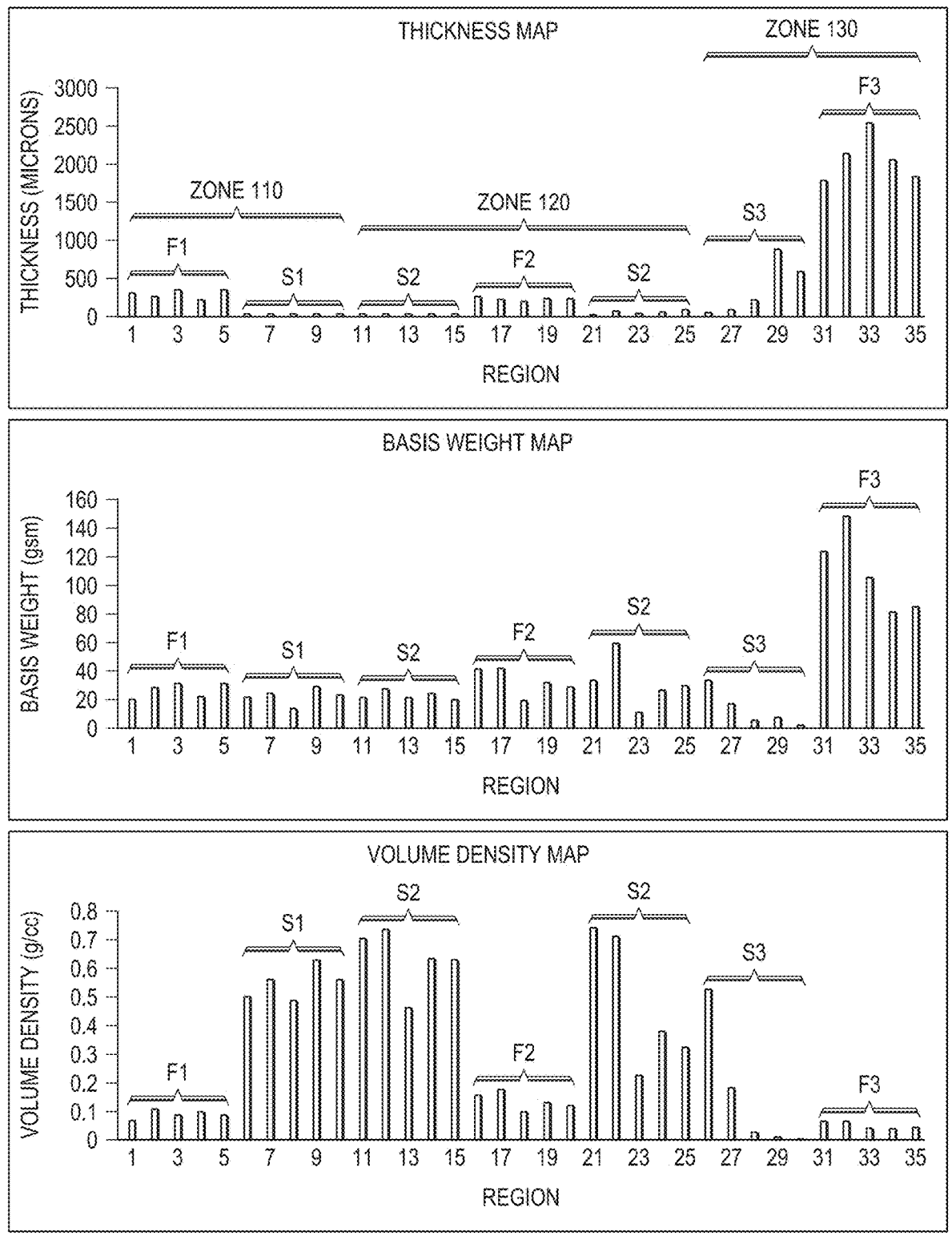
FIG. 31 is a graphical depiction of various benefits of the nonwoven fabrics of the present disclosure.

FIG. 31 shows data for groupings of first and second region measurements made within the three zones depicted in FIG. 30. The x-axis is the regions, with the numbers corresponding to the numbered regions on FIG. 30. First region measurements are labeled as Fn (e.g., F1) and second regions measurements are labeled as Sn (e.g., S1). Thus, regions 1-5 are first regions F1, each being in zone 110. Regions 6-10 are second regions S1, also being in zone 110. Likewise, first regions F2 are regions 16-20 in zone 120, and regions 11-15 and 21-25 are second regions S2 in zone 120. Finally, regions 31-35 are first regions F3 in zone 130 and regions 26-30 are second regions S2 in zone 130. The numbered regions are consistently depicted across all three graphs of FIG. 31, but for simplicity, the zones 110, 120, and 130 are depicted only on the Thickness Map.

The graphs shown in FIG. 31 represent graphically the magnitude of difference in intensive properties between first regions and second regions within any one of the zones, and may be used to see graphically the difference in intensive properties for pairs of regions making up a microzone. For example, one can see that in zone 110 that basis weight between the two regions may be substantially the same, but the thickness (caliper) may vary from about 400 microns in the first regions to about 40 microns in the second regions, or about a 10× differential. The volumetric density in zone 110 may vary from about 0.1 g/cc to about 0.6 g/cc. Similar quantifiable distinctions may be understood for each of the zones shown.

Thus, with reference to FIG. 30 and FIG. 31 together, further characterization of the beneficial structure of a fabric 10 of the present disclosure may be understood. The nonwoven fabric 10 may be described as having at least two visually distinct zones, e.g., zones 110 and 120, with each of the zones having a pattern of three-dimensional features, each of the three-dimensional features defining a microzone comprising first and second regions, e.g., regions 300, 310, and wherein the difference in values for at least one of the microzones in the first zone is quantifiably different from the difference in values for at least one of the microzones in the second zone. For example, in FIG. 30, two representative microzones 400 in zone 130 are designated as the pair of regions marked as areas 31 and 27 and 33 and 26. That is, first region 31 and second region 27 form a microzone, and first region 33 and second region 26 form a microzone. Likewise, two representative microzones 400 in zone 120 are designated as the pair of regions marked as areas 19 and 24 and 17 and 22. From FIG. 31, Tables 4-7 may be populated as shown:

TABLE 1

Illustrative examples of differences in thickness in microzones

|  |  |  | Thickness (microns) | Difference in Thickness (microns) |
|---|---|---|---|---|
| Zone 130 | Microzone 1 | First Region 31 | 1802 | 1709 |
|  |  | Second Region 27 | 93 |  |
|  | Microzone 2 | First Region 33 | 2548 | 2484 |
|  |  | Second Region 26 | 64 |  |
| Zone 120 | Microzone 1 | First Region 19 | 242 | 172 |
|  |  | Second Region 24 | 70 |  |
|  | Microzone 2 | First Region 17 | 235 | 183 |
|  |  | Second Region 23 | 52 |  |

TABLE 2

Illustrative examples of differences in basis weight in microzones

|  |  |  | Basis weights (gsm) | Difference in Basis weights (gsm) |
|---|---|---|---|---|
| Zone 130 | Microzone 1 | First Region 31 | 124 | 107 |
|  |  | Second Region 27 | 17 |  |
|  | Microzone 2 | First Region 33 | 106 | 72 |
|  |  | Second Region 26 | 34 |  |
| Zone 120 | Microzone 1 | First Region 19 | 32 | 5 |
|  |  | Second Region 24 | 27 |  |
|  | Microzone 2 | First Region 17 | 42 | 30 |
|  |  | Second Region 23 | 12 |  |

TABLE 3

Illustrative examples of differences in volumetric density in microzones

|  |  |  | Volumetric Density (g/cc) | Difference in Volumetric Density (g/cc) |
|---|---|---|---|---|
| Zone 130 | Microzone 1 | First Region 31 | 0.069 | 0.116 |
|  |  | Second Region 27 | 0.185 |  |
|  | Microzone 2 | First Region 33 | 0.041 | 0.49 |
|  |  | Second Region 26 | 0.531 |  |
| Zone 120 | Microzone 1 | First Region 19 | 0.133 | 0.251 |
|  |  | Second Region 24 | 0.384 |  |
|  | Microzone 2 | First Region 17 | 0.185 | 0.044 |
|  |  | Second Region 23 | 0.229 |  |

TABLE 4

Illustrative examples of differences in intensive properties within different zones:

|  | Thickness (Microns) | Thickness Differences | Basis Weights (gsm) | Basis Weights Differences | Volumetric Density (g/cc) | Volumetric Density Differences |
|---|---|---|---|---|---|---|
| Zone 130 First Region 32 | 2147 | 2118 | 149 | 135 | 0.069 | 0.423 |
| Zone 110 Second Region 8 | 29 |  | 14 |  | 0.492 |  |

The four representative microzones from two zones are shown in Tables 1-4 for illustration. But as can be understood, each pair of first and second regions in FIG. 30 may likewise be quantified to further populate additional rows in Table 1, but for purposes of conciseness are not. In general, for any fabric having two or more zones, each zone having a pattern of three-dimensional features defining microzones, the intensive properties may be measured and tabulated as illustrated herein with reference to FIGS. 30 and 31 to understand both the difference in values for intensive properties within a zone, and differences in values of intensive properties between one region in first zone to another region in a second zone.

A microzone spanning two zones, such as zones 110 and zone 130, may have an even greater difference in intensive properties relative to a microzone within a single zone. For example, viewing the data for a microzone spanning a first region of zone 130, for example at first region 32, and a second region of zone 110, for example at second region 8, the microzone exhibits dramatic differences in all of thickness, basis weight and volumetric density. The thickness of first region 32 of zone 130 is about 2100 microns, while the thickness of second region 8 of zone 110 is about 29 microns, or about a 72× differential or greater than about 25 microns. Likewise, the basis weight of first region 32 of zone 130 may be as high as 150 gsm, while the basis weight of second region 8 of zone 110 may be about 14 gsm, or about a 10× differential or greater than 5 gsm. Further, the volumetric density of first region 32 of zone 130 may be about 0.069 g/cc, while the volumetric density of second region 8 of zone 110 may be 0.492 g/cc, or about a 7× differential or greater than about 0.042 g/cc.

For each of the measured intensive property parameters of the various regions of a microzone, such a measurement is done using the micro CT method described herein. The resolution of the method supports establishing the intensive properties of microzone regions so differences and ratios comparisons of regions as described herein may be dimensioned.

Figure 34:
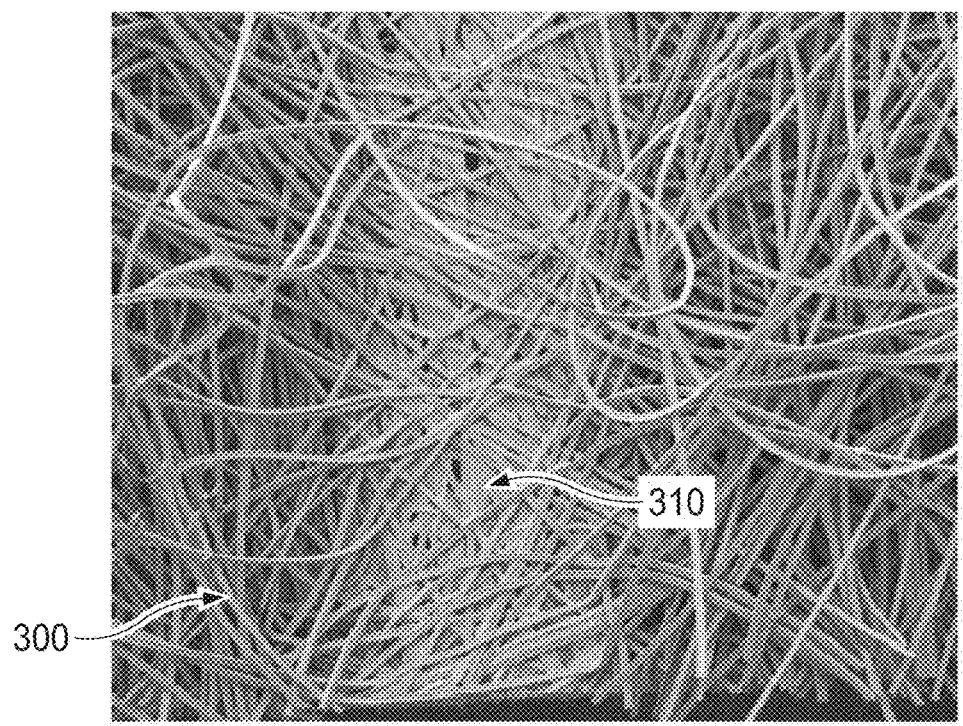
FIG. 34 is a photograph of a portion of an example nonwoven fabric of the present disclosure.

Further characterization of a fabric 10 may be made with reference to FIGS. 32-36, which are SEMs showing in greater detail certain aspects of the nonwoven fabric 10 and regions therein. FIGS. 32-36 are photographs of magnified portions of zone 110 of the fabric shown in FIG. 25. The nonwoven fabric 10 shown in FIG. 25 was made according to the process described above with reference to FIG. 7 in which the fabric was processed through a nip formed by compaction rolls 70 and 72, with roll 72 which contacts first side 12 being heated to cause partial bonding of fibers in the second regions 301. FIGS. 32 (facing the belt) and 46 (facing the heated compaction roll) are SEMs of a portion of the second surface 14 and first surface 12, respectively, magnified to 20X. FIGS. 34 (facing the belt) and 48 (facing the heated compaction roll) are photographs of a portion of the second surface 14 and first surface 12, respectively, magnified to 90X, and show in detail the beneficial structural characteristic of the partial bonding of fibers formed by compaction rolls 70 and 72.

Figure 35:
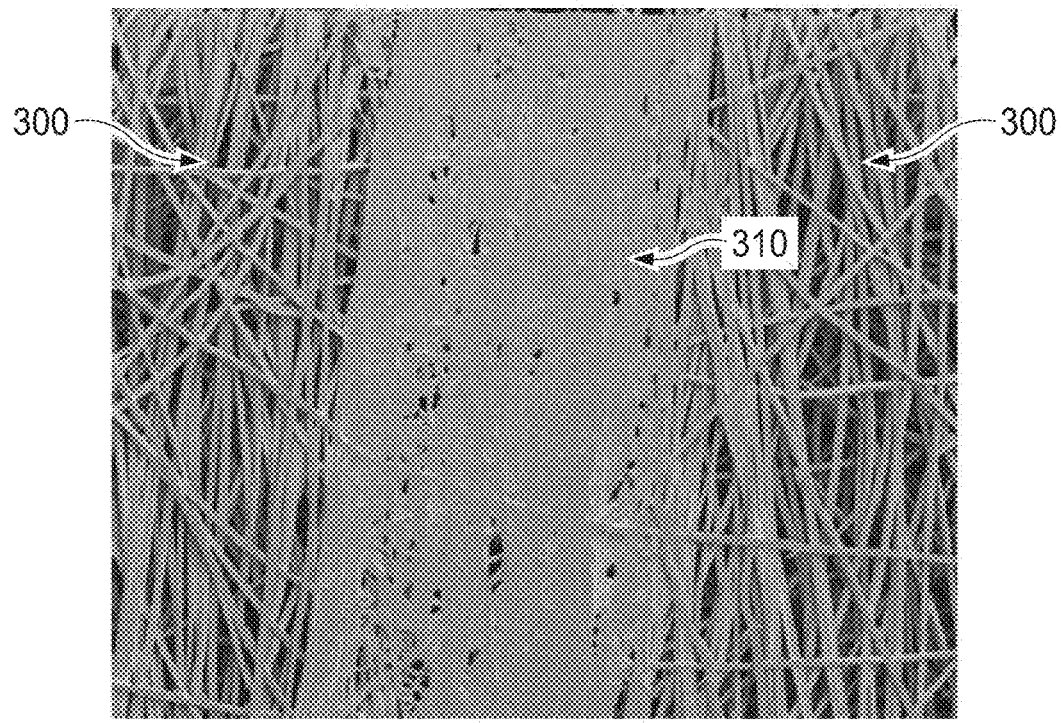
FIG. 35 is a photograph of a portion of an example nonwoven fabric of the present disclosure.
Figure 36:
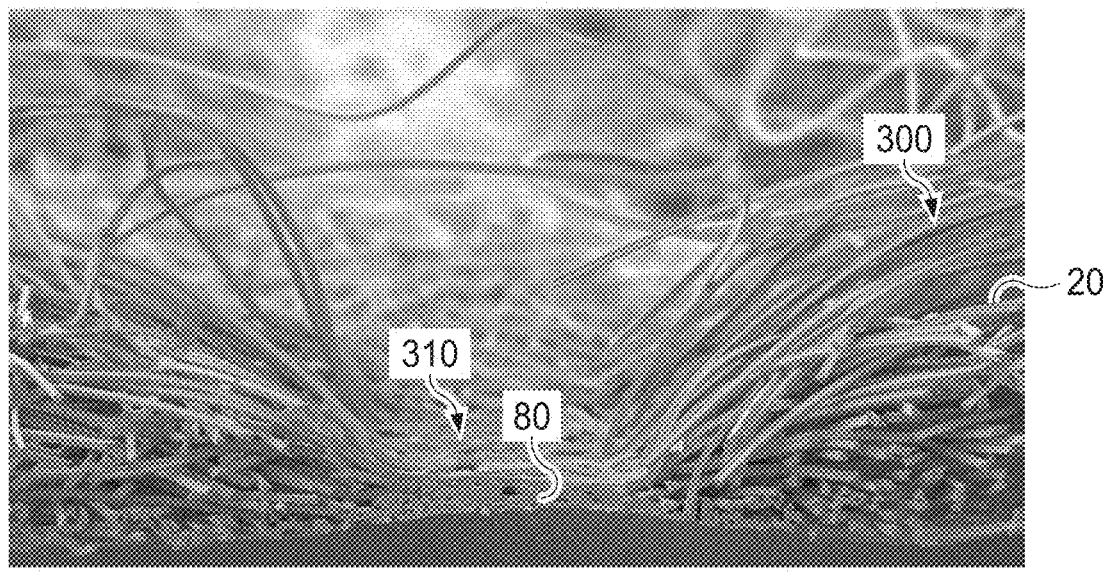
FIG. 36 is a photograph of a cross section of the example nonwoven fabric of FIGS. 36 and 35.
Figure 37:
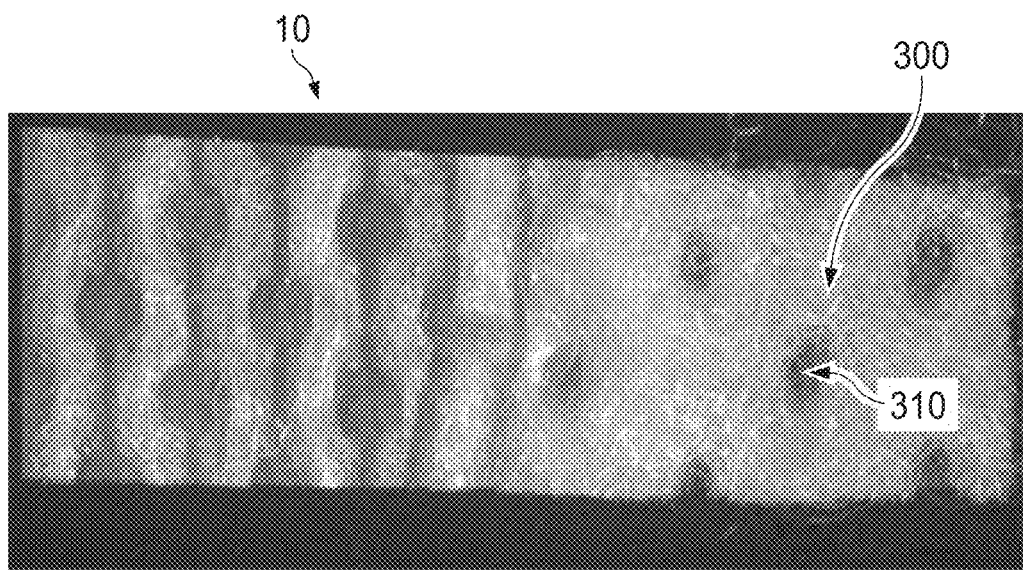
FIG. 37 is a photograph of a portion of an example nonwoven fabric of the present disclosure.

As can best be seen in FIGS. 34 and 35, as well as the cross sectional view of FIG. 36, the heated compaction rolls may cause thermal bonding of fibers to different degrees with a beneficial effect on the overall fabric 10. As shown, the fibers in contact with a heated roll, e.g., roll 70 in contact with first surface 12 of fabric 10, may be melt bonded such that the first surface 12 experiences relatively greater fiber-to-fiber bonding than does the second surface 14. The bonded fibers 80 of the first surface may be substantially completely melt bonded to form, in effect, a film skin of bonded fibers, while the fibers in the second region 310 on the second side 14 may experience little to no bonding. This feature permits a nonwoven fabric 10 for use in a disposable absorbent article, e.g., as a topsheet, to maintain physical integrity during manufacture and use, as well as relative softness on one side, which may be the wearer-facing, skin-contacting side.

Even in the microzones with the greatest thickness differential, this "bond skinning" effect serves the purpose of maintaining web integrity, while not significantly impacting softness, or other beneficial properties such as fluid handling properties. As can be understood with reference to FIGS. 37-40, the differential in the extent of thermal bonding of fibers may be such that fibers on the first surface 12 at a second region 310 may be complete, or substantially complete, while the extent of thermal bonding of fibers on the second surface 14 at a first region 300 may be minimal, to no thermal bonding.

Figure 38:
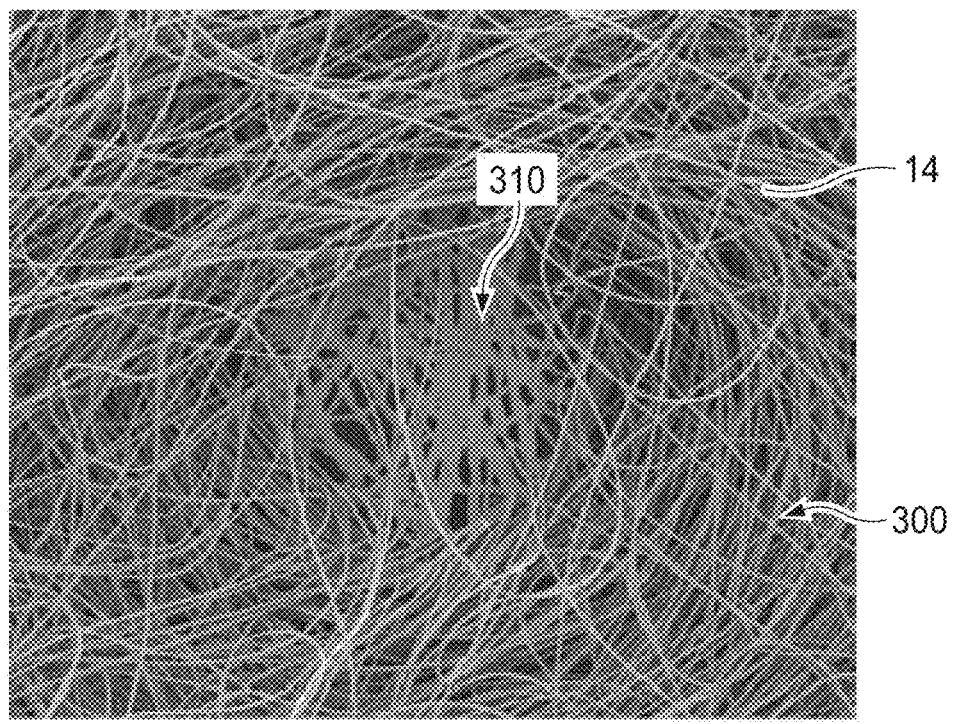
FIG. 38 is a photograph of a portion of an example nonwoven fabric of the present disclosure.
Figure 39:
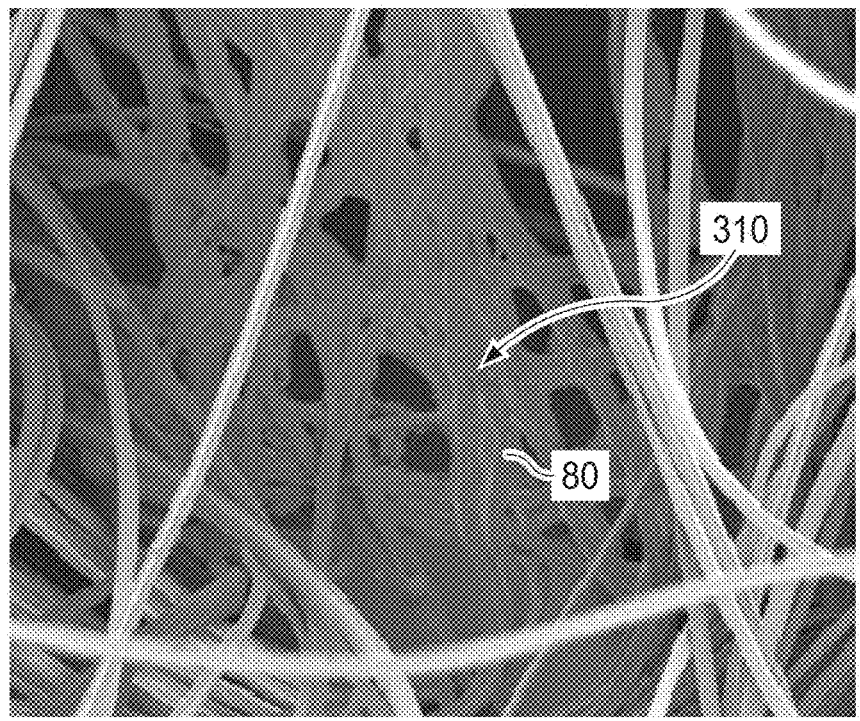
FIG. 39 is a photograph of a portion of an example nonwoven fabric of the present disclosure.
Figure 40:
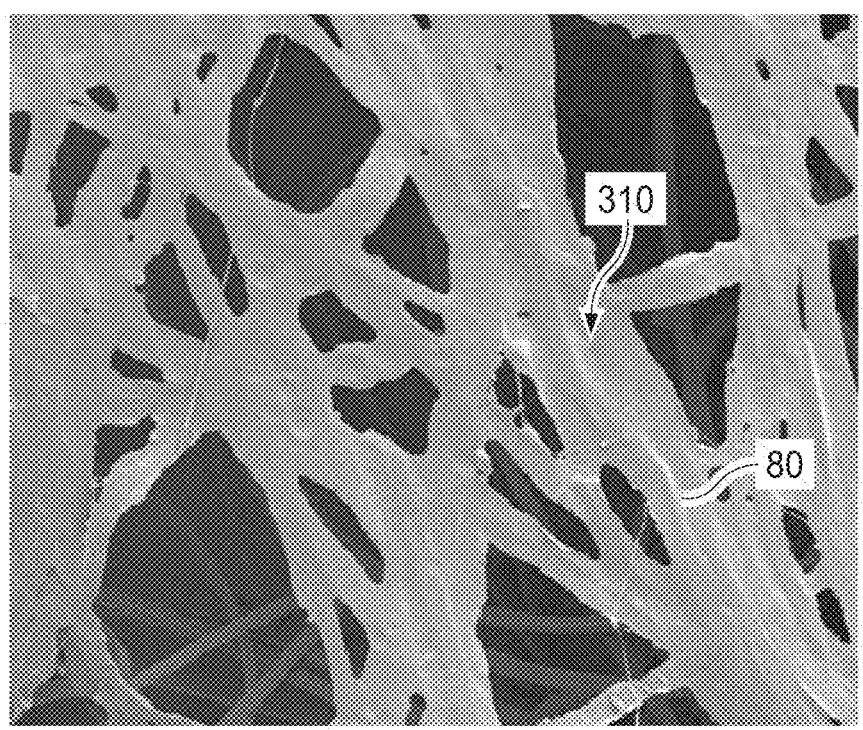
FIG. 40 is a photograph of a portion of an example nonwoven fabric of the present disclosure.

FIG. 37 shows again the portion of nonwoven fabric 10 shown in FIG. 25. FIGS. 38-40 show magnified images of one microzone, indicated in FIG. 37 as a first region 300 and second region 310, which visually appears to be a hole or an aperture. FIGS. 38 and 39 show the microzone as it appears on the second surface 14 magnified to 40X and 200X, respectively. FIG. 40 shows the second region 310 as it appears on the first side 12 under 200× magnification. Fibers in the second region 310 are completely, or substantially completely bonded, while fibers in the first region 300 are completely, or substantially completely unbonded. The benefit of the illustrated structure is that a microzone may function as a fluid pervious aperture, while the bonded regions of the second region 310 simultaneously functioning to maintain physical integrity of the fabric 10.

Microzones, therefore, play a significant role in the overall physical structure and functioning of a fabric 10 of the present disclosure. Producing relatively closely spaced, precisely designed three-dimensional features, enabled by the forming belt of the present disclosure, a fabric 10 may exhibit visually distinct zones, microzones, and three-dimensional features that provide for functional superiority in the areas of, at least, softness and fluid handling, as well as visually attractive aesthetic designs. The potential difference in physical properties of the first and second surfaces permits the nonwoven fabric 10 to be designed for both strength and softness, both form and function.

Figure 41:
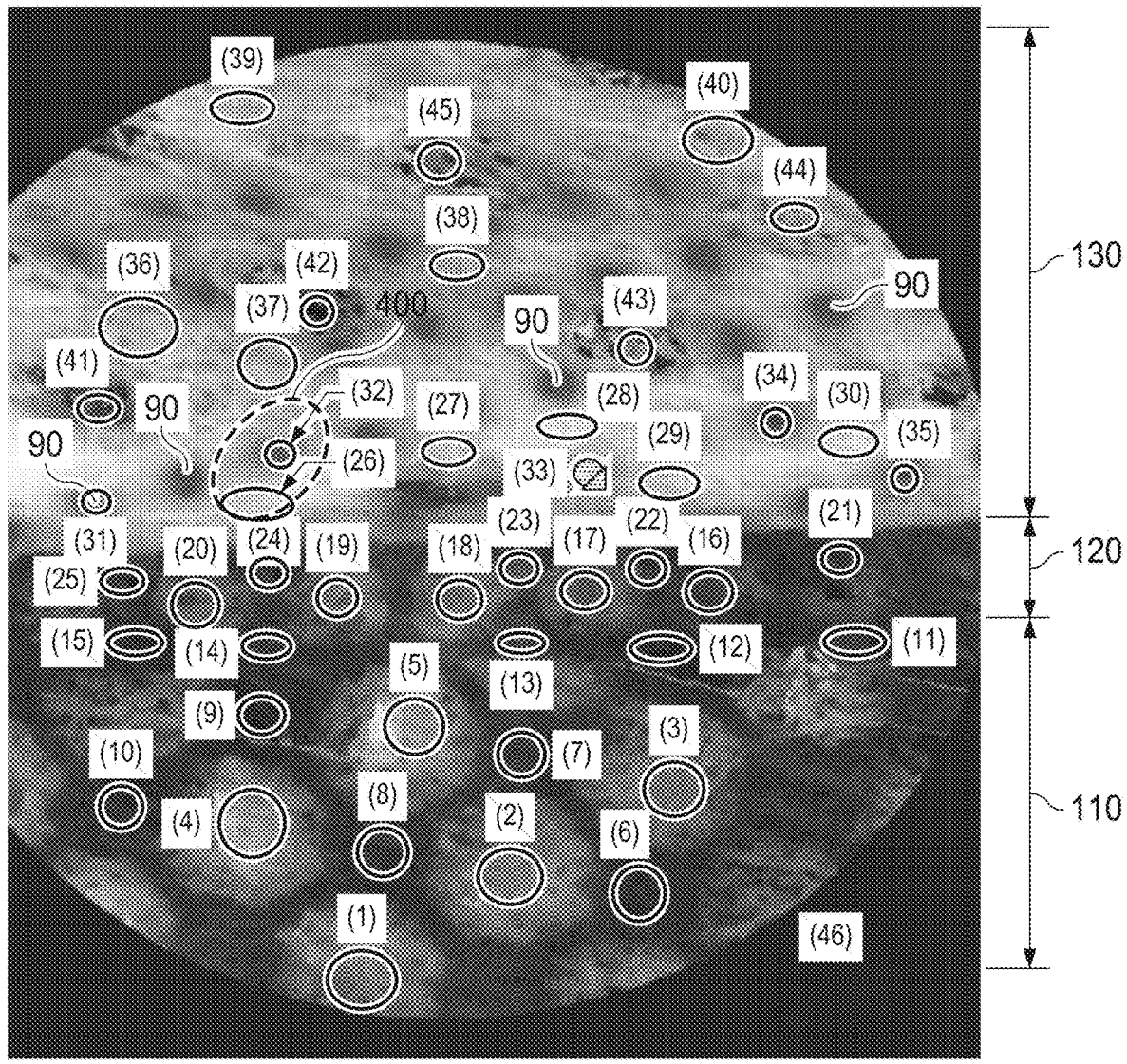
FIG. 41 is a Micro CT plan view image of the example nonwoven fabric of FIGS. 27 and 28 after experiencing additional processing.

FIG. 41 is a Micro-CT scan image of the portion of nonwoven fabric 10 similar to that shown in FIGS. 27 and 28, but having been subjected to the additional processing step of forming point bonds 90 in the nip of calendar rollers 71 and 73. As above, with respect to the discussion of FIGS. 30 and 31, for specific point bond microzones 400 first and second regions shown as numbered portions of the nonwoven fabric 10 may be analyzed, and include regions of point bonds, specifically in the numbered areas 31-35. For example, adjacent regions 32 and 26 form a microzone 400 in third zone 130. In FIG. 41, the specific regions were visually discerned to identify regions including the added point bond regions and analyzed to measure thickness, basis weight, and volumetric density, and the data is produced in FIG. 42, where the thickness, basis weight and volumetric density of all the regions, including the point bond regions are quantified and compared.

Figure 42:
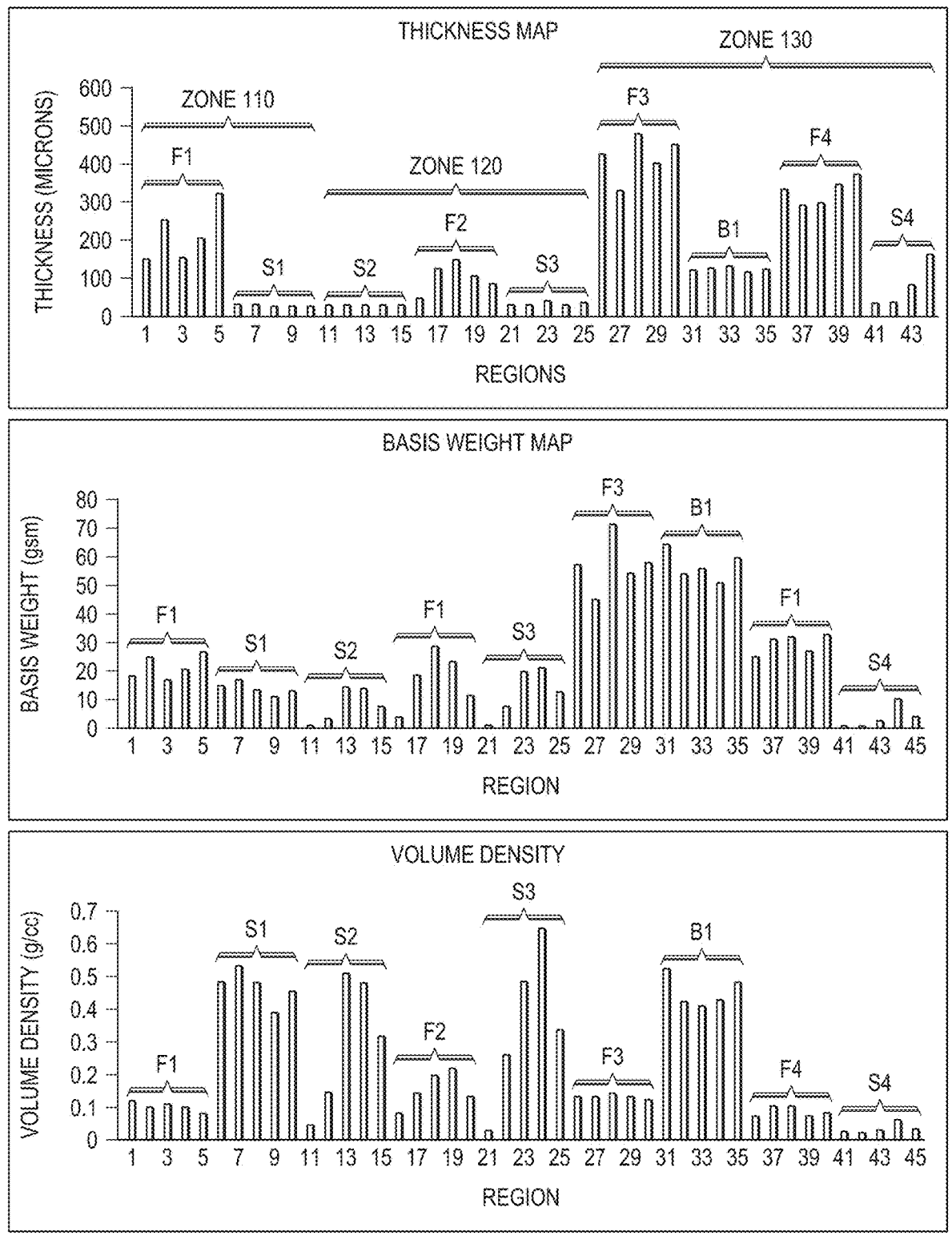
FIG. 42 is a graphical depiction of various benefits of the nonwoven fabrics of FIG. 41.

FIG. 42 shows data for groupings of first and second region measurements made within the three zones depicted in FIG. 41. The x-axis is the regions, with the numbers corresponding to the numbered regions on FIG. 30. First region measurements are labeled as Fn (e.g., F1) and second regions measurements are labeled as Sn (e.g., S1). Thus, regions 1-5 are first regions F1, each being in zone 110. Regions 6-10 are second regions S1, also being in zone 110. Likewise, first regions F2 are regions 16-20 in zone 120, and regions 11-15 and 21-25 are second regions S2 in zone 120. Finally, regions 31-35 are second regions but are point bonds 90 denoted on FIG. 55 as B1 to distinguish them in this disclosure as having been formed by a point bonding process. First regions F3 in zone 130 are regions 26-30 and 36-40, while regions 41-44 are second regions S2 in zone 130. The numbered regions are consistently depicted across all three graphs of FIG. 42, but for simplicity, the zones 110, 120, and 130 are depicted only on the Thickness Map.

The graphs shown in FIG. 42 represent graphically the magnitude of difference in intensive properties between first regions and second regions within any one of the zones of a fabric subjected to a calendaring point bonding step, and may be used to see graphically the difference in intensive properties for pairs of regions making up a microzone. For example, one can see that in zone 110 that basis weight between the two regions may vary within a range narrower than does thickness or volumetric density. For example, the thickness (caliper) may vary from about 325 microns in the first regions to about 29 microns in the second regions of zone 110, or about a 10× differential. The volumetric density in zone 110 may vary from about 0.08 g/cc to about 0.39 g/cc. Similar quantifiable distinctions may be understood for each of the zones shown.

In general, regions of a microzone may have broadly varying values for basis weight, thickness, and volumetric density.

Thus, with reference to FIG. 41 and FIG. 42 together, further characterization of the beneficial structure of a fabric 10 of the present disclosure may be understood specifically with respect to the thermal calendar point bonds 90. Focusing for purposes of description on zone 130, three-dimensional features defining a microzone comprising first and second regions which are point bonded regions may be identified and the values of intensive properties quantified. For example, in FIG. 41, a representative point bond microzone 400 in zone 130 may be the pair of regions marked as areas 26 and 32 or 30 and 35. That is, first region 26 and second region 32 form a point bond microzone 400, and first region 30 and second region 35 form a point bond microzone 400.

The differences in certain intensive properties for point bond microzones can be seen in FIG. 42. For example, taking the two point bond microzones 400 described above, e.g., the two point bond microzones 400 of regions 26 and 32 and 30 and 35, respectively, one can see there is a slight difference in basis weight between the first regions and second regions ranging from about 55 to about 60 gsm, but the same regions exhibit a significant difference in thickness of from about 430 microns to about 460 microns to about 125 microns, and a significant difference in volumetric density of from about 0.13-0.14 g/cc to about 0.41-0.48 g/cc. Other differences in intensive properties may be observed by reference to FIG. 42.

Bond points 90 may play a significant role in the overall physical structure and functioning of a fabric 10 of the present disclosure. By adding bond points 90 to the fabric 10 comprising relatively closely spaced, precisely designed three-dimensional features, enabled by the forming belt of the present disclosure, a fabric 10 may be further improved to exhibit an unexpected combination of visually distinct zones, microzones, and three-dimensional features that provide for functional superiority in the high performance combination of softness, strength, low fuzz, and fluid handling, as well as visually attractive aesthetic designs.

The bond point feature provides for a nonwoven fabric 10 to be designed for the highest combined performance of strength, softness, fluid handling, and visual aesthetics, especially considering both form and function.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers may easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 43:
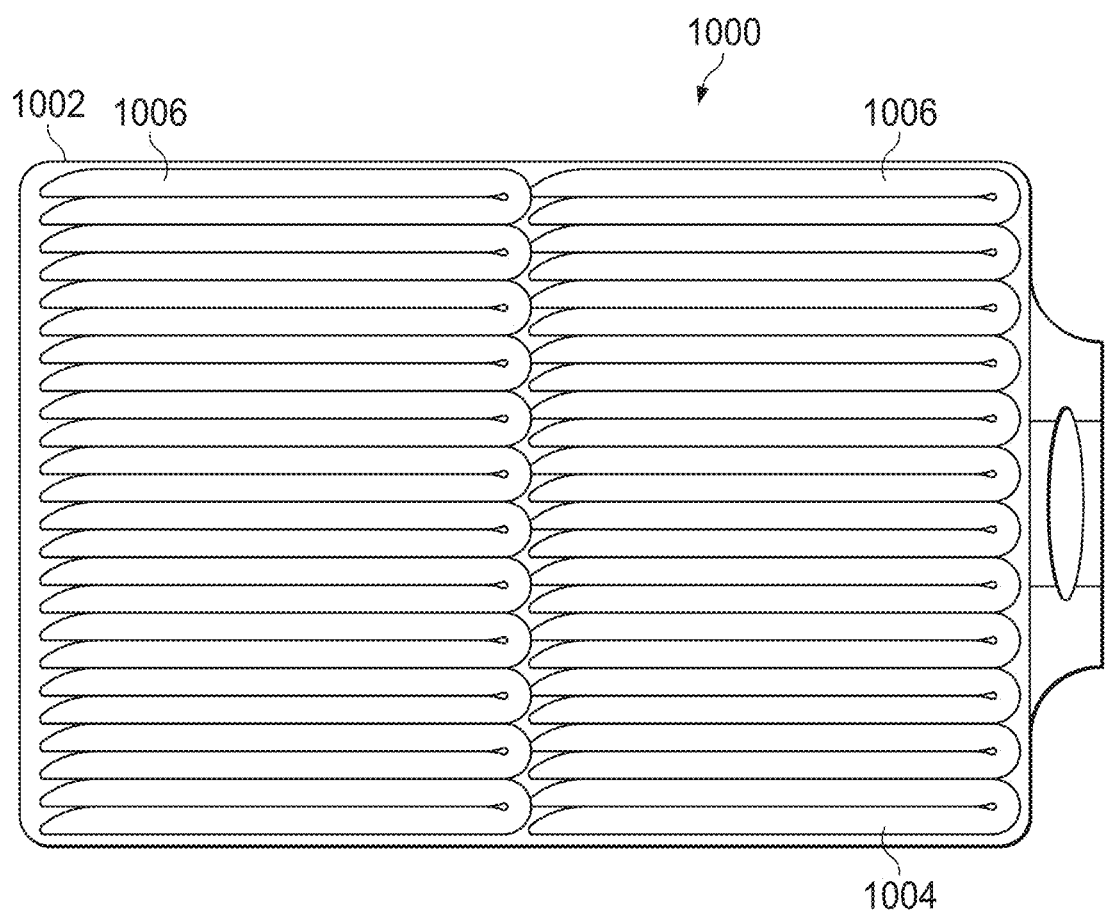
FIG. 43 is an illustration of an example page comprising a plurality of absorbent articles.

FIG. 43 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Absorbent Articles

The nonwoven fabrics of the present disclosure may form portions of absorbent articles. Absorbent articles may comprise taped diapers, pants, adult incontinence diapers or pads, sanitary napkins, panty liners, and/or other suitable absorbent articles. The nonwoven fabrics may also be useful in other consumer products. In an absorbent article context, the nonwoven fabrics may form an outer cover nonwoven material, a topsheet, an acquisition layer, a distribution layer, a portion of a core bag, an ear nonwoven material, a secondary topsheet, a waist belt laminate, and/or may form other suitable nonwoven absorbent article components. The nonwoven fabrics may also form portions of these components.

Figure 44:
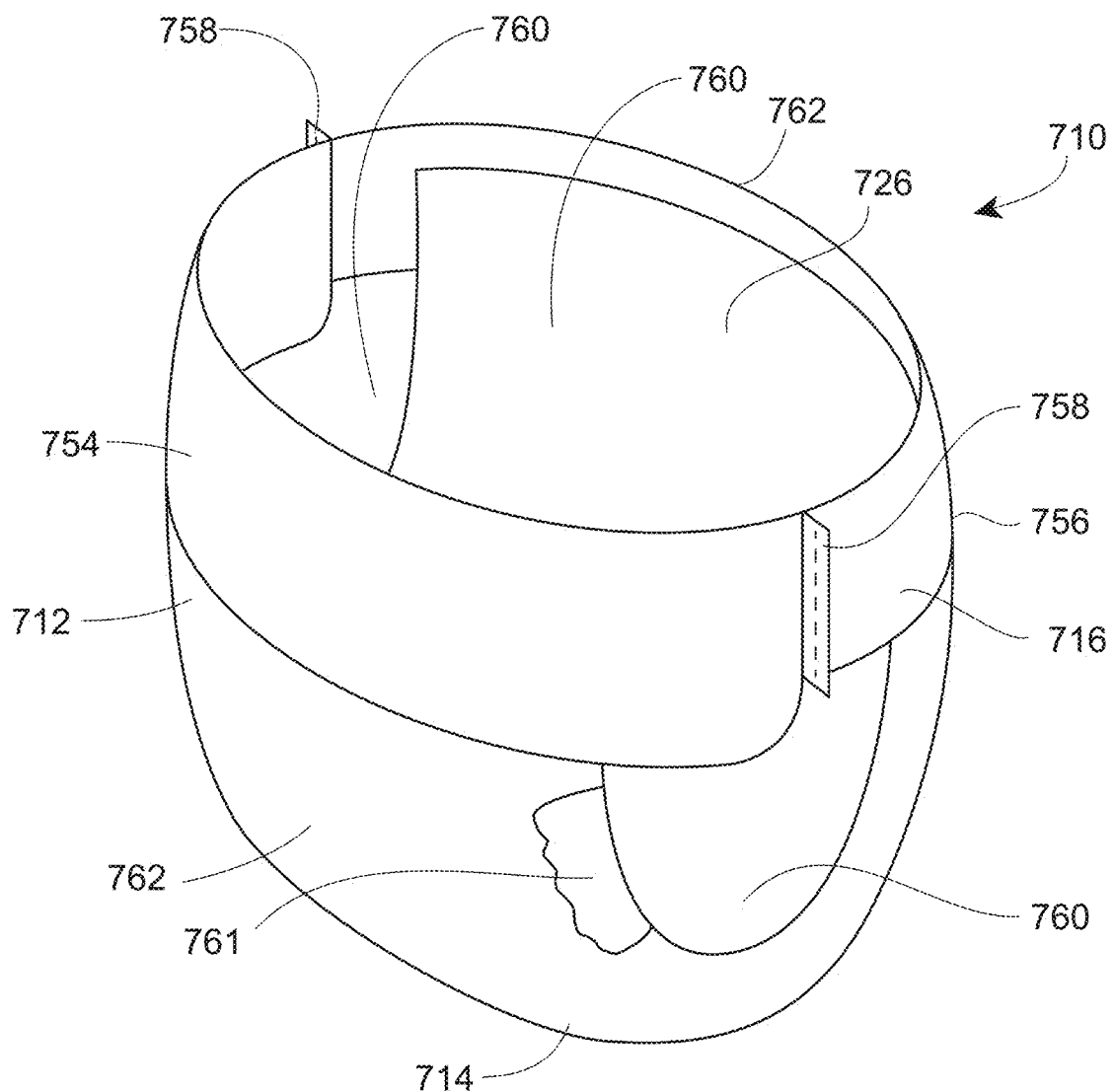
FIG. 44 is a front perspective view of an absorbent article comprising one or more nonwoven fabrics.
Figure 45:
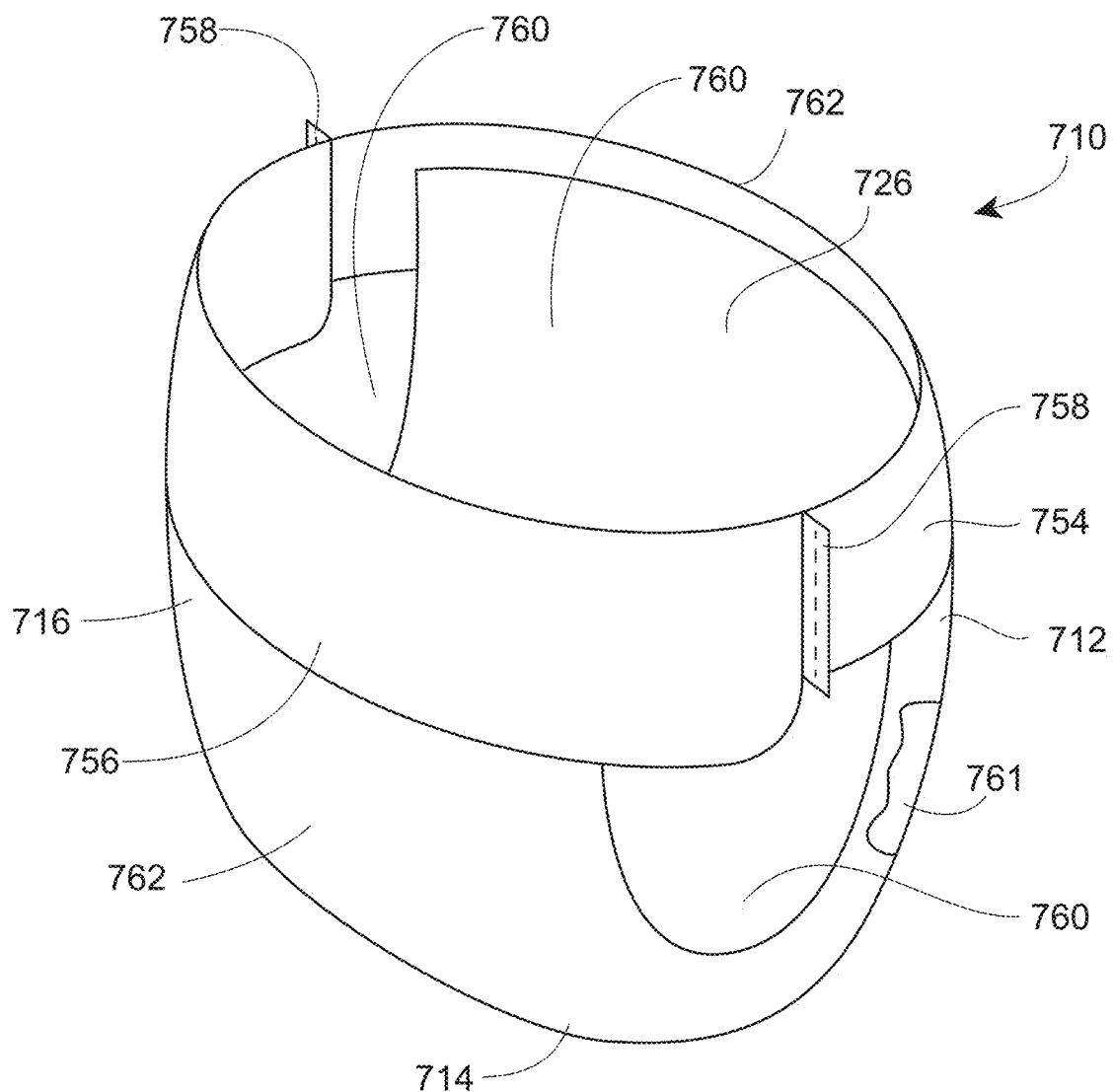
FIG. 45 is a back perspective view of the absorbent article of FIG. 44.

FIGS. 44 and 45 illustrate an example absorbent article in the form of a pant, although taped diapers are also within the scope of the present disclosure. The pant may comprise the nonwoven fabrics of the present disclosure, as for example, a topsheet and/or an outer cover nonwoven material, or portions of a topsheet and/or outer cover nonwoven material. FIG. 44 is a front perspective view of an absorbent article comprising one or more nonwoven fabrics of the present disclosure. FIG. 45 is a back perspective view of the absorbent article of FIG. 44.

Referring again to FIGS. 44 and 45, an absorbent article 710 in the form of a belted pant is illustrated. The absorbent article 710 comprises a front region 712, a crotch region 714, and a back region 716. The absorbent article may comprise a central chassis 726 extending at least partially between the front region 712 and the back region 716. The absorbent article 710 may define leg openings 760 and comprise a front waist belt 754 and a back waist belt 756.

The front and back belts 754, 756 may comprise a first extensible material and a second extensible material. An elastic member, such as an elastic film or a plurality of elastic strands, may be positioned intermediate the first extensible material and the second extensible material. The first waist belt 754 and the second waist belt 756 may be attached on their lateral edges to each other to form side seams 758. The side seams may comprise butt seams or overlaps seams.

The central chassis 752 may comprise a topsheet 760, a backsheet film 761, an absorbent core positioned at least partially intermediate the topsheet and the backsheet film. The topsheet 760 may form a portion of a wearer-facing surface of the absorbent article 710 and may comprise one or more of the nonwoven fabrics disclosed herein. The central chassis 752 may comprise an outer cover nonwoven material 762 forming a portion of a garment-facing surface of the absorbent article and being in a face-to-face relationship with the backsheet film. The outer cover nonwoven material 762 may comprise one or more of the nonwoven fabrics disclosed herein. The central chassis may comprise one or more acquisition layers and/or one or more distribution layers at least partially intermediate the topsheet and the absorbent core. The nonwoven fabrics may comprise crimped fibers.

Emtec

The present disclosure provides a solution to the problem discussed in the background section by providing absorbent articles comprising nonwoven fabrics with improved softness while still having high texture. The present disclosure further solves the contradiction between high softness and high texture while simultaneously providing some improvements in fluid handling, including rapid strikethrough of bodily exudates and enhanced skin and topsheet dryness. Typically, the nonwoven fabrics of the present disclosure may form at least a portion of a wearer-facing surface (e.g., topsheet) and at least a portion of a garment-facing surface (e.g., outer cover nonwoven material). Softness, texture (i.e., smoothness), and/or stiffness may be measured by an Emtec Tissue Softness Analyzer, according to the Emtec Test herein. Tactile softness is measured as TS7. Texture/Smoothness is measured as TS750. Stiffness is measured as D.

All of Examples 1-10 below are side-by-side bicomponent spunbond nonwoven fabrics produced by spinning a 30:70 ratio of Polypropylene (PP3155 obtained from Exxon Mobil Corporation) and 25/75 blend of polypropylenes (PP3155 and PP3854 obtained from Exxon Mobil Corporation) in a round fiber configuration. Approximately, 1% Titanium dioxide and 1% Erucamide were added to the polymers to improve whiteness and softness. In the topsheet of Example 2, a blue pigment melt additive 0.25% by weight of the nonwoven fabric was added to enhance the visual perception of three-dimensionality. The nonwoven fabrics were all spun on a forming belt having a three-dimensional pattern as generally described with respect to FIG. 16, although the patterns are different. The belts were moving at a linear speed of about 28 meters per minute to form the 25 gsm nonwoven fabrics. The belt was run at slower linear speeds for the higher basis weight nonwoven outer cover materials in Examples 7-10. Fibers of the nonwoven fabrics of Examples 1-10 were compacted by a heated compaction rolls 70, 72, and further bonded with 8% dot pattern calendar roll at about 140 C temperature.

closure may also have a TS750 value in the range of about 4 dB $V^2$ rms to about 30 dB $V^2$ rms, about 6 dB $V^2$ rms to about 30 dB $V^2$ rms, about 6 dB $V^2$ rms to about 20 dB $V^2$ rms, about 6 dB $V^2$ rms to about 15 dB $V^2$ rms, about 6 dB $V^2$ rms to about 12 dB $V^2$ rms, or about 6.5 dB $V^2$ rms to about 10 dB $V^2$ rms. The portion of, or all of, the wearer-facing surfaces of the topsheets of the present disclosure may also have a D value in the range of about 1 mm/N to about 10 mm/N, about 3 mm/N to about 8 mm/N, about 2 mm/N to about 6 mm/N, about 2 mm/N to about 4 mm/N, or about 3 mm/N to about 4 mm/N. All values are measured according to the Emtec Test herein. The TS7 value is tactile softness, so low numbers are desired (the lower the number, the more soft the material is). The TS750 value is texture so a high number is desired (the higher the number, the more texture the material has). Having a low TS7 value and a high texture value is contradictory in that typically the more

TABLE 5

Emtec properties of comparative example topsheets and present disclosure topsheet examples

Figure 46:
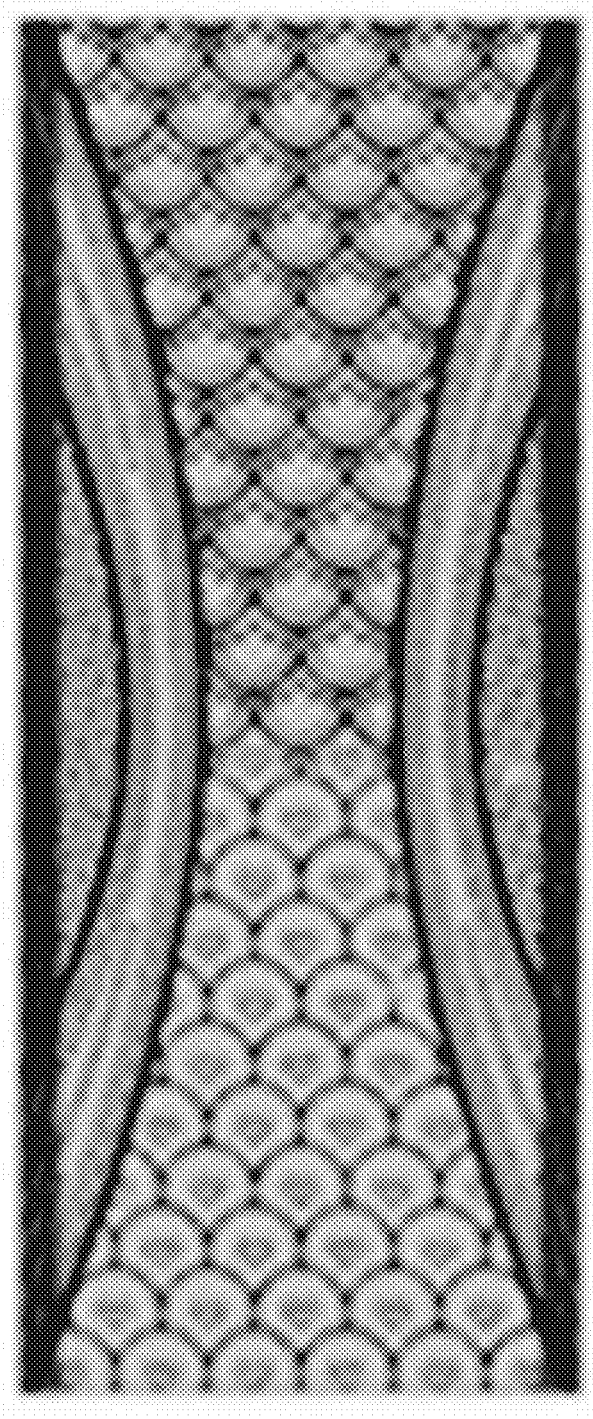
FIGS. 46-48 are example patterns of nonwoven topsheets of the present disclosure.
Figure 47:
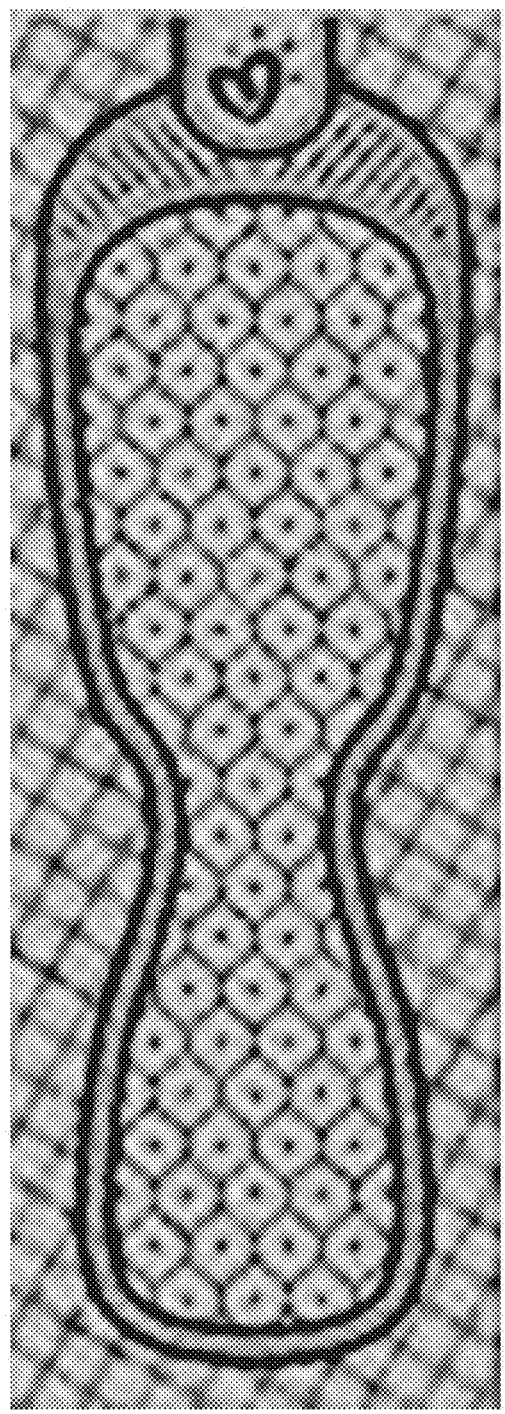
Figure 48:
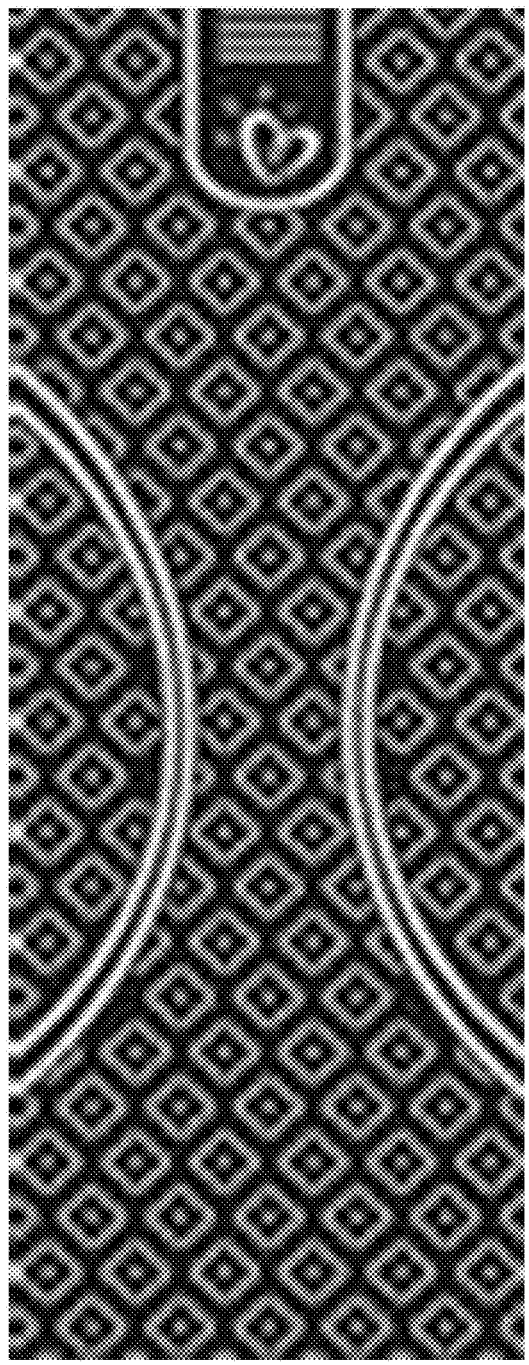

| Product | Comparative Example 1: Goon Premium, Purchased November 2018 in China | Comparative Example 2: Merries, Purchased November 2018 in China | Comparative Example 3: P&G Pampers Premium Care, Produced April 2017 in Japan | Example 1: Pattern of FIG. 46, 25 gsm | Example 2: Pattern of FIG. 47, 25 gsm, 0.25% blue melt additive | Example 3: Pattern of FIG. 47, 25 gsm, | Example 4: Pattern of FIG. 48, 25 gsm |
|---|---|---|---|---|---|---|---|
| Stiffness (D) mm/N | 4.9 | 4.4 | 4.3 | 3.95 | 3.16 | 3.9 | 3.9 |
| Softness (TS7)-Micro dB $V^2$ rms | 6.4 | 4.9 | 7.0 | 3.8 | 2.85 | 3.7 | 3.8 |
| Smoothness (TS750)-Macro dB $V^2$ rms | 2.9 | 15.1 | 4.1 | 8.29 | 9.6 | 7.3 | 7 |

* All values of Table 5 are measured according to the Emtec Test herein.

A portion of, or all of, wearer-facing surfaces of the topsheets of the present disclosure may have a TS7 value in the range of about 1 dB $V^2$ rms to about 4.5 dB $V^2$ rms, about 2 dB $V^2$ rms to about 4.5 dB $V^2$ rms, or about 2 dB $V^2$ rms to about 4.0 dB $V^2$ rms. The portion of, or all of, the wearer-facing surfaces of the topsheets of the present disclosure texture a nonwoven fabric has, the less soft it is. The Applicants, without wishing to be bound by theory, have discovered the unexpected results of highly textured nonwoven fabrics that still are very soft by providing a select range of region 1 and region 2 areas in the nonwovens fabrics, as discussed below.

TABLE 6

Emtec properties of comparative example outer cover nonwoven materials and present disclosure outer cover examples

Figure 50:
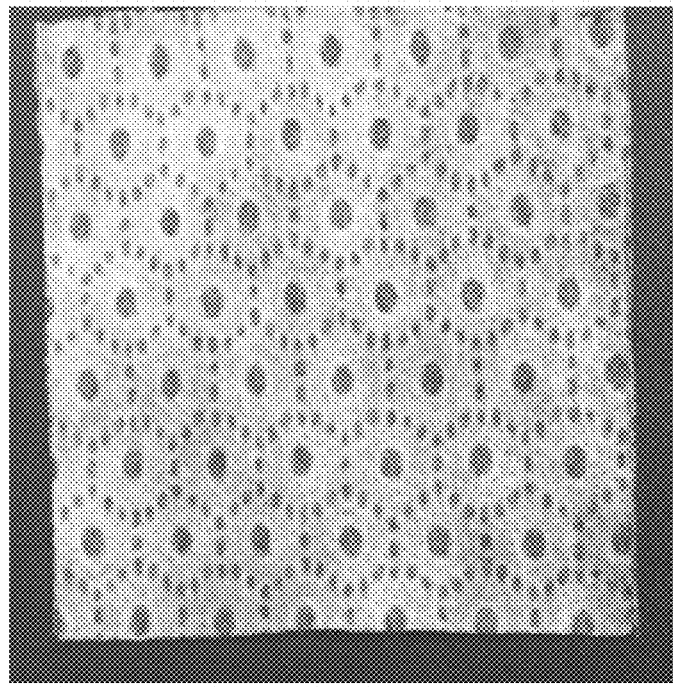
FIGS. 49-50 are example patterns of outer cover nonwoven materials of the present disclosure.
Figure 49:
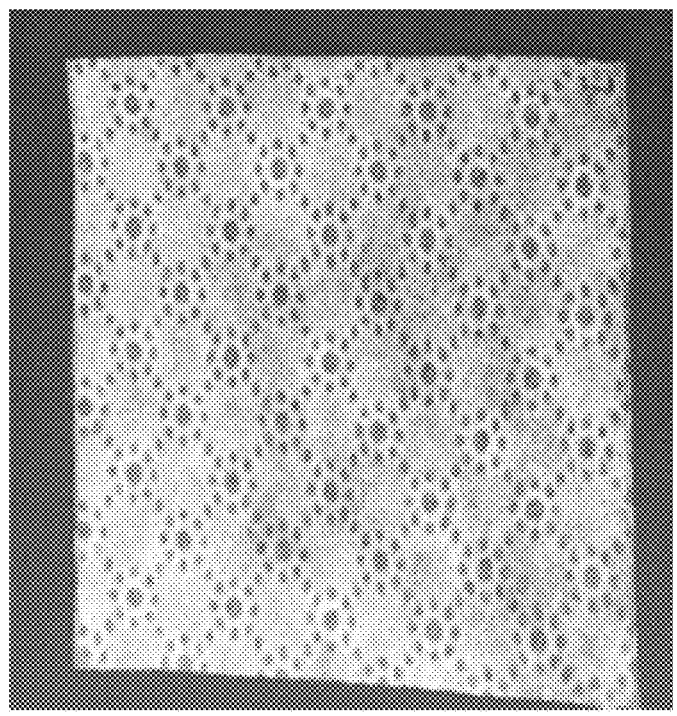

| Product | Comparative Example 1: Goon Premium, Purchased November 2018 in China | Comparative Example 2: Merries, Purchased November 2018 in China | Comparative Example 3: P&G Pampers Premium Care, Produced April 2017, in Japan | Example 5: Pattern of FIG. 49, 25 gsm | Example 6: Pattern of FIG. 50, 25 gsm, | Example 7: Pattern of FIG. 49, 35 gsm, | Example 8: Pattern of FIG. 50, 35 gsm | Example 9: Pattern of FIG. 49, 46 gsm | Example 10: Pattern of FIG. 50, 46 gsm |
|---|---|---|---|---|---|---|---|---|---|
| Stiffness (D) mm/N | 4.1 | 2.9 | 4.1 | 4.66 | 4.67 | 3.8 | 3.97 | 3.53 | 3.55 |
| Softness (TS7)-Micro dB $V^2$ rms | 4.7 | 3.1 | 3.1 | 2.69 | 2.79 | 2.83 | 2.74 | 3.04 | 2.88 |

TABLE 6-continued

Emtec properties of comparative example outer cover nonwoven materials and present disclosure outer cover examples

| Product | Comparative Example 1: Goon Premium, Purchased November 2018 in China | Comparative Example 2: Merries, Purchased November 2018 in China | Comparative Example 3: P&G Pampers Premium Care, Produced April 2017, in Japan | Example 5: Pattern of FIG. 49, 25 gsm | Example 6: Pattern of FIG. 50, 25 gsm | Example 7: Pattern of FIG. 49, 35 gsm | Example 8: Pattern of FIG. 50, 35 gsm | Example 9: Pattern of FIG. 49, 46 gsm | Example 10: Pattern of FIG. 50, 46 gsm |
|---|---|---|---|---|---|---|---|---|---|
| Smoothness (TS750)- Macro dB $V^2$ rms | 3.7 | 3.1 | 2.7 | 6.1 | 5.87 | 12.9 | 12.3 | 20.5 | 17.5 |

* All values of Table 6 are measured according to the Emtec Test herein.

A portion of the garment-facing surface of the outer cover nonwoven materials of the present disclosure may have a TS7 value in the range of about 1 dB $V^2$ rms to about 4.5 dB $V^2$ rms, about 2 dB $V^2$ rms to about 4.5 dB $V^2$ rms, or about 2 dB $V^2$ rms to about 4.0 dB $V^2$ rms. The portion of the garment-facing surfaces of the outer cover nonwoven materials of the present disclosure may also have a TS750 value in the range of about 4 dB $V^2$ rms to about 30 dB $V^2$ rms, about 6 dB $V^2$ rms to about 30 dB $V^2$ rms, about 6 dB $V^2$ rms to about 20 dB $V^2$ rms, about 6 dB $V^2$ rms to about 15 dB $V^2$ rms, about 6 dB $V^2$ rms to about 12 dB $V^2$ rms, or about 6.5 dB $V^2$ rms to about 10 dB $V^2$ rms. The portion of the garment-facing surfaces of the outer cover nonwoven materials of the present disclosure may also have a D value in the range of about 1 mm/N to about 10 mm/N, about 3 mm/N to about 8 mm/N, about 2 mm/N to about 6 mm/N, about 2 mm/N to about 4 mm/N, or about 3 mm/N to about 4 mm/N. All values are measured according to the Emtec Test herein. Having a low TS7 value and a high texture value is contradictory in that typically the more texture a nonwoven fabric has, the less soft it is. The Applicants, without wishing to be bound by theory, have discovered the unexpected results of highly textured nonwoven fabrics that still are very soft by providing a select range of region 1 and region 2 areas in the nonwovens fabrics, as discussed below.

It may be desirable to have the certain TS7 and TS750 properties discussed above in both the outer cover nonwoven material and the topsheet. This provides soft texture on both sides (i.e., wearer-facing and garment-facing) of the absorbent article.

An absorbent article may comprise a nonwoven topsheet, a backsheet, an absorbent core positioned at least partially intermediate the topsheet and the backsheet, and a nonwoven outer cover joined to the backsheet. A first portion of a wearer-facing side of the nonwoven topsheet and a second portion of a garment-facing side of the nonwoven outer cover may each have a TS7 value in the range of about 1 dB $V^2$ rms to about 4.5 dB $V^2$ rms, according to the Emtec Test. The second portion of the garment-facing side of the nonwoven outer cover may have a TS750 value that is about 1.2 to about 4 times, about 1.3 to about 3 times, or about 1.5 to about 2 times greater than a TS750 value of the first portion of the wearer-facing side of the nonwoven topsheet.

% Region 1 and Region 2 Areas

To achieve the desired results of the present disclosure of improved softness together with increased texture in the nonwoven fabrics, such as the outer cover nonwoven materials and the topsheets, it may be desirable to have a total region one area (e.g., low basis weight areas) in a portion of the nonwoven fabrics (corresponding to a resin pattern on the belt) in the range of about 5% to about 25%, about 5% to about 20%, or about 10% to about 20%, of a total area of the portion of the nonwoven fabrics, with the remainder of the portion of the nonwoven fabrics being a total region two area (e.g., high basis weight areas) (corresponding to areas on the belt that are resin free). The higher basis weight areas are typically softer than the low basis weight areas because the higher basis weight areas have more fibers. Nonwoven fabrics having low basis weight areas in the range of about 5% to about 20% of the total nonwoven fabric may typically achieve good dryness and good softness. Below 5% low basis weight areas, typically high softness may be achieved, but typically not good dryness. Above 25% low basis weight areas, typically good dryness may be achieved, but typically not good softness.

In addition to the benefits detailed above, another benefit of the shaped, soft and textured nonwoven fabrics of the present disclosure is the ability to provide a nonwoven fabric with microzones that comprise one or more hydrophobic regions and one or more separate hydrophilic regions. The hydrophilicity and/or hydrophobicity in a particular region of the microzone may be determined by a Time to Wick measurement using the Time to Wick Test Method as described herein and/or a Contact Angle measurement using the Contact Angle Test Method as described herein. As used herein, the term "hydrophilic", in reference to a particular region of the microzone, means that when tested using the Time to Wick Test Method, the Time to Wick for that particular region is less than 10 seconds. As used herein, the term "hydrophobic", in reference to a particular region of the microzone, means that when tested using the Contact Angle Test Method, the Contact Angle for that particular region is 90° or greater.

Table 7 below details Contact Angle and Time to Wick measurements for shaped, soft, and textured nonwoven fabrics as detailed herein. For both Examples 11 and 12 below, the nonwoven fabric was made on a belt as described in FIG. 16, with the nonwoven fabrics having an appearance similar to that shown in FIG. 2.

TABLE 7

Contact Angle and Time to Wick Values for Shaped, Soft, and Textured Nonwoven Fabrics of the Disclosure

| Example No. | Region | Contact Angle (θc) | Time to Wick (seconds) |
|---|---|---|---|
| Example 11 | First Region | 135 | 60 |
|  | Second Region | 0 | 0.307 |

TABLE 7-continued

Contact Angle and Time to Wick Values for Shaped, Soft,
and Textured Nonwoven Fabrics of the Disclosure

| Example No. | Region | Contact Angle (θc) | Time to Wick (seconds) |
|---|---|---|---|
| Example 12 | First Region | 126 | 60 |
|  | Second Region | 0 | 2.360 |

Example 11

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration. The nonwoven fabric was spun on a forming belt having a repeating pattern as described in FIG. 16 moving at a linear speed of about 25 meters per minute to form a fabric 10 having an average basis weight of 25 grams per square meter with a repeating pattern of diamond shapes as shown in FIG. 2. Fibers of the fabric were compacted by compaction rolls 70, 72, but rather than be calendared, further bonding was achieved by a through-air bonding unit at a temperature of 145° C.

A surfactant, Stantex S 6327 (a combination of castor oil ethoxylates with PEG diesters), supplied by Pulcra Chemicals, was then disposed on the back side surface of the nonwoven fabric (i.e., the flat side surface opposite the side with the relatively pillowy three-dimensional features disposed thereon) through a kiss coating process. The coating process was performed using a Reicofil Kiss Roll and Omega drying process, both of which are generally known in the art. The surfactant used in the kiss roll process was at a 6% surfactant concentration in water at a temperature of 40° C. The kiss roll contact angle was set at 250° and the drying temperature was 80° C. The nonwoven fabric was then brought into contact with the kiss roll operating at a speed of 13 rpm, delivering 0.45 wt % surfactant to the nonwoven fabric (% surfactant is weight of added surfactant per 1 m² divided by weight of 1 m² nonwoven fabric).

Example 12

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration. The nonwoven fabric was spun on a forming belt having a repeating pattern as described in FIG. 16 moving at a linear speed of about 25 meters per minute to form a fabric 10 having an average basis weight of 25 grams per square meter with a repeating pattern of diamond shapes as shown in FIG. 2. Fibers of the fabric were compacted by compaction rolls 70, 72, but rather than be calendared, further bonding was achieved by a through-air bonding unit at a temperature of 145° C.

A surfactant, Stantex S 6327 (a combination of castor oil ethoxylates with PEG diesters), supplied by Pulcra Chemicals, was then disposed on the front side surface of the nonwoven fabric (i.e., the side with the relatively pillowy three-dimensional features disposed thereon) through an inkjet printing process. The inkjet printing process was performed using a Dimatix DMP 2831 inkjet printer, fitted with a cartridge model #DMC-11610/PM 700-10702-01 (10 pL). The print head temperature was 40° C. The surfactant used in the inkjet printing process consisted of 75% w/w Stantex S 6327 and 25% w/w Ethanol. Surfactant was printed in the second regions of the microzones of the nonwoven fabric by orienting the nonwoven fabric sample such that the second regions of a first row of microzones were aligned with the print head direction and printing a first series of straight lines, with droplet spacing adjusted to 170 um. The nonwoven fabric sample was then turned by an angle such that the second regions of a second row of microzones were aligned with the print head and a second series of straight lines were printed at 170 um. The basis weight of the fibers of the second region is about 16.0 gsm. The basis weight of the surfactant that was inkjet printed onto the second region is about 0.25 gsm. Accordingly, the amount of surfactant printed locally on the second region was determined to be about 1.6 wt % surfactant (0.25 gsm/16.0 gsm). Overall, the amount of surfactant printed on the nonwoven fabric sample was determined by the ratio between printed line width and line spacing to be at about 0.2 wt % surfactant.

In addition to Stantex S 6327, the use of other surfactants to render first and/or second regions of particular microzones hydrophilic and/or hydrophobic (though any application method) is considered within the scope of the present disclosure.

The nonwoven fabrics detailed above comprise microzones with regions having differences in intensive properties, such as basis weight, density, or thickness, for example. Those same nonwoven fabrics may also simultaneously comprise such regions of the microzones that are particularly and separately hydrophobic and/or hydrophilic. Any of the nonwoven fabric examples detailed herein (e.g., samples that include zones and/or microzones with regions having differences in thickness, basis weight and/or volumetric density, and/or surfaces with the various TS7, TS750, and D values disclosed herein) may further have regions of a microzone with differences in hydrophilicity as detailed herein. Hydrophilicity may be provided through targeted application(s) of surfactant(s) onto particular regions of the microzones of the nonwoven fabric. For example, the second region of a microzone may have surfactant disposed thereon, while the first region of the same microzone may have no surfactant disposed thereon. Moreover, the first region of a microzone may have surfactant disposed thereon, while the second region of the same microzone may have no surfactant disposed thereon. For instance, in one microzone, the first or second region may have from about 0.01% to about 5.0%, about 0.05% to about 4.0%, about 1.0% to about 3.0%, and any concentric range within the range of about 0.01% to about 5.0% surfactant, and the other region has no surfactant (i.e., surfactant free). As an example, in one microzone, the second region may have from about 0.01% to about 5.0%, about 0.05% to about 4.0%, about 1.0% to about 3.0%, and any concentric range within the range of about 0.01% to about 5.0% surfactant, and the first region has no surfactant (i.e., surfactant free). Accordingly, some nonwoven fabrics disclosed herein have a microzone with at least one of the first and second regions having a surfactant, and the ratio of % surfactant in the first region to % surfactant in the second region is less than 1. Further, some nonwoven fabrics disclosed herein have a microzone with at least the second region of the microzone having a surfactant, and the ratio of % surfactant in the first region to % surfactant in the second region is less than 1.

As another example, the second region of a microzone may have a particular amount of surfactant or % surfactant disposed thereon, while the first region of the same microzone may have a different amount of surfactant or % surfactant disposed thereon. For instance, in one microzone, the first region may have from about 0.01% to about 2.0%, about 0.05% to about 1.5%, about 0.1% to about 1.0%, and any concentric range within the range of about 0.01% to about 2.0% surfactant, and the second region may have a differing amount. Moreover, in one microzone, the second region may have from about 0.01% to about 5.00, about 0.05% to about 4.0%, about 1.0% to about 3.0%, and any concentric range within the range of about 0.01% to about 5.0% surfactant, and the first region may have a differing amount. The % surfactant for a particular region of a microzone may be determined by taking the grams per square meter of surfactant disposed in the particular region and dividing it by the basis weight of the fibers of the shaped nonwoven fabric contained within the same region. The grams per square meter of surfactant disposed in a particular region may be determined using any currently known method in the art (e.g., gravimetric, etc.). The basis weight of the fibers of the nonwoven fabric contained within a particular region of a microzone may also be determined using any currently known method in the art (e.g., gravimetric, micro-CT, etc.).

A surfactant may be disposed on the nonwoven fabrics by any method generally known to those of skill in the art. Particular examples comprise kiss coating, inkjet printing, gravure printing, off-set gravure printing, flexo-graphic printing of the surfactant and registered printing of the surfactant. Any such method may dispose surfactant onto either the first and/or second surface of the nonwoven fabrics. For the overall shaped nonwoven fabric (taking into account all of the individual zones and microzones on the fabric), the surfactant may be added to the shaped nonwoven fabric in an amount from about 0.01% to about 2.0%, about 0.05% to about 1.5%, about 0.1% to about 1.0%, and any concentric range within the range of about 0.01% to about 2.0%. To calculate % surfactant added to the overall shaped nonwoven fabric, divide the grams per square meter of surfactant in the overall shaped nonwoven fabric by the basis weight of the overall shaped nonwoven fabric. The grams per square meter of surfactant disposed in the overall shaped nonwoven fabric may be determined using any currently known method in the art (e.g., gravimetric, etc.). The basis weight of the overall shaped nonwoven fabric may also be determined using any currently known method in the art (e.g., gravimetric, micro-CT, etc.).

Referring again to FIGS. 25 and 26 which show a portion of one pattern of a nonwoven fabric 10, a first zone 110 (on the left side of FIG. 25) is characterized by generally MD-oriented rows of variable width first regions 300 separated by MD-oriented rows of variable width second regions 310 (first and second region being within a microzone). The first region is also the three-dimensional feature 20 that defines the first and second regions 300, 310. A three-dimensional feature may be a portion of the nonwoven fabric 10 that was formed between or around a raised element of the forming belt, which in this description is the first region 300, such that the resulting structure has a relatively greater dimension in the Z-direction, a relatively higher basis weight, and a lower volumetric density, when compared to the second region 310. Moreover, the first region 300 may be hydrophobic and the second region 310 may be hydrophilic. Targeted addition of a surfactant to the second region 310 of the microzone may cause the second region to be hydrophilic. Accordingly, the first region 300 of the microzone may have a Contact Angle of greater than about 900, or between about 90° and about 140°, or between about 1100 and about 135°, or between about 125° and about 135°, or any concentric range contained within between about 900 and about 140°, when tested by the Contact Angle Test Method detailed herein. The second region 310 of the microzone may have a Contact Angle of less than 90° when tested by the contact Angle Test Method detailed herein. The first region 300 of the microzone may have a Time to Wick value of greater than about 10 seconds, or between about 10 seconds and 60 seconds, as measured by the Time to Wick Test Method detailed herein. The second region 310 of the microzone may have a Time to Wick value of less than about 10 seconds, less than about 5 seconds, or less than about 2.5 seconds, less than about 1 second, less than about 0.5 seconds, or in the range of about 0.5 seconds to about 10 seconds, or about 0.5 seconds to about 5 seconds, as measured by the Time to Wick Test Method detailed herein. Nonwoven fabrics contemplated herein include any of the above detailed parameter ranges for Contact Angle and/or Time to Wick measurements for the first region and/or the second region in combination with any of the other herein disclosed intensive properties/property differences for the same or different regions in the same or different microzone on the shaped nonwoven fabric.

Shaped nonwoven fabrics having the above detailed microzones with regions having differences in basis weight, density, or thickness, for example, while also simultaneously having such regions of a particular microzone being separately hydrophobic and/or hydrophilic may provide many useful applications such as topsheet materials for absorbent articles, as well as use in medical pads, wipes and cleaning pads.

Test Methods:

Localized Basis Weight

Localized basis weight of the nonwoven fabric may be determined by several available techniques, but a simple representative technique involves a punch die having an area of 3.0 cm² which is used to cut a sample piece of the web from the selected region from the overall area of a nonwoven fabric. The sample piece is then weighed and divided by its area to yield the localized basis weight of the nonwoven fabric in units of grams per meter squared. Results are reported as a mean of 2 samples per selected region.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 43). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Micro-CT Intensive Property Measurement Method

The micro-CT intensive property measurement method measures the basis weight, thickness and volumetric density values within visually discernable regions of a substrate sample. It is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, MA, or equivalent) to measure the basis weight, thickness and volumetric density intensive properties of regions within the sample.

Sample Preparation:

To obtain a sample for measurement, lay a single layer of the dry substrate material out flat and die cut a circular piece with a diameter of 30 mm.

If the substrate material is a layer of an absorbent article, for example a topsheet, backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston TX) can be used to remove a substrate layer from additional underlying layers, if necessary, to avoid any longitudinal and lateral extension of the material. Once the substrate layer has been removed from the article proceed with die cutting the sample as described above.

If the substrate material is in the form of a wet wipe, open a new package of wet wipes and remove the entire stack from the package. Remove a single wipe from the middle of the stack, lay it out flat and allow it to dry completely prior to die cutting the sample for analysis.

A sample may be cut from any location containing the visually discernible zone to be analyzed. Within a zone, regions to be analyzed are ones associated with a three-dimensional feature defining a microzone. The microzone comprises a least two visually discernible regions. A zone, three-dimensional feature, or microzone may be visually discernable due to changes in texture, elevation, or thickness. Regions within different samples taken from the same substrate material may be analyzed and compared to each other. Care should be taken to avoid folds, wrinkles or tears when selecting a location for sampling.

Image Acquisition:

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the xy-plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 μA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing:

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an xy-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the xy-plane where sample signal was first detected. The same procedure is followed for identifying the lower surface of the sample, except the z-direction voxels located are all the positions in the xy-plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the xy-plane. This raw thickness value is then converted to actual distance, in microns, by multiplying the voxel count by the 7 μm slice thickness resolution.

The third intensive property 2D image is the Volumetric Density Image. To generate this image divide each xy-plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties:

Begin by identifying the region to be analyzed. A region to be analyzed is one associated with a three-dimensional feature defining a microzone. The microzone comprises a least two visually discernible regions. A zone, three-dimensional feature, or microzone may be visually discernable due to changes in texture, elevation, or thickness. Next, identify the boundary of the region to be analyzed. The boundary of a region is identified by visual discernment of differences in intensive properties when compared to other regions within the sample. For example, a region boundary can be identified based by visually discerning a thickness difference when compared to another region in the sample. Any of the intensive properties can be used to discern region boundaries on either the physical sample itself of any of the micro-CT intensive property images. Once the boundary of the region has been identified, draw an oval or circular "region of interest" (ROI) within the interior of the region. The ROI should have an area of at least 0.1 mm2, and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

Emtec Test

The Emtec Test is performed on portions of interest of outer cover nonwoven materials or topsheets. In this test, TS7, TS750, and D values are measured using an Emtec Tissue Softness Analyzer ("Emtec TSA") (Emtec Electronic GmbH, Leipzig, Germany) interfaced with a computer running Emtec TSA software (version 3.19 or equivalent). The Emtec TSA includes a rotor with vertical blades which rotate on the test sample at a defined and calibrated rotational speed (set by manufacturer) and contact force of 100 mN. Contact between the vertical blades and the test sample creates vibrations both in the blades and in the test piece, and the resulting sound is recorded by a microphone within the instrument. The recorded sound file is then analyzed by the Emtec TSA software to determine TS7 and TS750 values. The D value is a measure of sample stiffness and is based on the vertical distance required for the contact force of the blades on test sample to be increased from 100 mN to 600 mN. The sample preparation, instrument operation, and testing procedures are performed according the instrument manufacturer's specifications.

Sample Preparation

A test sample is prepared by cutting a square or circular portion of interest from the outer cover nonwoven material or topsheet of an absorbent article. It is preferable that freeze spray is not used to remove the portion of the outer cover nonwoven material or topsheet to be analyzed, though it is acceptable to use freeze spray in a distal region to aid in initiating the separation of layers. Test samples are cut to a length and width (diameter in the case of a circular sample) of no less than about 90 mm and no greater than about 120 mm to ensure the sample can be clamped into the TSA instrument properly. (If an absorbent article does not contain a sufficiently large area of the substrate of interest to extract a sample of the size specified above, it is acceptable to sample equivalent material from roll stock.) Test samples are selected to avoid unusually large creases or folds within the testing region. Six substantially similar replicate samples are prepared for testing.

All samples are equilibrated at TAPPI standard temperature and relative humidity conditions (23° C.±2° C. and 50%±2%) for at least 2 hours prior to conducting the TSA testing, which is also conducted under TAPPI conditions.

Testing Procedure

The instrument is calibrated according to the Emtec's instructions using the 1-point calibration method with the appropriate reference standards (so-called "ref.2 samples," or equivalent, available from Emtec).

A test sample is mounted in the instrument with the surface of interest facing upward, and the test is performed according to the manufacturer's instructions. The software displays values for TS7, TS750, and D when the automated instrument testing routine is complete. TS7 and TS750 are each recorded to the nearest 0.01 dB V$^2$ rms, and D is recorded to the nearest 0.01 mm/N. The test sample is then removed from the instrument and discarded. This testing procedure is performed individually on the corresponding surfaces of interest of each of the six of the replicate samples (wearer-facing surface for topsheet samples and garment-facing surface for outer cover nonwoven material samples).

The value of TS7, TS750, and D are each averaged (arithmetic mean) across the six sample replicates. The average values of TS7 and TS750 are reported to the nearest 0.01 dB V² rms. The average value of D is reported to the nearest 0.01 mm/N.

Contact Angle and Time to Wick Test Methods

Contact Angle and Time to Wick measurements are determined using a sessile drop experiment. A specified volume of Type II reagent distilled water (as defined in ASTM D1193) is applied to the surface of a test sample using an automated liquid delivery system. A high speed video camera captures time-stamped images of the drop over a 60 second time period at a rate of 900 frames per second. The contact angle between the drop and the surface of the test sample is determined for each captured image by image analysis software. The time to wick is determined as the time it takes the contact angle of a drop absorbing into the test sample to decrease to a contact angle<10°. All measurements are performed at constant temperature (23° C.±2 CO) and relative humidity (50%±2%).

An automated contact angle tester is required to perform this test. The system includes of a light source, a video camera, a horizontal specimen stage, a liquid delivery system with a pump and micro syringe and a computer equipped with software suitable for video image capture, image analysis and reporting contact angle data. A suitable instrument is the Optical Contact Angle Measuring System OCA 20 (DataPhysics Instruments, Filderstadt, Germany), or equivalent. The system must be able to deliver an 8.2 microliter drop and be capable of capturing images at a rate of 900 frames per second. The system is calibrated and operated per the manufacturer's instructions, unless explicitly stated otherwise in this testing procedure. To obtain a test sample for measurement, lay a single layer of the dry substrate material out flat and cut a rectangular test sample 15 mm in width and about 70 mm in length. The width of the sample may be reduced as necessary to ensure that the test region of interest is not obscured by surrounding features during testing. With a narrower sample strip care must be taken that the liquid drop does not reach the edge of the test sample during testing, otherwise the test must be repeated. Precondition samples at 23° C.±2° C. and 50%±2% relative humidity for 2 hours prior to testing.

Sample Preparation

A test sample may be cut from any location containing the visually discernible zone to be analyzed. Within a zone, regions to be analyzed are ones associated with a three-dimensional feature defining a microzone. The microzone comprises at least two visually discernible regions. A zone, three-dimensional feature, or microzone may be visually discernable due to changes in texture, elevation, or thickness. Regions within different test samples taken from the same substrate material can be analyzed and compared to each other. Care should be taken to avoid folds, wrinkles or tears when selecting a location for sampling.

If the substrate material is a layer of an absorbent article, for example a topsheet or outer cover nonwoven material, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston TX) may be used to remove a substrate layer from additional underlying layers, if necessary, to avoid any longitudinal and lateral extension of the material. Once the substrate layer has been removed from the absorbent article proceed with cutting the test sample. If the substrate material is in the form of a wet wipe, open a new package of wet wipes and remove the entire stack from the package. Remove a single wipe from the middle of the stack, lay it out flat and allow it to dry completely prior to cutting the sample for analysis.

Testing Procedure

The test sample is positioned onto the horizontal specimen stage with the test region in the camera's field of view beneath the liquid delivery system needle, with the test side facing up. The test sample is secured in such a way that it lies flat but unstrained, and any interaction between the liquid drop and the underlying surface is avoided to prevent undue capillary forces. A 27 gauge blunt tip stainless steel needle (ID 0.23 mm, OD 0.41 mm) is positioned above the test sample with at least 2 mm of the needle tip in the camera's field of view. Adjust the specimen stage to achieve a distance of about 3 mm between the tip of the needle and the surface of the test sample. An 8.2 microliter drop of reagent distilled water is formed at a rate of 1 microliter per second and allowed to freely fall onto the surface of the test sample. Video image capture is initiated prior to the drop contacting the surface of the test sample, and subsequently a continual series of images is collected for a duration of 60 seconds after the drop contacts the surface of the test sample. Repeat this procedure for a total of five (5) substantially similar replicate test regions. Use a fresh test sample or ensure that the previous drop's wetted area is avoided during subsequent measurements.

On each of the images captured by the video camera, the test sample surface and the contour of the drop is identified and used by the image analysis software to calculate the Contact Angle for each drop image and reported to the nearest 0.1 degree. The Contact Angle is the angle formed by the surface of the test sample and the tangent to the surface of the liquid drop in contact with the test sample. For each series of images from a test, time zero is the time at which the liquid drop makes contact with the surface of the test sample. Measure and record the Contact Angle on the drop image that corresponds to time zero plus five (5) seconds. The Contact Angle at five seconds is reported as 0° if the droplet has been completely absorbed by the test sample within 5 seconds. Repeat this procedure for the five replicate test regions. Calculate the arithmetic mean of the Contact Angle at time zero plus five seconds for the five replicate test regions, and report this value as the Contact Angle to the nearest 0.1 degrees.

Time to Wick is defined as the time it takes the contact angle of a drop absorbing into the test sample to decrease to a contact angle <10°. Time to Wick is measured by identifying the first image of a given series where the contact angle has decreased to a contact angle <10°, and then based on that image, calculating and reporting the length of time that has elapsed from time zero. Time to Wick is reported as 60 seconds if a contact angle less than 10° is not reached within 60 seconds. Repeat this procedure for the five replicate test regions. Calculate the arithmetic mean of the Time to Wick for the five replicate test regions, and report this value to the nearest 0.1 milliseconds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. An absorbent article comprising:
a topsheet;
a backsheet film;
an absorbent core positioned at least partially intermediate the topsheet and the backsheet;
an outer cover nonwoven material in a facing relationship with at least a portion of the backsheet film, the outer cover nonwoven material comprising a nonwoven fabric comprising a garment-facing surface;
wherein the outer cover nonwoven material is hydrophobic;
the nonwoven fabric comprising a visually discernible pattern of three-dimensional features on the garment-facing surface, each of the three-dimensional features defining a microzone comprising a first region and a second region, the first and second regions having a difference in values for an intensive property, wherein the intensive property is one or more of: thickness, basis weight, and volumetric density;
wherein the nonwoven fabric comprises bond skinning, wherein the bond skinning comprises thermally bonding fibers to form a film skin, and wherein an amount of thermal bonding in the first region differs from an amount of thermal bonding in the second region;
wherein the first region has a Time to Wick value in the range of about 10 second to about 60 seconds, according to the Time to Wick Test Method;
wherein the second region has a Time to Wick value in the range of about 0.5 seconds to about 10 seconds, according to the Time to Wick Test Method;
wherein a portion of the garment-facing surface has a total region one, lower basis weight area of about 5% to about 25% of a total area of the portion of the garment-facing surface, with a remainder of the portion of the garment-facing surface being a total region two, higher basis weight area, the portion having a TS7 value in the range of about 1 dB $V^2$ rms to about 4.5 dB $V^2$ rms, according to the Emtec Test; and
wherein the portion of the garment-facing surface has a TS750 value in the range of about 6 dB $V^2$ rms to about 30 dB $V^2$ rms, according to the Emtec Test.

2. The absorbent article of claim 1, wherein the portion of the garment-facing surface has a D value in the range of about 2 mm/N to about 6 mm/N.

3. The absorbent article of claim 1, wherein the nonwoven fabric comprises a spunbond nonwoven fabric.

4. The absorbent article of claim 1, wherein the topsheet comprises a second nonwoven fabric, the second nonwoven fabric comprising a wearer-facing surface;
the second nonwoven fabric comprising a visually discernible pattern of three-dimensional features on the wearer-facing surface, each of the three-dimensional features defining a microzone comprising a third region and a fourth region, the third and fourth regions having a difference in values for an intensive property, wherein the intensive property is one or more of: thickness, basis weight, and volumetric density;
wherein a portion of the wearer-facing surface of the topsheet has a TS7 value in the range of about 1 dB $V^2$ rms to about 4.5 dB $V^2$ rms, according to the Emtec Test; and
wherein the portion of the wearer-facing surface of the topsheet has a TS750 value in the range of about 6 dB $V^2$ rms to about 30 dB $V^2$ rms, according to the Emtec Test.

5. The absorbent article of claim 4, wherein the portion of the wearer-facing surface of the topsheet has a D value in the range of about 2 mm/N to about 6 mm/N.

6. The absorbent article of claim 4, wherein the nonwoven fabric of the outer cover nonwoven material and/or the second nonwoven fabric of the topsheet comprise crimped fibers.

7. The absorbent article of claim 4, wherein in at least one of the microzones the third region of the at least one microzone is hydrophobic and the fourth region of the at least one microzone is hydrophilic.

8. The absorbent article of claim 7, wherein in at least one of the microzones the fourth region of the at least one microzone comprises a surfactant and the third region of the at least one microzone is surfactant free.

9. The absorbent article of claim 4, wherein in at least one of the microzones the third region of the at least one microzone exhibits a Contact Angle of greater than 90 degrees, according to the Contact Angle Test Method.

10. The absorbent article of claim 1, wherein the difference in thickness between the first and second regions of at least one microzone is greater than about 25 microns, according to the Micro-CT Intensive Property Measurement Method.

11. The absorbent article of claim 1, wherein the difference in basis weight between the first and second regions of at least one microzone is greater than about 5 gsm, according to the Micro-CT Intensive Property Measurement Method.

12. The absorbent article of claim 1, wherein the difference in volumetric density between the first and second regions of at least one microzone is greater than about 0.042 g/cc, according to the Micro-CT Intensive Property Measurement Method.

13. The absorbent article of claim 4, wherein the difference in thickness between the third and fourth regions of at least one microzone is greater than about 25 microns, according to the Micro-CT Intensive Property Measurement Method.

14. The absorbent article of claim 4, wherein the difference in basis weight between the third and fourth regions of at least one microzone is greater than about 5 gsm, according to the Micro-CT Intensive Property Measurement Method.

15. The absorbent article of claim 4, wherein the difference in volumetric density between the third and fourth regions of at least one microzone is greater than about 0.042 g/cc, according to the Micro-CT Intensive Property Measurement Method.

16. The absorbent article of claim 1, wherein the portion of the garment-facing surface has a TS750 in the range of about 6 dB $V^2$ rms to about 15 dB $V^2$ rms, according to the Emtec Test.

17. The absorbent article of claim 4, wherein the portion of the wearer-facing surface has a TS750 in the range of about 6 dB $V^2$ rms to about 15 dB $V^2$ rms, according to the Emtec Test.

18. The absorbent article of claim 1, wherein the portion of the garment-facing surface has a total region one area in the range of about 5% to about 25% of a total area of the portion of the garment-facing surface, with the remainder of the portion of the garment-facing surface being a total region two area.

19. The absorbent article of claim 4, wherein the portion of the wearer-facing surface has a total region one area in the range of about 5% to about 25% of a total area of the portion of the wearer-facing surface, with the remainder of the portion of the wearer-facing surface being a total region two area.

20. The absorbent article of claim 1, wherein the nonwoven fabric further comprises a wearer-facing surface, and wherein the bond skinning is applied only to the garment-facing surface such that fibers on the wearer-facing surface comprise no thermal bonding.

21. An absorbent article comprising:
a topsheet;
a backsheet film;
an absorbent core positioned at least partially intermediate the topsheet and the backsheet film;
an outer cover nonwoven material in a facing relationship with at least a portion of the backsheet film, the outer cover nonwoven material comprising a nonwoven fabric comprising a garment-facing surface;
wherein the outer cover nonwoven material is hydrophobic;
first and second visually discernible zones on the garment-facing surface;
each of the first and second visually discernible zones having a pattern of three-dimensional features;
each of the three-dimensional features defining a microzone comprising a first region and a second region;
the first and second regions having a difference in values for an intensive property;
the difference in values for an intensive property for at least one of the microzones in the first zone is different from the difference in values for the intensive property for at least one of the microzones in the second zone;
wherein the nonwoven fabric comprises bond skinning, wherein the bond skinning comprises thermally bonding fibers to form a film skin, and wherein an amount of thermal bonding in the first region differs from an amount of thermal bonding in the second region;
wherein the first region has a Time to Wick value in the range of about 10 second to about 60 seconds, according to the Time to Wick Test Method;
wherein the second region has a Time to Wick value in the range of about 0.5 seconds to about 10 seconds, according to the Time to Wick Test Method;
wherein a portion of the garment-facing surface has a total region one, lower basis weight area of about 5% to about 25% of a total area of the portion of the garment-facing surface, with the remainder of the portion of the garment-facing surface being a total region two, high basis weight area, the portion having a TS7 value in the range of about 1 dB $V^2$ rms to about 4.5 dB $V^2$ rms, according to the Emtec Test; and
wherein the portion of the garment-facing surface has a TS750 value in the range of about 6 dB $V^2$ rms to about 30 dB $V^2$ rms, according to the Emtec Test.

* * * * *